(12) United States Patent
Subramanian et al.

(10) Patent No.: US 8,951,752 B2
(45) Date of Patent: Feb. 10, 2015

(54) N-DEMETHYASE GENES AND USES THEREOF

(71) Applicant: University of Iowa Research Foundation, Iowa City, IA (US)

(72) Inventors: Venkiteswaran Subramanian, Coralville, IA (US); Michael Tai-Man Louie, Longmont, CO (US); Ryan Summers, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/344,037

(22) PCT Filed: Oct. 18, 2012

(86) PCT No.: PCT/US2012/060894
§ 371 (c)(1),
(2) Date: Mar. 10, 2014

(87) PCT Pub. No.: WO2013/059507
PCT Pub. Date: Apr. 25, 2013

(65) Prior Publication Data
US 2014/0227729 A1    Aug. 14, 2014

Related U.S. Application Data

(60) Provisional application No. 61/549,339, filed on Oct. 20, 2011.

(51) Int. Cl.
| | |
|---|---|
| *C12Q 1/34* | (2006.01) |
| *C12N 15/00* | (2006.01) |
| *C12N 1/20* | (2006.01) |
| *C12N 9/14* | (2006.01) |
| *C07K 1/00* | (2006.01) |
| *C07H 21/04* | (2006.01) |
| *C12N 9/02* | (2006.01) |
| *C12P 17/18* | (2006.01) |
| *C12Q 1/26* | (2006.01) |

(52) U.S. Cl.
CPC ............. *C12N 9/0071* (2013.01); *C12Y 114/13* (2013.01); *C12Y 114/13128* (2013.01); *C12N 9/0073* (2013.01); *C12P 17/182* (2013.01); *C12Q 1/26* (2013.01)
USPC ....... 435/18; 435/320.1; 435/252.3; 435/195; 530/350; 536/23.2

(58) Field of Classification Search
USPC .............. 435/18, 252.3, 320.1, 195; 530/350; 536/23.2
See application file for complete search history.

(56) References Cited

U.S. PATENT DOCUMENTS 5,550,041 A * 8/1996 Koide et al. ................... 435/119

FOREIGN PATENT DOCUMENTS

| DE | 4316882 A1 | 11/1993 |
|---|---|---|
| WO | WO-2013059507 A1 | 4/2013 |

OTHER PUBLICATIONS

"International Application Serial No. PCT/US2012/060894, International Search Report mailed Mar. 28, 2013", 7 pgs.
"International Application Serial No. PCT/US2012/060894, Invitation to Pay Additional Fees and Partial Search Report mailed Dec. 19, 2012", 6 pgs.
"International Application Serial No. PCT/US2012/060894, Written Opinion mailed Mar. 28, 2013", 9 pgs.
Dash, et al., "Catabolic pathways and Botechnological applications of microbial caffeine degradation", Biotechnology Letters, vol. 28 (Jan. 1, 2006), 1993-2002.
Summers, Ryan M, et al., "Characterization of a broad-specificity non-haem iron N-demethylase from Pseudomonas putida CBB5 capable of utilizing several purine alkaloids as sole carbon and nitrogen source", Microbiology (Reading), vol. 157, No. Part 2, (Feb. 2011), 583-592.
Summers, Ryan M, et al., "Novel, Highly Specific N-Demethylases Enable Bacteria to Live on Caffeine and Related Purine Alkaloids", Journal of Bacteriology, vol. 194, No. 8 (Apr. 2012), 2041-2049.
Yu, Chi Li, et al., "Two Distinct Pathway for Metabolism of Theophylline and Caffeinea are Coexpressed in *Pseudomonas putida* CBB", Journal of Bacteriology, vol. 191, No. 14, (Jul. 2009), 4624-4632.
"International Application Serial No. PCT/US2012/060894, International Preliminary Report on Patentability mailed May 1, 2014", 10 pgs.

* cited by examiner

*Primary Examiner* — Maryam Monshipouri
(74) *Attorney, Agent, or Firm* — Schwegman Lundberg & Woessner, P.A.

(57) ABSTRACT

The invention provides isolated nucleic acid encoding one or more gene products that allow for degradation of caffeine and related structures, and for preparation of intermediates in that catabolic pathway. Further provided are methods of using one or more of those gene products.

19 Claims, 20 Drawing Sheets

```
NdmA      M-EQ-AIINDEREYLRHFWHPVCTVTE    25
Cdm       M-EQ-TIMNNDREYLRHFWHPVCTVTE    25
NdmB      MKEQLKPLLEDKTYLRHFWHPVCTL--    25
mma_0224  MS---FTALLAUKSYLRHFWHPVCILKE   25
```

FIG. 3A

```
mma_0224   61-RQAHREAKLSKGCVKQGEAGDRLEQPYEGWQYDKDGACRTIPACPELFIFKKARSDAFEC-120
Cdm        61-RQAFRSAKLSLGTIAN------DRLQPYEGWQYDTBGACKLVPACPNSPIPNRAKVQREDC 116 mma_0224  121-EVRYDIWVRLDASFGVTEIPVESDWEEGMRVIVVDSYWQTTAERRWENFTDFSHFAF-180
Cdm       117-EERYGLIWVRLDSSYACTBIPYFSAASDPKLRVVIQEPYWNATAERRWENFTDFSHFAF-176 mma_0224  181-VHPGTLYDAAYARPPLAPVSRVGGEMRFSIEPPKEMTDQLPDDCPIGAFIYRCTMPYTIN-240
Cdm       177-IHPGTLFDPNNAEPPIVPMDRFNGQERFVYDTPEDMA----VPDQAPIGSFSYTCSMPFAIN-234
```

FIG. 3B

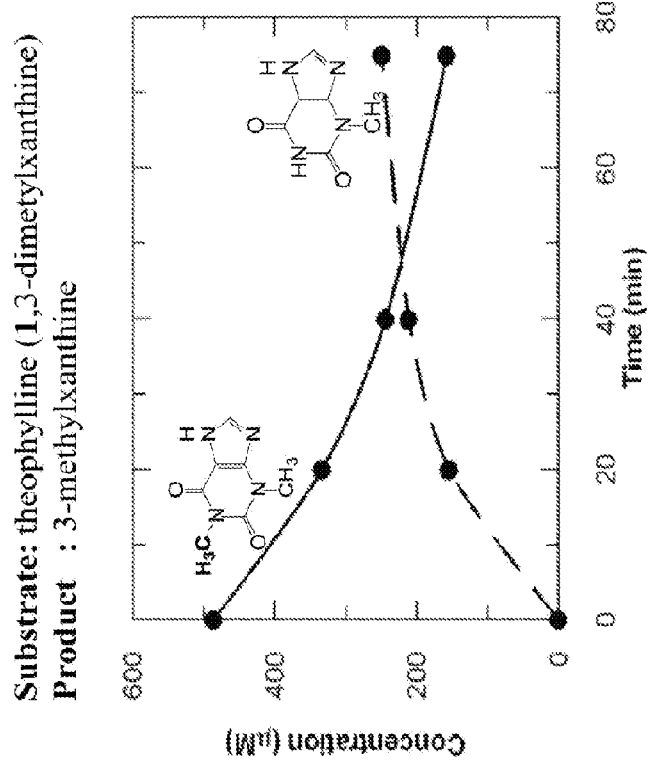
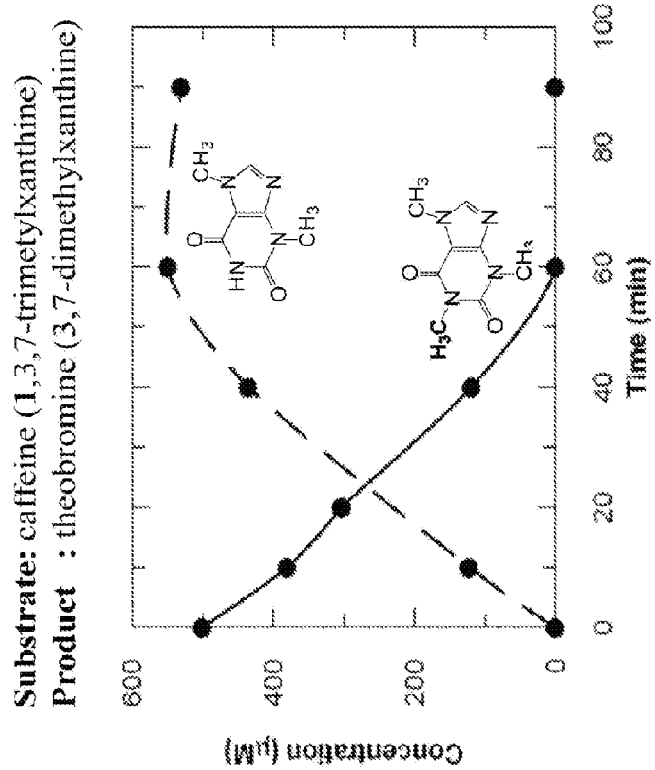
FIG. 7D

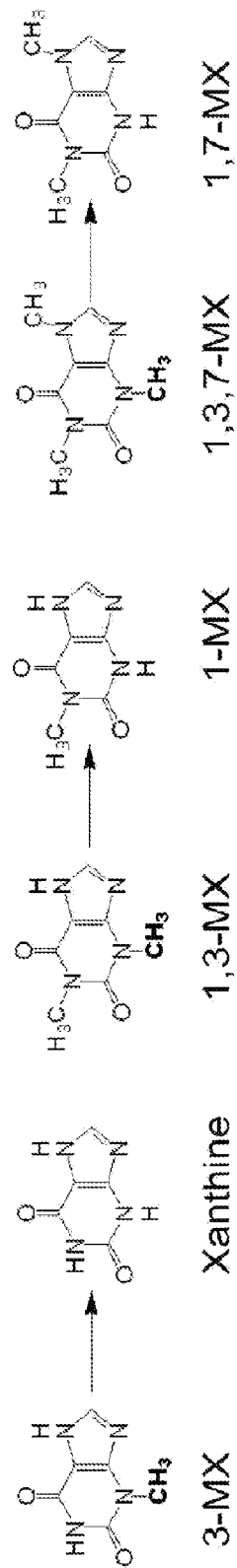
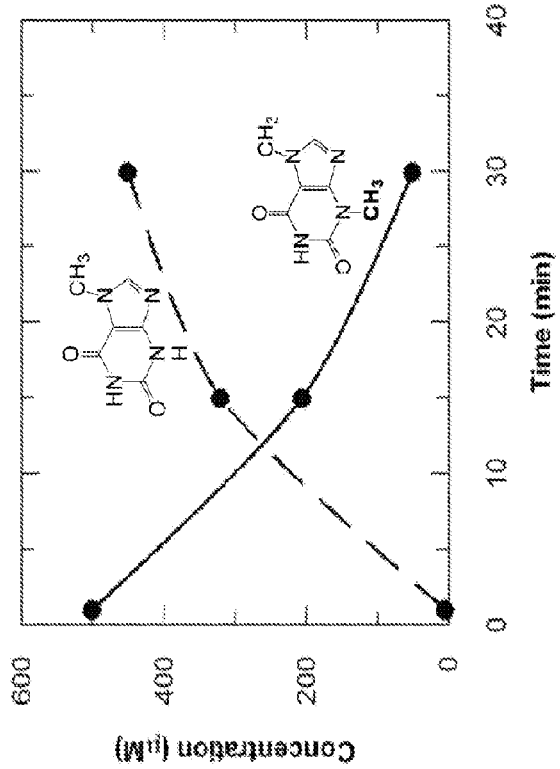
FIG. 7E

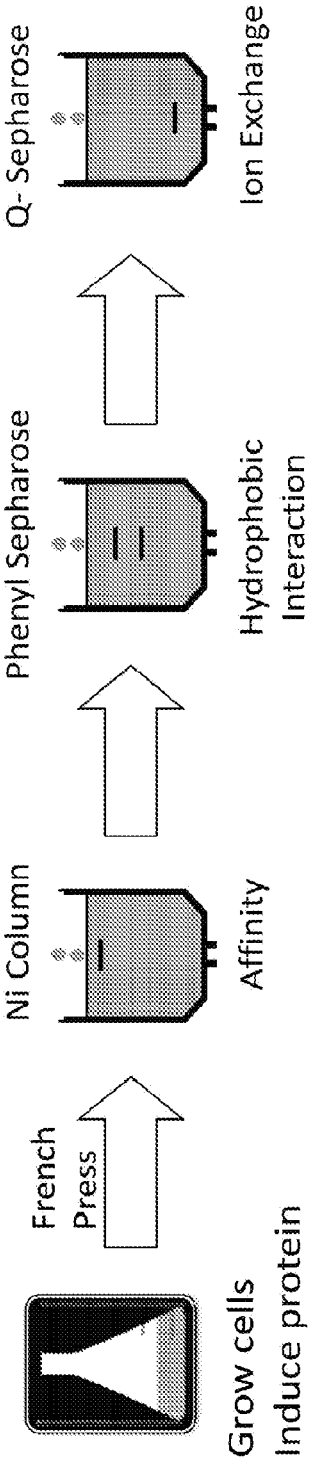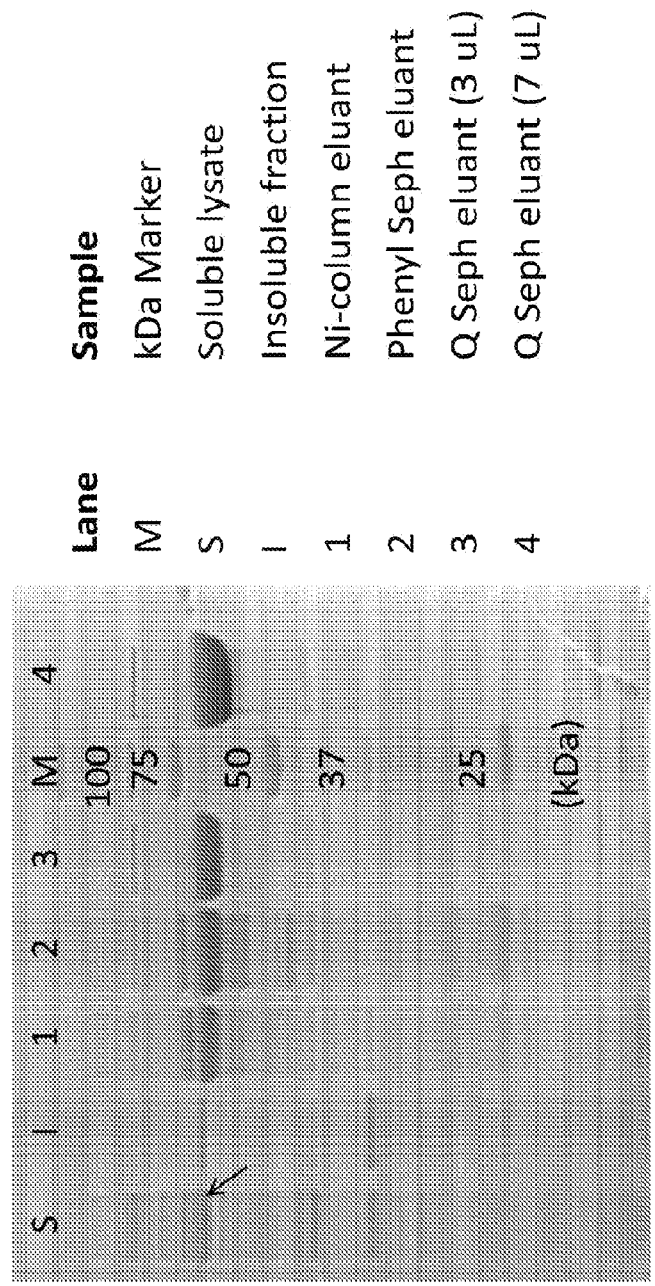
FIG. 14B

N-DEMETHYASE GENES AND USES THEREOF

CROSS-REFERENCE TO RELATED APPLICATIONS

This application is a U.S. National Stage Filing under 35 U.S.C. 371 from International Application No. PCT/US2012/060894, filed on 18 Oct. 2012, and published as WO 2013/059507 A1 on 25 Apr. 2013, which application claims the benefit of the filing date of U.S. application Ser. No. 61/549,339, filed on Oct. 20, 2011, which applications and publications are incorporated by reference herein.

BACKGROUND

Caffeine (1,3,7-trimethylxanthine) and related methylxanthines are widely distributed in many plant species. Caffeine is also a major human dietary ingredient that can be found in common beverages and food products, such as coffee, tea, and chocolates. In pharmaceuticals, caffeine is used generally as a cardiac, neurological, and respiratory stimulant, as well as a diuretic (Dash et al., 2006). Hence, caffeine and related methylxanthines enter soil and water easily through decomposed plant materials and other means, such as effluents from coffee- and tea-processing facilities. Therefore, it is not surprising that microorganisms capable of degrading caffeine have been isolated from various natural environments, with or without enrichment procedures (Dash et al., 2006; Mazzafera, 2004). Bacteria use oxidative and N-demethylating pathways for catabolism of caffeine. Oxidation of caffeine by a *Rhodococcus* sp.-*Klebsiella* sp. mixed-culture consortium at the C-8 position to form 1,3,7-trimethyluric acid (TMU) has been reported (Madyastha and Sridnar, 1995). An 85-kDa, flavin-containing caffeine oxidase was purified from this consortium (Madyastha et al., 1996). Also, Mohapatra et al. (2006) purified a 65-kDa caffeine oxidase from *Alcaligenes* sp. Strain CF8. Cells of a caffeine-degrading *Pseudomonas putida* strain (ATCC 700097) isolated from domestic wastewater (Aganseitan, 2002) showed a fourfold increase in a cytochrome P450 absorption spectrum signal compared to cells grown on glucose. Recently, we reported a novel non-NAD(P)+-dependent heterotrimeric caffeine dehydrogenase from *Pseudomonas* sp. strain CBBI (Yu et al., 2008). This enzyme oxidized caffeine to TMU stoichiometrically and hydrolytically, without producing hydrogen peroxide. Further metabolism of TMU has not been elucidated.

Several caffeine-degrading bacteria metabolize caffeine via the N-demethylating pathway and produce theobromine (3,7-dimethylxanthine) or paraxanthine (1,7-dimethylxanthine) as the initial product. Theophylline (1,3-dimethylxanthine) has not been reported to be a metabolite in bacterial degradation of caffeine. Subsequent N-demethylation of theobromine or paraxanthine to xanthine is via 7-methylxanthine. Xanthine is further oxidized to uric acid by xanthine dehydrogenase/oxidase (Dash et al., 2006; Mazzafera, 2004). Although the identities of metabolites and the sequence of metabolite formation for caffeine N-demethylation are well established, there is very little information on the number and nature of N-demethylases involved in this pathway.

SUMMARY OF THE INVENTION

*Pseudomonas putida* CBB5 is capable of growing on caffeine as the sole carbon and nitrogen source, and degrades both caffeine and theophylline via sequential N-demethylation. The N-demethylase enzymes responsible for this metabolism were purified and biochemically characterized. The holoenzyme included a reductase component with cytochrome reductase activity (Ccr) and a soluble, 2 subunit N-demethylase (Ndm) that demethylates caffeine to xanthine, with a native molecular mass of 240,000 Da. The two subunits of Ndm, designated as NdmA and NdmB, displayed apparent Mr of 40 and 35 kDa, respectively. Ccr transfers reducing equivalents from NAD(P)H to Ndm, and the NAD(P)H-dependent reaction only occurs when the reductase component couples with Ndm and Ndm consumes one molecule of oxygen per methyl group that is removed from caffeine as formaldehyde. Paraxanthine and 7-methylxanthine were determined to be substrates with apparent $K_M$ and $k_{cat}$ values of 50.4±6.8 µM and 16.2±0.6 $min^{-1}$ and 63.8±7.5 µM and 94.8±3.0 $min^{-1}$, respectively. Ndm also displayed activity towards caffeine, theobromine, theophylline, and 3-methylxanthine, all of which are growth substrates for this organism. Ndm was deduced as a Rieske [2Fe-2S] domain-containing non-heme iron oxygenase based on N-terminal sequencing, UV absorbance spectrum, and iron content.

N-demethylase genes were isolated from a genomic DNA library of *Pseudomonas putida* CBB5 using a nested PCR approach, and were cloned individually into an expression vector as C-terminal His-tagged fusion proteins. The gene sequences of NdmA and NdmB were most similar to the catalytic subunits of other Rieske oxygenases known to cleave C—O and C—N bonds. The *E. coli* expressed proteins were purified using a Ni-NTA column. Upon expression of the cloned Ndm genes, NdmA-His alone plus partially purified reductase was capable of N-demethylating caffeine to theobromine (TB) and was determined to be highly specific for the N-1 methyl group. In contrast, NdmB-His alone plus reductase was highly specific for N-3 methyl group, producing paraxanthine (PX) from caffeine. NdmA and B, which were not separable via purification from the wild-type, were fully resolved by genetic approach. Thus, two positional-specific N-demethylases were purified from *P. putida* CBB5 and the corresponding genes encoding Rieske, non-heme iron oxygenases with position specific N-demethylase activity were cloned.

Two other Ndm genes, NdmC and NdmD, which are similarly involved in the degradation of caffeine were also cloned. NdmA, B and C each in combination with NdmD, catalyze the N-demethylation of caffeine at 1-, 3- and 7-positions, respectively. One other Ndm gene, NdmE, is needed for caffeine degradation to xanthine (e.g., for converting 7-methylxantine to xanthine). These genes or their gene products, e.g., a recombinant host cell having one or more of the genes or one or more isolated recombinant enzymes, can be used to convert caffeine, an inexpensive starting material, or related compounds to high value methylxanthines such as mono- or dimethyl-xanthines, or for the production of other chemicals. Further, the genes can be used for converting coffee and tea waste or other agricultural waste having caffeine and other related purine alkaloids to animal feed or biofuel. Because caffeine is an indicator of pollution via human activity, the genes can be used to detect caffeine in the field, e.g., in waste water. In addition, these genes may be employed to detect caffeine in physiological samples, e.g., in nursing mother's milk. The genes can also be used for detection of caffeine in formulations such as drugs, pharmaceutical products, nutraceuticals and beverages, many of which contain caffeine.

Chemicals such as methylxanthines are of high value, both as laboratory chemicals as well as starting materials for production of pharmaceuticals. Currently, they are produced via chemical synthesis, which is a multi-step and expensive process. Use of the genes disclosed herein would provide a biological approach for production of methylxanthines and other related compounds.

BRIEF DESCRIPTION OF FIGURES

FIG. 3. (A) Multiple sequence alignment of the N-terminal protein sequences of NdmA (SEQ ID NO: 3) and NdmB (SEQ ID NO: 4) with the first 25 amino acid residues of caffeine demethylase (Cdm) of P. putida IF-3 (SEQ ID NO: 70) and the hypothetical protein mma 0224 in Janthinobacterium sp. Marseille (SEQ ID NO: 71). (B) Consensus sequences of the Rieske [2Fe-2S] domain (CXHX$_{16}$CX$_2$H, highlighted in black) and the mononuclear ferrous iron domain [(D/E)X$_3$DX$_2$HX$_4$H, highlighted in grey] are identified in Cdm (SEQ ID NO: 73) and mma 0224 (SEQ ID NO:72).

DETAILED DESCRIPTION OF THE INVENTION

Definitions

Figure 1:
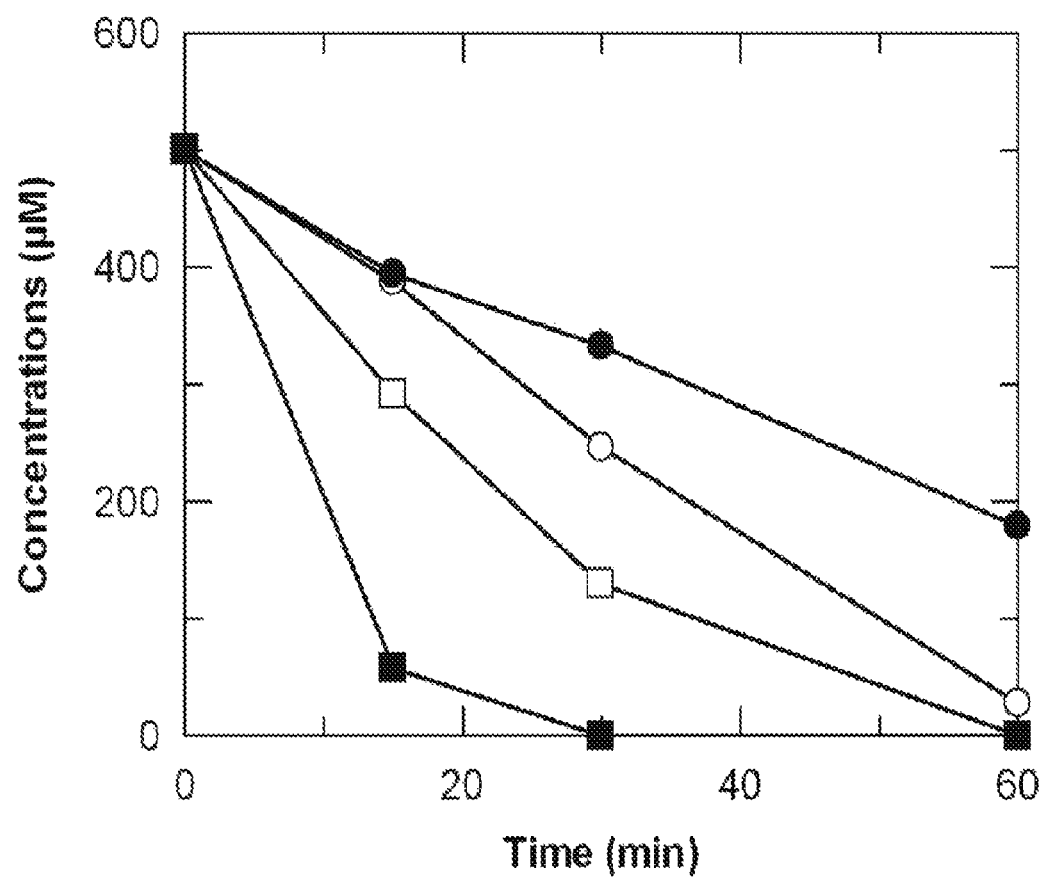
FIG. 1. Degradation of paraxanthine (■), theobromine (□), caffeine (○), and theophylline (●) by cell extracts prepared from P. putida CBB5 grown in soytone supplemented M9-caffeine medium. All reactions contained 0.5 mM of substrate, 0.5 mM NADH, and 7.2 mg ml$^{-1}$ protein. This experiment was repeated three times and similar patterns were observed in all replicates.

As used herein, the term "isolated" refers to in vitro preparation and/or isolation of a nucleic acid molecule, e.g., vector or plasmid, or peptide or polypeptide (protein) so that it is not associated with in vivo substances, or is substantially purified from in vitro substances. Thus, an "isolated oligonucleotide", "isolated polynucleotide", "isolated protein", or "isolated polypeptide" refers to a nucleic acid or amino acid sequence that is identified and separated from at least one contaminant with which it is ordinarily associated in its source. For example, an isolated nucleic acid or isolated polypeptide may be present in a form or setting that is different from that in which it is found in nature. In contrast, non-isolated nucleic acids (e.g., DNA and RNA) or non-isolated polypeptides (e.g., proteins and enzymes) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., a single-stranded nucleic acid), but may contain both the sense and anti-sense strands (i.e., a double-stranded nucleic acid).

The term "nucleic acid molecule," "polynucleotide" or "nucleic acid sequence" as used herein, refers to nucleic acid, DNA or RNA that comprises coding sequences necessary for the production of a polypeptide or protein precursor. The encoded polypeptide may be a full-length polypeptide, a fragment thereof (less than full-length), or a fusion of either the full-length polypeptide or fragment thereof with another polypeptide, yielding a fusion polypeptide.

By "peptide," "protein" and "polypeptide" is meant any chain of amino acids, regardless of length or post-translational modification (e.g., glycosylation or phosphorylation). The nucleic acid molecules of the invention encode a variant of a naturally-occurring protein or polypeptide fragment thereof, which has an amino acid sequence that is at least 60%, e.g., at least 65%, 70%, 75%, 80%, 85%, 90%, 95%, 96%, 97%, 98%, or 99%, but less than 100%, amino acid sequence identity to the amino acid sequence of the naturally-occurring (native or wild-type) protein from which it is derived. The polypeptides of the invention thus include those with conservation substitutions, e.g., relative to the polypeptide encoded by SEQ ID NO:37, SEQ ID NO:38, SEQ ID NO:39, SEQ ID NO:43, or SEQ ID NO:45 and/or a polypeptide with at least 60%, e.g., at least 65%, 70%, 75%, 80%, 85%, 90%, 95%, 96%, 97%, 98%, or 99%, but less than 100%, amino acid sequence identity to a polypeptide encoded by SEQ ID NO:37, SEQ ID NO:38, SEQ ID NO:39, SEQ ID NO:43, or SEQ ID NO:45. Amino acid residues may be those in the L-configuration, the D-configuration or normaturally occurring amino acids such as norleucine, L-ethionine, β-2-thienylalanine, 5-methyltryptophan norvaline, L-canavanine, p-fluorophenylalanine, p-(4-hydroxybenzoyl)phenylalanine, 2-keto-4-(methylthio)butyric acid, beta-hydroxy leucine, gamma-chloronorvaline, gamma-methyl D-leucine, beta-D-L hydroxyleucine, 2-amino-3-chlorobutyric acid, N-methyl-D-valine, 3,4,difluoro-L-phenylalanine, 5,5,5-trifluoro-leucine, 4,4,4,-trifluoro-L-valine, 5-fluoro-L-tryptophan, 4-azido-L-phenylalanine, 4-benzyl-L-phenylalanine, thiaproline, 5,5,5-trifluoroleucine, 5,5,5,5',5',5'-hexafluoroleucine, 2-amino-4-methyl-4-pentenoic acid, 2-amino-3,3,3-trifluoro-methylpentanoic acid, 2-amino-3-methyl-5,5,5-trifluoropentanoic acid, 2-amino-3-methyl-4-pentenoic acid, trifluorovaline, hexafluorovaline, homocysteine, hydroxylysine, ornithine, and those with peptide linkages optionally replaced by a linkage such as, —$CH_2NH$—, —$CH_2S$—, —$CH_2$—$CH_2$—, —CH=CH—(cis and trans), —$COCH_2$—, —$CH(OH)CH_2$—, and —$CH_2SO$—, by methods known in the art. In keeping with standard polypeptide nomenclature, abbreviations for naturally occurring amino acid residues are as shown in the following Table of Correspondence.

| TABLE OF CORRESPONDENCE | | |
|---|---|---|
| 1-Letter | 3-Letter | AMINO ACID |
| Y | Tyr | L-tyrosine |
| G | Gly | L-glycine |
| F | Phe | L-phenylalanine |
| M | Met | L-methionine |

-continued

TABLE OF CORRESPONDENCE

| 1-Letter | 3-Letter | AMINO ACID |
|---|---|---|
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "fusion polypeptide" or "fusion protein" refers to a chimeric protein containing a reference protein (e.g., luciferase) joined at the N- and/or C-terminus to one or more heterologous sequences (e.g., a non-luciferase polypeptide).

Protein primary structure (primary sequence, peptide sequence, protein sequence) is the sequence of amino acids. It is generally reported starting from the amino-terminal (N) end to the carboxyl-terminal (C) end. Protein secondary structure can be described as the local conformation of the peptide chain, independent of the rest of the protein. There are 'regular' secondary structure elements (e.g., helices, sheets or strands) that are generally stabilized by hydrogen bond interactions between the backbone atoms of the participating residues, and 'irregular' secondary structure elements (e.g., turns, bends, loops, coils, disordered or unstructured segments). Protein secondary structure can be predicted with different methods/programs, e.g., PSIPRED (McGuffin et al. (2000), PORTER (Pollastri et al. (2005), DSC (King and Sternberg (1996)), see www.expasy.org/tools/#secondary for a list. Protein tertiary structure is the global three-dimensional (3D) structure of the peptide chain. It is described by atomic positions in three-dimensional space, and it may involve interactions between groups that are distant in primary structure. Protein tertiary structures are classified into folds, which are specific three-dimensional arrangements of secondary structure elements. Sometimes there is no discernable sequence similarity between proteins that have the same fold.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

The term "homology" refers to a degree of complementarity between two or more sequences. There may be partial homology or complete homology (i.e., identity). Homology is often measured using sequence analysis software (e.g., "GCG" and "Seqweb" Sequence Analysis Software Package formerly sold by the Genetics Computer Group, University of Wisconsin Biotechnology Center. 1710 University Avenue, Madison, Wis. 53705). Such software matches similar sequences by assigning degrees of homology to various substitutions, deletions, insertions, and other modifications.

Metabolism of Caffeine

Caffeine and related purine alkaloid theobromine are consumed extensively in the form of coffee, tea, other beverages, and chocolates. Caffeine, a well-known stimulator of the central nervous system, is also used as a medicine to reduce fatigue and increase alertness. It is a common ingredient in pharmaceuticals, weight-loss products and energy-drinks. Thus, caffeine is ubiquitously released into the environment, including from coffee and tea-processing factories. Hence, it is not surprising that several microorganisms, primarily *Pseudomonas*, have been shown to utilize caffeine for growth. The most prevalent pathway for bacterial degradation of caffeine is via a series of N-demethylations. The initial metabolites are paraxanthine and theobromine, which are converted to 7-methylxanthine and to xanthine. Theophylline, which is not an intermediate in this pathway, is also metabolized via N-demethylation to 3- and 1-methylxanthine to xanthine. The number and nature of N-demethylases involved is not known. Caffeine is also metabolized via 8-oxidation to trimethyluric acid (TMU) and then to trimethylallantoin (TMA). Conversion of TMU to TMA, and further degradation of TMA have not been elucidated. Caffeine to TMU in *Pseudomonas* CBB1 is catalyzed by a novel quinone-dependent caffeine dehydrogenase (Cdh). This enzyme has a native molecular weight of 158 KDa and is a αβγ heterotrimer with subunits sizes of 90, 40 and 19 KDa. The genes encoding the three subunits, cdhA, cdhB and cdhC have been sequenced (accession HM053473). Cdh is a new member of the molybdenum-containing-hydroxylase family of proteins, which include xanthine dehydrogenase and oxidase. They have molybdopterin, FAD, and [2Fe-2S] cluster as cofactors, and incorporate an oxygen atom from water into the product. Two caffeine oxidases, a 85 KDa from *Rhodococcus* sp. I*Klebsiella* sp. mixed-culture, and a 65 KDa from *Alcaligenes* sp. CF8 have also been implicated in the conversion of caffeine to TMU. Both are monomeric flavoproteins. Caffeine-degrading bacteria have several potential applications including remediation of waste from coffee/tea processing plants, and production of high-value alkylxanthines. Caffeine dehydrogenase from CBB1 has all the attributes towards developing a semi-quantitative rapid diagnostic 'dipstick' test for detection of caffeine in breast-milk and environmental samples.

Caffeine and related purine alkaloids have been widely consumed over thousands of years as food ingredients. Caffeine (1,3,7-trimethylxanthine) is a purine alkaloid found in more than 60 plant species. It is present in high concentrations, ranging from 2 to 6% in coffee, tea, cocoa and Cola nuts. Today, many of the beverages we consume contain caffeine in the concentration range of 5 to 230 mg per serving.

Caffeine is a central nervous system and metabolic stimulant (Mazzafera, 2002). It is used both recreationally and medically to reduce physical fatigue and restore mental alertness when unusual weakness or drowsiness occurs. Caffeine and other methylxanthine derivatives are also used on newborns to treat apnea and correct irregular heartbeats. Caffeine stimulates the central nervous system first at higher levels, resulting in increased alertness and wakefulness, faster and clearer flow of thought, increased focus, and better general body coordination. Because of its various physiological effects, caffeine is widely distributed in pharmaceutical preparations and a variety of supplements such as weight loss and energy drinks. In addition other studies have shown that caffeine can be a potential contributor to reducing risk factors involved in the metabolic syndrome, including type 2 diabetes, obesity (Westerterp-Plantenga et al., 2006), Parkinson disease and various cancers. Caffeine is also added as a general stimulant in various drug formulations. Other two related purine alkaloids related to coffee, regularly consumed by humans are theophylline (1,3-dimethylxanthine) and theobromine (3,7-dimethylxanthine). Even though Caffeine, theophylline and theobromine are structurally similar they have different physiological effects. For example, theophylline is used as a bronchial-dilator and theobromine as a diuretic (Asano et al., 1993).

In spite of caffeine being such a ubiquitous natural product in the environment, microbial transformation of caffeine did not receive much attention till early 1970's. This is partly due to its mutagenic effect through inhibition of DNA repair in bacteria. At 0.1% concentration caffeine also inhibits protein synthesis in bacteria and yeast. Caffeine is toxic to most bacteria especially at concentrations higher than 0.4% (Ramanaviciene et al., 2003) but is likely toxic to most bacteria even at concentrations as low as 0.1%. Thus, very few microorganisms are known to mineralize caffeine and related analogs. Those capable of metabolism of caffeine have been mostly isolated from plantation soil or caffeine-contaminated sites. The microbial transformation pathways of caffeine are different in different in microbes, reflecting the complexity in genes and enzymes involved.

Metabolism of Caffeine and Related Methylxanthines in Bacteria

There are several reports on the use of purine alkaloids, including caffeine as a source of energy for the growth of microorganisms. Dikstein et al. (1957) studied the degradation of 3-methyl xanthine mediated by dehydrogenase activity in *Pseudomonas fluorescens*. This enzyme was not active on 1-methyl xanthine. In contrast, Woolfolk (1975) demonstrated dehydrogenase activity against both 1- and 3-methyl xanthines using a *P. fluorescens* strain grown on caffeine. This report suggested that N-demethylases degraded caffeine sequentially, removing all the three methyl groups resulting in the formation of xanthine. Xanthine is further degraded by the well known purine degradative pathway (Vogels et al., 1976). Methanol formed from N-demethylation of caffeine is further oxidized to carbon dioxide via formaldehyde and formate dehydrogenases, which are induced by growth on caffeine. Blecher (1976) also studied caffeine degradation by growing *Pseudomonas putida* under anaerobic conditions and with sole source of carbon and nitrogen. The breakdown of caffeine in this organism also begins with stepwise N-demethylation, which leads to the formation of formaldehyde and xanthine. In a separate study, Blecher et al. (1977) isolated several bacterial strains by enriching humus soil with caffeine and incubating at 30° C. for 6 months. The soil was then transferred to a media containing caffeine and ammonium sulfate. This procedure yielded only *Pseudomonas putida*, which also degraded caffeine by partial N-demethylation giving rise to 3,7-dimethylxanthine (theobromine) and 1,7-dimethylxanthine (paraxanthine). These were further N-demethylated to 7-methylxanthine and xanthine. The authors also noticed that 3,7-dimethyl xanthine, 1, 7-dimethyl xanthine and 7-methylxanthine were oxidized at the 8-position to form corresponding methyluric acids.

Middelhoven and Bakker (1982) also isolated a *P. putida* strain capable of growth on caffeine as the sole source of carbon and nitrogen. Their study suggested that caffeine degradation was probably mediated by monooxygenases, but details of the pathway were not elucidated. A strain of *P. putida* isolated by Yamaoka-Yano et al. (1998) showed an impressive ability to grow in caffeine as high as 25 g/L. Later, the same group (Yamaoka-Yano et al. 1999) reported caffeine degradation in this isolate via N-demethylation, which was in agreement with the finding of Blecher et al. (1977). Yu et al. (2009) isolated a strain of *Pseudomonas putida* CBB5 by enrichment on caffeine which elaborated two distinct pathways for the metabolism of caffeine and theophylline. This strain used not only caffeine, theobromine, paraxanthine and 7-methylxanthine as sole source of carbon and nitrogen but also used theophylline and 3-methylxanthine. Caffeine degradation was initiated by N-demethylation giving rise to theobromine and paraxanthine, which were further N-demethylated to 7-methylxanthine. Similarly, theophylline was degraded by N-demethylation yielding 3-methylxanthine and 1-methylxanthine, which were further N-demethylated to xanthine. Theophylline was also shown to be oxidized to 1,3-dimethyl and 1- and 3-methyluric acids. However, these methyluric acids were not metabolized further. Both caffeine and theophylline N-demethylation pathways were co-expressed in *Pseudomonas putida* CBB5. Xanthine is further oxidized via the well known pathway to glyoxalic acid and urea (Vogels et al., 1976).

Caffeine Degradation by Oxidative Pathway

There are a few well-studied reports on caffeine degradation by an alternate oxidative pathway. Madyastha et al. (1998) reported caffeine degradation by a mixed culture consortium consisting of *Klebsiella* and *Rhodococcus* sp. via C-8 oxidation resulting in the formation of 1,3,7-trimethyluric acid (TMU). This compound was further metabolized to 3,6,8-trimethyl allantoin (TMA). Similarly Yu et al., (2008) isolated *Pseudomonas* sp. CBB1 by enrichment of soil with caffeine as sole source of carbon and nitrogen. CBB1 was also shown to initiate caffeine degradation via 1,3,7-trimethyl uric acid.

Caffeine Degradation in Fungal and Yeast Systems

Caffeine metabolism in fungal systems is via a different sequence of N-demethylations. Ina et al. (1971) investigated caffeine degradation by *Aspergillus niger* capable of utilizing this compound as sole source of carbon and nitrogen. The degradation was initiated by N-demethylation yielding theophylline and 3-methylxanthine. Schwimmer et al. (1971) studied the metabolism of caffeine by *Pencillium roqueforti*, a strain isolated on caffeine as sole source of nitrogen. Here too, degradation was initiated by N-7 demethylation resulting in the formation of theophylline. The nature of enzymes involved in fungal N-demethylation reactions is not known. However, Sauer et al. (1982) showed that caffeine degradation in yeast was initiated by cytochrome P450, similar to that in animals.

Enzymology of Caffeine Oxidation

A number of different enzymes have been reported to catalyze the oxidation of caffeine to TMU. An 85-kDa, flavin-containing caffeine oxidase was purified from *Rhodococcus* sp. I*Klebsiella* sp. mixed culture consortium (Madyastha et al., 1999). This enzyme showed broad-substrate specificity towards caffeine and various alkylxanthine analogues. Although the *Rhodococcus* sp./*Klebsiella* sp. consortium initiated caffeine oxidation at the C-8 position and TMU was identified as a metabolite (Madyastha et al., 1998), stoichiometry of the reaction, including the formation of hydrogen peroxide was not established. In addition, oxygen was a poor electron acceptor for this enzyme, since caffeine oxidase activity decreased 10-fold when cytochrome c or dichlorophenol indophenol (DCPIP) was replaced by oxygen as electron acceptor. So, it is unclear whether this enzyme really metabolizes caffeine by an oxidase mechanism. Another 65-kDa caffeine oxidase was purified from *Alcaligenes* sp. CF8 (Mohapatra et al., 2006). Caffeine was the best substrate for this enzyme but it also had low activity on theophylline and theobromine. Also, DCPIP was the preferred electron acceptor in vitro for this enzyme. Although production of hydrogen peroxide was reported, oxygen was a poor electron acceptor for this enzyme because the specific activity of the enzyme was 8 times higher when DCPIP was used as an electron acceptor. Finally, TMU was not confirmed as a reaction product of this caffeine oxidase.

Recently, a caffeine dehydrogenase (Cdh) was purified from *Pseudomonas* sp. strain CBB1 (Yu et al., 2008). The purified enzyme had a molecular mass of 158 kDa and consisted of three non-identical subunits with molecular masses of 90, 40 and 19 kDa, suggesting Cdh is a heterotrimer with a αβγ structure. This subunit structure differs from monomeric caffeine oxidases from *Alcaligenes* sp. CF8 and *Rhodococcus* sp./*Klebsiella* sp. mixed culture consortium (Madyastha et al., 1999 and Mohapatra et al., 2006), but it is similar to several bacterial xanthine dehydrogenases (Schrader et al., 1999 and Schultz et al., 2001). Cdh oxidized caffeine to 1,3,7-trimethyluric acid stoichiometrically, without producing hydrogen peroxide. Neither $NAD(P)^+$ nor oxygen functions as electron acceptor for Cdh; instead coenzyme $Q_0$ is the preferred electron acceptor in vitro. Cdh incorporated an oxygen atom derived from water into TMU. This enzyme is completely different from the two reported caffeine oxidases. In addition, substrate specificity study showed that Cdh was specific for caffeine and theobromine but had only 5% activity theophylline and none on xanthine. The UV/visible absorbance spectrum of purified Cdh showed an absorption maximum at 278 nm with broad double peak at around 360 and 450 nm. These spectral properties are characteristic for enzymes containing FAD and iron-sulfur clusters, and are similar to those of xanthine dehydrogenases (Schrader et al., 1999 and Leimkuhler et al., 2003). Furthermore, the subunit structure, the subunit molecular weights, and the ability to utilize water as the source of oxygen atom incorporated into the product are properties similar to those of xanthine dehydrogenases. However, xantine dehydrogenase is NAD $(P)^+$-dependent. Table 1 compares the properties of caffeine oxidases, caffeine dehydrogenase, xanthine dehydrogenase and aldehyde oxidase.

NO:2), respectively. Forward and reverse degenerate PCR primers were designed from the N-terminal protein sequences of 90- and 40-subunits, respectively. Using the degenerate PCR primers, gene encoding the 90-kDa subunit of Cdh, designated as cdhA, was successfully amplified from CBB1 genomic DNA. This result suggested cdhA was directly upstream to the gene encoding the 40-kDa subunit. The gene cdhA was used as a probe to screen a fosmid library prepared from genomic DNA of CBB1. One of the clones in the genomic DNA library, clone 848, was found to contain cdhA. Direct DNA sequencing of clone 848 using sequencing primer designed from cdhA, identified 2 ORFs directly 3' to cdhA. The first ORF, cdhB, was 888-bp in size. The deduced protein sequence of cdhB had, an N-terminus completely identical to that of the 40-kDa subunit of Cdh, indicating cdhB is the gene encoding the 40-kDa subunit (unpublished results). The second ORF 3' to cdhA was 528-bp in size and encoded an 18.4-kDa protein, matching the size of the 19-kDa subunit of Cdh. This ORF was designated as cdhC (unpublished results). ABLASTP (Altschul et al., 1997) search of the GenBank database revealed that the deduced protein sequences of cdhA, cdhB, and cdhC were highly homologous to proteins that belong to the molybdenum-containing hydroxylase family (Table 2). Members of this group of hydroxylase, including xanthine dehydrogenase/oxidase, have molybdopterin, FAD, and [2Fe-2S] cluster as cofactors and incorporate an oxygen atom derived from water into the product (Fetzner et al., 2000 and Hille et al., 2005). The oxygen in trimethyluric acid produced by Cdh also originated from water (Yu et al., 2008). CdhA is predicted to be the molybdopterin-binding catalytic subunit of Cdh. Residues and motifs that are conserved among Mo-containing hydroxylases for interacting with the Mo-cofactor are identified in CdhA. CdhB displayed high degree of homology to FAD-binding domain of molybdopterin dehydrogenase (Pf00941). Two conserved FAD-interacting motifs were also identified in CdhB. Finally, CdhC has two conserved [2Fe-2S] binding domains (PF00111 at N-terminus & PF01799 at C-terminus). Like other molybdenum-containing hydroxy-

TABLE 1

Properties of Caffeine dehydrogenase and related oxidases.

| Properties | Caffeine Oxidase | Caffeine Oxidase | Caffeine Dehydrogenase | Xanthine Oxidase/ Dehydrogenase | Aldehyde Oxidase |
|---|---|---|---|---|---|
| M. W. (kDa) | 85 | 65 | 158 | 290 | 132 |
| Subunit M.W. (kDa) | — | — | α: 90 (85.9), β: 34 (32.5), γ: 20 (18.4) | α: 85, β: 40, γ: 20 | α: 88, β: 39, γ: 18 |
| Subunit Structure | Monomer | Monomer | Hetero Monomer | Hetero Dimer | Hetero Monomer |
| Absorbance Spectra, $\lambda_{max,nm}$ | N/A | N/A | 360, 450 | 360, 450 | 365, 450 |
| Cofactors | N/A | N/A | Not determined | Moco, $Fe_2S_2$, FAD | Moco, $Fe_2S_2$, FAD |
| Electron Acceptors | Cyt, C, $O_2$ | DCPIP, $O_2$ | Coenzyme $Q_o$ | $O_2$, NAD(P) | $O_2$ |
| Substrates | Caffeine | Caffeine | Caffeine | Xanthine | Aldehydes |
| Product | TMU | N/A | TMU | Uric acid | |
| Gene Designation | N/A | N/A | cdhABC | xdhABC | N/A |
| N-terminal amino acid | N/A | N/A | α: MFADINKGDAF (SEQ ID NO: 78) β: MKLPTAFDYIR (SEQ ID NO: 79) γ: Unknown | α: EDTVGRPLPHL (SEQ ID NO: 80) β: KDVPPKQLRFE (SEQ ID NO: 81) γ: MTADELVFFVN (SEQ ID NO: 82) | α: MNRFGYAKPNA (SEQ ID NO: 83) β: VVHLQKAVPRV (SEQ ID NO: 84) γ: Unknown |

Caffeine Dehydrogenase Genes of *Pseudomonas* sp. CBB1

N-terminal protein sequences of the 90- and 40-kDa subunits of Cdh were determined to be MFADINKGDAFGTX-VGN (SEQ ID NO:1) and MKPTAFDYIRPTSLPE (SEQ ID lase, the N-terminal [2Fe-2S] cluster is of the plant ferredoxin type. All of these data suggest Cdh could be a new member of the molybdenum-containing hydroxylase family and is in agreement with preliminary cofactor analyses of purified Cdh. Gene sequences of cdhABC have been deposited at the GenBank database (accession no. HM053473). Electrons from caffeine transferred to CdhA, are hypothesized to be transported via CdhC to CdhB, and finally to an electron acceptor yet to be identified. In vitro, quinone $Q_0$ is the best electron acceptor for Cdh (Yu et al., 2008). This proposed scheme is similar to other molybdenum-containing hydroxylases.

TABLE 2

Proteins that display significant homology to CBB1 cdhABC gene products.

| CBB1 Protein | Representative homolog (% Identity) | Organism |
|---|---|---|
| CdhA | Putative xanthine dehydrogenase Mo-binding subunit | Sphingomonas wittichii RW1 |
|  | Putative xanthine dehydrogenase/aldehyde oxidase Mo-binding subunit | Roseiflexus castenholzii DSM |
|  | Putative CO dehydrogenase large subunit | Thermomicrobium roseum ATCC27502 |
|  | Quinoline-2-oxidoreudctase | Pseudomonas putida 86 |
|  | NdhL, Nicotine dehydrogenase large subunit | Arthrobacter nicotinovorans |
| CdhB | Putative CO dehydrogenase medium FAD-binding subunit | Thermomicrobium roseum ATCC27502 |
|  | Putative molybdopterin dehydrogenase FAD-binding subunit | Frankia sp. EAN1pec |
|  | KdhM, ketone dehydrogenase medium subunit | Arthrobacter nicotinovorans |
|  | CoxM, CO dehydrogenase medium FAD-binding subunit | Hydrogenophaga pseudoflava |
| CdhC | Putative aldehyde oxidase small subunit | Thermomicrobium roseum ATCC27502 |
|  | Probable 2Fe—2S ferredoxin | Janibacter sp. HTCC2649 |
|  | Putative CO dehydrogenase small subunit | Thermomicrobium roseum ATCC27502 |
|  | CoxS, CO dehydrogenase small Fe—S binding subunit | Hydrogenophaga pseudoflava |

Enzymology of N-demethylation of Methylxanthines in Bacterial Systems

Several members of the genera *Pseudomonas* and a strain of *Serratia marcescens*, were reported to metabolize caffeine via N-demethylation (Woolfolk et al., 1975, Blecher et al., 1977, Asano et al., 1993, Sideso et al., 2001, Yu et al., 2009, Dash et al., 2008 and Mazzafera et al., 1996). In all of these bacteria, N-demethylation of caffeine usually results in the production of either theobromine or paraxanthine. Paraxanthine and theobromine are then N-demethylated to 7-methylxanthine, which is further N-demethylated to xanthine. Theophylline, a natural dimethylxanthine, is not utilized by *Serratia marcescens* and has not been reported as a bacterial metabolite of caffeine. A caffeine-degrading bacterium, *Pseudomonas putida* CBB5, was recently isolated from soil by enrichment with caffeine as the sole source of carbon and nitrogen (Yu et al., 2009). This bacterium metabolizes caffeine via a pathway similar to other caffeine-degrading *Pseudomonas*. Caffeine is sequentially N-demethylated to paraxanthine and theobromine, 7-methylxanthine, and xanthine. CBB5 utilizes a previously unknown pathway for N-demethylation of theophylline via 1- and 3-methylxanthines, to xanthine. While caffeine and theophylline degradation pathways were co-expressed in the presence of caffeine, theophylline, and related methylxanthines, the intermediate metabolites of the two pathways do not overlap until xanthine (Yu et al., 2009), which enters the normal purine catabolic pathway via uric acid.

Despite several studies of metabolism of purine alkaloids via N-demethylation, there is no detailed characterization of the nature and number of N-demethylases involved. Previous attempts to purify caffeine N-demethylase were unsuccessful because of the instability of the enzyme. However, a common characteristic of most of these N-demethylases is that NADH (P)H was required as co-substrates (Mazzafera et al., 2004 and Dash et al., 2006). In *Pseudomonas putida* CBB5, an NAD(P)H-dependent conversion of theophylline to 1- and 3-methylxanthines was also detected in the crude cell extract of theophylline grown CBB5 (Yu et al., 2009). Some indirect experiments by others indicate the presence of specific and multiple N-demethylases involved in the metabolism of caffeine.

Dash et al. (2008) showed that caffeine and theobromine N-demethylases in *Pseudomonas* sp.NCIM5235 were inducible in nature but caffeine N-demethylase activity in theobromine grown cells was 10-fold lower than that of caffeine grown cells. Theobromine was shown to induce only theobromine N-demethylase activity but not caffeine N-demethylase activity. These data implied different N-demethylases were responsible for caffeine and theobromine N-demethylations in *Pseudomonas* sp. NCIM5235. Gluck et al. (1998) partially purified an oxygen- and NAD (P)H-dependent 7-methylxanthine N-demethylase from caffeine-degrading *P. putida* WS. This enzyme was specific for 7-methylxanthine and had no activity towards caffeine, theobromine, or paraxanthine. Caffeine and theobromine also did not inhibit 7-methylxanthine N-demethylation by this enzyme. These results also imply *P. putida* WS had several N-demethylases to metabolize caffeine.

Asano et al. (1994) investigated N-demethylases in caffeine-degrading *P. putida* No. 352. Caffeine N-demethylase activity was detected in the cell extracts of this bacterium, and this activity was oxygen-dependent; formaldehyde was a co-product. After ammonium sulfate fractionation and passing the precipitated proteins through an anion-exchange column, caffeine N-demethylase activity was resolved into three distinct fractions. At the same time, a theobromine N-demethylase activity, which produced 7-methylxanthine from theobromine, was found to co-elute with one of the caffeine N-demethylase fraction. The theobromine N-demethylase activity was inhibited by $Zn^{2+}$ while caffeine N-demethylase activities in all three fractions were not; implying theobromine and caffeine N-demethylase were different enzymes. The theobromine N-demethylase was subsequently purified to homogeneity. It had a native molecular mass of 250 kDa but only appeared as a single 41-kDa band when resolved on SDS-PAGE gel, suggesting that it is a homohexamer. This enzyme was brown in color and its UV/visible absorption spectrum had a maximum absorbance at 415 nm. In *Pseudomonas putida* CBB5, an NAD(P)H-dependent conversion of theophylline to 1- and 3-methylxanthines was detected in the crude cell extracts of theophylline grown CBB5 (Yu et al., 2009).

Uses for Caffeine Catabolic Enzymes

Caffeine degrading microorganisms have great potential for biotechnological application, e.g., decaffeination of coffee and tea; environmental applications such as treating waste waters and soil contaminated with by-products from coffee industry which are mainly caffeine and related xanthines; as a diagnostic tool to detect/measure caffeine in breast milk and other body fluids; and an alternative to chemical synthesis of alkylxanthines and alkyl uric acids.

Decaffeination of Coffee and Tea

Caffeine being a CNS stimulating agent, there is a preference for decaffeinated beverages. Decaffeinated coffee, tea and colas are extensively consumed in North America and Europe. Decaffeination is primarily carried out by extraction with chlorinated solvents or by supercritical carbon dioxide. Extraction of caffeine from coffee seeds with organic solvents, to produce decaffeinated coffee was first demonstrated in 1903 by Roselius et al. (1903). Commercial decaffeination is now a sophisticated process and yields about 99% caffeine free products. However, the decaffeinated materials are not completely free of solvent residues such as dichloromethane used for decaffeination. Supercritical fluid extraction with carbon dioxide is also used in the decaffeination process as an alternative to use of chlorinated solvents, in order to eliminate the potential health concerns posed by solvent residues. However, there is still an interest in green technology for decaffeination of coffee and tea via use of biological methods. Biological alternatives for decaffeination have been considered by Kurtzmann et al. (1971) and Thakur et al. (U.S. Pat. No. 7,141,411). Kurtzmann et al. (1971) reported decaffeination from solution containing caffeine by *Pencillium roqueforti* and a *Stemphylium* sp. They have observed complete disappearance of caffeine from the culture medium of actively growing *Pencillium roqueforti* and *Stemphylium* sp. Thakur et al. (U.S. Pat. No. 7,141,411) demonstrated removal of caffeine by *Pseudomonas putida* from media containing caffeine. However, none of these studies have demonstrated biological decaffeination of coffee or tea extracts, via the use of bacteria and/or appropriate enzymes.

The major drawback in using caffeine degrading whole cells for decaffeination is the release of endotoxins during the process. The final product must be free of endotoxins; even low levels of residual endotoxin will cause illness in humans. This can be overcome by using purified caffeine degrading enzymes in soluble or immobilized forms. Such approaches have not attracted attention due to the prohibitive cost of using purified enzymes from wild-type organisms. If cloning and high level expression of caffeine degrading enzymes can be achieved in a suitable GRAS (Generally Recognized as Safe) organism as *Saccharomyces cerevisiae*, biodecaffeination could be revisited.

Treating Environmental Wastes

While decaffeination by using bacterial whole cells or isolated enzymes has serious limitations, the technology itself is attractive for caffeine-remediation of waste generated from coffee processing plants and other purine alkaloid-contaminated environments. During the processing of coffee cherry, multiple million tons of coffee pulp is generated annually as waste (Brand et al., 2000). The caffeine content of this waste pulp is 1%; hence their use as animal feed is limited in spite of the pulp being rich in carbohydrates and proteins. Also wide-spread, anthropogenic origin of caffeine makes it as a good indicator of human sewage contamination. Caffeine has been useful for tracking anthropogenic inputs in rural freshwater and urban marine systems. It is already an anthropogenic marker for wastewater contamination of surface waters worldwide, and untreated domestic wastewater (Buerge et al., 2006). In all these cases, caffeine degrading bacterial cells or enzymes can be useful in remediation.

Sources of Cells for Recombinant Expression and Methods of Preparation and Use

The invention provides preparations of microbial cells, spray-dried preparations or lysates or crude extracts thereof, suitable for biocatalysis, and a simpler process for using those cells, lysates or crude extracts thereof, in biocatalysis. In one embodiment of the invention, the invention provides for preparations of prokaryotic cells, or lysates or crude extracts thereof, suitable for biocatalysis, and a simpler process for using those cells, lysates or crude extracts thereof, in biocatalysis. In one embodiment, the prokaryotic cells are *E. coli* cells. In another embodiment, the prokaryotic cells are *Pseudomonas* cells.

The invention also provides spray-dried preparations of cells such as yeast cells suitable for biocatalysis and a simpler process for using those cells in biocatalysis. In one embodiment, the present invention provides for a process to spray-dry microbial cells to render them porous and suitable for biocatalysis, without leaching of enzymes for the biocatalysis. Thus, the cells can be used directly for production. Accordingly, the process to take a biocatalyst from the fermentor to the reactor has been simplified by several steps. Spray-drying the cells may also render the enzymes in those cells stable. Also, spray drying results in stable enzymes. Accordingly, the invention provides microbial cells such as yeast cells, e.g., *Pichia* or *Saccharomyces* cells, as well as recombinant microbial cells, such as recombinant *Pichia*, *Pseudomonas* or *E. coli* cells, for the production of various chemicals. The spray-dried cells are easy to prepare, store and use.

Yeast cells useful in the present invention are those from phylum Ascomycota, subphylum *Saccharomycotina*, class *Saccharomycetes*, order Saccharomycetales or Schizosaccharomycetales, family Saccharomycetaceae, genus *Saccharomyces* or *Pichia* (Hansenula), e.g., species: *P. anomola, P. guilliermondiii, P. norvegenesis, P. ohmeri*, and *P. pastoris*. Yeast cells employed in the invention may be native (non-recombinant) cells or recombinant cells, e.g., those which are transformed with exogenous (recombinant) DNA having one or more expression cassettes each with a polynucleotide having a promoter and an open reading frame encoding one or more enzymes useful for biocatalysis. The enzyme(s) encoded by the exogenous DNA is referred to as "recombinant," and that enzyme may be from the same species or heterologous (from a different species). For example, a recombinant *P. pastoris* cell may recombinantly express a *P. pastoris* enzyme or a plant, microbial, e.g., *Aspergillus* or *Saccharomyces*, or mammalian enzyme.

In one embodiment, the microbial cell employed in the methods of the invention is transformed with recombinant DNA, e.g., in a vector. Vectors, plasmids, cosmids, YACs (yeast artificial chromosomes) BACs (bacterial artificial chromosomes) and DNA segments for use in transforming cells will generally comprise DNA encoding an enzyme, as well as other DNA that one desires to introduce into the cells. These DNA constructs can further include elements such as promoters, enhancers, polylinkers, marker or selectable genes, or even regulatory genes, as desired. For instance, one of the DNA segments or genes chosen for cellular introduction will often encode a protein that will be expressed in the resultant transformed (recombinant) cells, such as to result in a screenable or selectable trait and/or that will impart an improved phenotype to the transformed cell. However, this may not always be the case, and the present invention also encompasses transformed cells incorporating non-expressed transgenes.

DNA useful for introduction into cells includes that which has been derived or isolated from any source, that may be subsequently characterized as to structure, size and/or function, chemically altered, and later introduced into cells. An example of DNA "derived" from a source, would be a DNA sequence that is identified as a useful fragment within a given organism, and that is then chemically synthesized in essentially pure form. An example of such DNA "isolated" from a source would be a useful DNA sequence that is excised or removed from said source by biochemical means, e.g., enzymatically, such as by the use of restriction endonucleases, so that it can be further manipulated, e.g., amplified, for use in the invention, by the methodology of genetic engineering. Such DNA is commonly also referred to as "recombinant DNA."

Therefore, useful DNA includes completely synthetic DNA, semi-synthetic DNA, DNA isolated from biological sources, and DNA derived from introduced RNA. The introduced DNA may be or may not be a DNA originally resident in the host cell genotype that is the recipient of the DNA (native or heterologous). It is within the scope of the invention to isolate a gene from a given genotype, and to subsequently introduce multiple copies of the gene into the same genotype, e.g., to enhance production of a given gene product.

The introduced DNA includes, but is not limited to, DNA from genes such as those from bacteria, yeasts, fungi, plants or vertebrates, e.g., mammals. The introduced DNA can include modified or synthetic genes, e.g., "evolved" genes, portions of genes, or chimeric genes, including genes from the same or different genotype. The term "chimeric gene" or "chimeric DNA" is defined as a gene or DNA sequence or segment comprising at least two DNA sequences or segments from species that do not combine DNA under natural conditions, or which DNA sequences or segments are positioned or linked in a manner that does not normally occur in the native genome of the untransformed cell.

The introduced DNA used for transformation herein may be circular or linear, double-stranded or single-stranded. Generally, the DNA is in the form of chimeric DNA, such as plasmid DNA, which can also contain coding regions flanked by regulatory sequences that promote the expression of the recombinant DNA present in the transformed cell. For example, the DNA may include a promoter that is active in a cell that is derived from a source other than that cell, or may utilize a promoter already present in the cell that is the transformation target.

Generally, the introduced DNA will be relatively small, i.e., less than about 30 kb to minimize any susceptibility to physical, chemical, or enzymatic degradation that is known to increase as the size of the DNA increases. The number of proteins, RNA transcripts or mixtures thereof that is introduced into the cell is preferably preselected and defined, e.g., from one to about 5-10 such products of the introduced DNA may be formed.

The selection of an appropriate expression vector will depend upon the host cells. An expression vector can contain, for example, (1) prokaryotic DNA elements coding for a bacterial origin of replication and an antibiotic resistance gene to provide for the amplification and selection of the expression vector in a bacterial host; (2) DNA elements that control initiation of transcription such as a promoter; (3) DNA elements that control the processing of transcripts such as introns, transcription termination/polyadenylation sequence; and (4) a gene of interest that is operatively linked to the DNA elements to control transcription initiation. The expression vector used may be one capable of autonomously replicating in the host cell or capable of integrating into the chromosome, originally containing a promoter at a site enabling transcription of the linked gene.

Yeast or fungal expression vectors may comprise an origin of replication, a suitable promoter and enhancer, and also any necessary ribosome binding sites, polyadenylation site, splice donor and acceptor sites, transcriptional termination sequences, and 5=flanking nontranscribed sequences. Several well-characterized yeast expression systems are known in the art and described in, e.g., U.S. Pat. No. 4,446,235, and European Patent Applications 103,409 and 100,561. A large variety of shuttle vectors with yeast promoters are also known to the art. However, any other plasmid or vector may be used as long as they are replicable and viable in the host.

The construction of vectors that may be employed in conjunction with the present invention will be known to those of skill of the art in light of the present disclosure (see, e.g., Sambrook and Russell, *Molecular Biology: A Laboratory Manual*, 2001). The expression cassette of the invention may contain one or a plurality of restriction sites allowing for placement of the polynucleotide encoding an enzyme. The expression cassette may also contain a termination signal operably linked to the polynucleotide as well as regulatory sequences required for proper translation of the polynucleotide. The expression cassette containing the polynucleotide of the invention may be chimeric, meaning that at least one of its components is heterologous with respect to at least one of the other components. Expression of the polynucleotide in the expression cassette may be under the control of a constitutive promoter, inducible promoter, regulated promoter, viral promoter or synthetic promoter.

The expression cassette may include, in the 5'-3' direction of transcription, a transcriptional and translational initiation region, the polynucleotide of the invention and a transcriptional and translational termination region functional in vivo and/or in vitro. The termination region may be native with the transcriptional initiation region, may be native with the polynucleotide, or may be derived from another source. The regulatory sequences may be located upstream (5' non-coding sequences), within (intron), or downstream (3' non-coding sequences) of a coding sequence, and influence the transcription, RNA processing or stability, and/or translation of the associated coding sequence. Regulatory sequences may include, but are not limited to, enhancers, promoters, repressor binding sites, translation leader sequences, introns, and polyadenylation signal sequences. They may include natural and synthetic sequences as well as sequences that may be a combination of synthetic and natural sequences.

The vector used in the present invention may also include appropriate sequences for amplifying expression.

A promoter is a nucleotide sequence that controls the expression of a coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be derived entirely from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. A promoter may also include a minimal promoter plus a regulatory element or elements capable of controlling the expression of a coding sequence or functional RNA. This type of promoter sequence contains of proximal and more distal elements, the latter elements are often referred to as enhancers.

Representative examples of promoters include, but are not limited to, promoters known to control expression of genes in prokaryotic or eukaryotic cells or their viruses. For instance, any promoter capable of expressing in yeast hosts can be used as a promoter in the present invention, for example, the GAL4 promoter may be used. Additional promoters useful for expression in a yeast cell are well described in the art.

Examples thereof include promoters of the genes coding for glycolytic enzymes, such as TDH3, glyceraldehyde-3-phosphate dehydrogenase (GAPDH), a shortened version of GAPDH (GAPFL), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, invertase and glucokinase genes and the like in the glycolytic pathway, heat shock protein promoter, MFa-1 promoter, CUP 1 promoter, MET, the promoter of the TRP1 gene, the AOX (alcohol oxidase) gene promoter, e.g., the AOX1 or AOX2 promoter, the ADC1 gene (coding for the alcohol dehydrogenase I) or ADR2 gene (coding for the alcohol dehydrogenase II), acid phosphatase (PHO5) gene, isocytochrome c gene, a promoter of the yeast mating pheromone genes coding for the a- or α-factor, or the GAL/CYC1 hybrid promoter (intergenic region of the GAL1-GAL10 gene/Cytochrome) gene) (Guarente et al. 1982). Promoters with transcriptional control that can be turned on or off by variation of the growth conditions include, e.g., PHO5, ADR2, and GAL/CYC1 promoters. The PHO5 promoter, for example, can be repressed or derepressed at will, solely by increasing or decreasing the concentration of inorganic phosphate in the medium. Some promoters, such as the ADH1 promoter, allow high-level constitutive expression of the gene of interest.

Any promoter capable of expressing in filamentous fungi may be used. Examples are a promoter induced strongly by starch or cellulose, e.g., a promoter for glucoamylase or α-amylase from the genus *Aspergillus* or cellulase (cellobiohydrase) from the genus *Trichoderma*, a promoter for enzymes in the glycolytic pathway, such as phosphoglycerate kinase (pgk) and glycerylaldehyde 3-phosphate dehydrogenase (gpd), etc.

Particular bacterial promoters include but are not limited to *E. coli* lac or trp, the phage lambda $P_L$, lacI, lacZ, T3, T7, gpt, and lambda $P_R$ promoters.

Two principal methods for the control of expression are known, viz.: induction, which leads to overexpression, and repression, which leads to underexpression. Overexpression can be achieved by insertion of a strong promoter in a position that is operably linked to the target gene, or by insertion of one or more than one extra copy of the selected gene. For example, extra copies of the gene of interest may be positioned on an autonomously replicating plasmid, such as pYES2.0 (Invitrogen Corp., Carlsbad, Calif.), where overexpression is controlled by the GAL4 promoter after addition of galactose to the medium.

Several inducible promoters are known in the art. Many are described in a review by Gatz, *Curr. Op. Biotech.*, 7:168 (1996) (see also Gatz, *Ann. Rev. Plant. Physiol. Plant Mol. Biol.*, 48:89 (1997)). Examples include tetracycline repressor system, Lac repressor system, copper-inducible systems, salicylate-inducible systems (such as the PR1a system), glucocorticoid-inducible (Aoyama T. et al., 1997), alcohol-inducible systems, e.g., AOX promoters, and ecdysome-inducible systems. Also included are the benzene sulphonamide-inducible (U.S. Pat. No. 5,364,780) and alcohol-inducible (WO 97/06269 and WO 97/06268) inducible systems and glutathione S-transferase promoters.

In addition to the use of a particular promoter, other types of elements can influence expression of transgenes. In particular, introns have demonstrated the potential for enhancing transgene expression.

Other elements include those that can be regulated by endogenous or exogenous agents, e.g., by zinc finger proteins, including naturally occurring zinc finger proteins or chimeric zinc finger proteins. See, e.g., U.S. Pat. No. 5,789,538, WO 99/48909; WO 99/45132; WO 98/53060; WO 98/53057; WO 98/53058; WO 00/23464; WO 95/19431; and WO 98/54311.

An enhancer is a DNA sequence that can stimulate promoter activity and may be an innate element of the promoter or a heterologous element inserted to enhance the level or tissue specificity of a particular promoter. An enhancer is capable of operating in both orientations (5' to 3' and 3' to 5' relative to the gene of interest coding sequences), and is capable of functioning even when moved either upstream or downstream from the promoter. Both enhancers and other upstream promoter elements bind sequence-specific DNA-binding proteins that mediate their effects.

Vectors for use in accordance with the present invention may be constructed to include an enhancer element. Constructs of the invention will also include the gene of interest along with a 3' end DNA sequence that acts as a signal to terminate transcription and allow for the polyadenylation of the resultant mRNA.

As the DNA sequence between the transcription initiation site and the start of the coding sequence, i.e., the untranslated leader sequence, can influence gene expression, one may also wish to employ a particular leader sequence. Preferred leader sequences are contemplated to include those that include sequences predicted to direct optimum expression of the attached gene, i.e., to include a preferred consensus leader sequence that may increase or maintain mRNA stability and prevent inappropriate initiation of translation. The choice of such sequences will be known to those of skill in the art in light of the present disclosure.

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait that one can select for by chemical means, i.e., through the use of a selective agent (e.g., an antibiotic, or the like), or whether it is simply a trait that one can identify through observation or testing, i.e., by screening. Of course, many examples of suitable marker genes are known to the art and can be employed in the practice of the invention.

Included within the terms selectable or screenable marker genes are also genes that encode a "secretable marker" whose secretion can be detected as a means of identifying or selecting for transformed cells. Examples include markers that encode a secretable antigen that can be identified by antibody interaction, or even secretable enzymes that can be detected by their catalytic activity. Secretable proteins fall into a number of classes, including small, diffusible proteins detectable, e.g., by ELISA and small active enzymes detectable in extracellular solution.

Screenable markers that may be employed include, but are not limited to, a β-glucuronidase or uidA gene (GUS) that encode an enzyme for which various chromogenic substrates are known; a beta-lactamase gene (Sutcliffe, 1978), which encodes an enzyme for which various chromogenic substrates are known (e.g., PADAC, a chromogenic cephalosporin); a xylE gene (Zukowsky et al., 1983), which encodes a catechol dioxygenase that can convert chromogenic catechols; an alpha-amylase gene (Ikuta et al., 1990); a tyrosinase gene (Katz et al., 1983) that encodes an enzyme capable of oxidizing tyrosine to DOPA and dopaquinone that in turn condenses to form the easily detectable compound melanin; a beta-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995). Selectable nutritional markers may also be used, such as HIS3, URA3, TRP-1, LYS-2 and ADE2.

Any construct encoding a gene product that results in a recombinant cell useful in biocatalysis may be employed. In one embodiment, the construct encodes an enzyme. Sources of genes for enzymes include those from fungal cells belonging to the genera *Aspergillus, Rhizopus, Trichoderma, Neurospora, Mucor, Penicillium*, yeast belonging to the genera *Kluyveromyces, Saccharomyces, Schizosaccharomyces, Trichosporon, Schwanniomyces*, plants, vertebrates and the like. In one embodiment, the construct is on a plasmid suitable for extrachromosomal replication and maintenance. In another embodiment, two constructs are concurrently or sequentially introduced to a cell so as to result in stable integration of the constructs into the genome.

In one embodiment, a spray-dried preparation of *Pichia* suitable for biocatalysis is provided. In another embodiment, a spray-dried preparation of *Saccharomyces* suitable for biocatalysis is provided. Nevertheless, as yeast have cell walls, it is envisioned that spray-dried preparations of yeast other than *Pichia* or *Saccharomyces* may be employed for biocatalysis. In one embodiment, the yeast comprises at least one recombinant enzyme. For example, the recombinant enzyme may be a heterologous enzyme. In one embodiment, the yeast does not express a recombinant enzyme, e.g., wild-type (or otherwise nonrecombinant) yeast such as *Saccharomyces* may be employed for biocatalysis.

In one embodiment, a spray-dried preparation of prokaryotic cells such as *E. coli* for biocatalysis is provided. For example, a recombinant *E. coli* strain comprises at least one recombinant enzyme. In one embodiment, the *E. coli* strain is transformed with a prokaryotic vector derived from pET32.

To prepare recombinant strains of microbes, the microbial genome is augmented or a portion of the genome is replaced with an expression cassette. For biocatalysis, the expression cassette comprises a promoter operably linked to an open reading frame for at least one enzyme that mediates the biocatalysis. For example, the expression cassette may encode a heterologous enzyme. In one embodiment, the microbial genome is transformed with at least two expression cassettes, e.g., one expression cassette encodes one heterologous enzyme and another encodes a different heterologous enzyme. The expression cassettes may be introduced on the same or separate plasmids or the same or different vectors for stable integrative transformation.

Recombinant or native (nonrecombinant) microbes expressing one or more enzymes that mediate a particular enzymatic reaction are expanded to provide a microbial cell suspension. In one embodiment, the suspension may be separated into a liquid fraction and a solid fraction which contains the cells, e.g., by centrifugation or use of a membrane, prior to spray drying. The microbial cell suspension is spray-dried under conditions effective to yield a spray-dried microbial cell preparation suitable for biocatalysis. In one embodiment, the spray drying includes heating an amount of the cell suspension flowing through an aperature. The conditions described in the examples below were set based on small-scale instrument capacity, e.g., low evaporation capacity (e.g., 1.5 Kg water/hour). Thus, the ranges below are exemplary only and may be different at a manufacturing scale where evaporation capacity may reach over 1000 Kg water/hour. For example, for a small scale instrument, the feed (flow) rate may be about 1 mL/minute to about 30 mL/minute, e.g., about 2 mL/minute up to about 20 mL/minute. Flow rates for large scale processes may be up to or greater than 1 L/minute. In one embodiment, the suspension is dried at about 50° C. up to about 225° C., e.g., about 100° C. up to about 200° C. The cell suspension prior to spray drying may be at about 5 mg/L up to about 800 mg/L, for instance, about 20 mg/L up to about 700 mg/L, or up to or greater than 2000 mg/L. The upper limit of the concentration of cells employed is determined by the viscosity of the cells and the instrument. The microbial cell suspension may be an *E. coli* cell suspension, a *Pseudomonas* cell suspension, a *Pichia* cell suspension or a *Saccharomyces* cell suspension. In one embodiment, air flow is about 500 L/hr to about 800 L/hr, e.g., about 700 L/hr. The process to prepare a spray-dried microbial cell preparation may include any flow rate, any temperature and any cell concentration described herein, as well as other flow rates, temperatures and cell concentrations.

Once desirable native or recombinant microbial cells are spray-dried, they may be stored for any period of time under conditions that do not substantially impact the activity or cellular location of enzymes to be employed in biocatalysis. Storage periods include hours, days, weeks, and up to at least 2 months.

The invention will be further described by the following non-limiting examples.

EXAMPLE 1

Decaffeination of Coffee and Black Tea Extracts by *Pseudomonas putida* CBB5

In a study to demonstrate the utility of *Pseudomonas putida* CBB5 and *Pseudomonas* sp CBB1 in caffeine remediation process, the effect of caffeine-grown cells on coffee and black tea extract was examined. *Pseudomonas putida* CBB5 was grown in M9 mineral salts medium containing 2.5 g·l−1 caffeine and 4 g·l−1 soytone, at 30° C. with shaking at 200 rpm. Cell density was monitored by measuring the optical density at 600 nm ($OD_{600}$). Upon reaching an $OD_{600}$ of 2.0 to 2.5, cells were harvested by centrifugation (10,000×g for 10 minutes at 4° C.) and washed twice in 50 mM potassium phosphate (KPi) buffer (pH 7.5). The cells were then suspended in 5 ml of KPi buffer at a final $OD_{600}$ of 4, 20 and 40. Coffee extract was made by boiling 100 g of commercially available coffee powder in water at 100° C. for 15 minutes. The extract was then filtered and amount of caffeine concentration was analyzed as described in Yu et al. (2009). About 18 mM of caffeine was present in the extract. The resting cell experiments were carried out with both coffee extract and standard caffeine in buffer at three different concentrations 1 mM, 9 mM and 18 mM. Samples were taken at 30 minute intervals and analyzed by HPLC for caffeine disappearance, as published in Yu et al. (2009). *Pseudomonas putida* CBB5 efficiently degraded 18 mM caffeine in the extract in 6 hours. At every concentration, not surprisingly, caffeine degradation in buffer was faster than in the extract. At the highest concentration, caffeine degradation in the extract took 6 hours vs. 2 hours in buffer solution. The slower rate in the coffee extract may be due to the presence of inhibitors such as polyols, tannins and other uncharacterized components.

Similarly resting cell experiments were carried out on the black tea extract using *Pseudomonas putida* CBB5. The cells were suspended in 5 ml of KPi buffer to a final $OD_{600}$ of 4 and 20. Black tea extract was prepared by boiling 100 g of tea powder in water over 100° C. for 15 minutes and the extract was filtered. Caffeine concentration was analyzed as described in Yu et al. (2009) and found to contain 8.3 mM. Caffeine degradation with resting cell experiments were carried out with tea extract two different concentrations of caffeine, 1 mM and 8 mM. Samples were taken at 30 minute intervals and analyzed by HPLC as published in Yu et al. (2009). In the diluted tea extract, caffeine was degraded by CBB5 cells within 40 minutes with accumulation of xanthine which was later substantially degraded in 120 minutes.

In contrast, caffeine in undiluted tea extract disappeared in 40 minutes, but several downstream metabolites were detected initially. Subsequently in 120 minutes most of the methylxanthines were also degraded. This preliminary experiment clearly demonstrates that caffeine in coffee and tea extracts can be removed completely by CBB5. Other components in the tea extracts including phenols and tannins did not inhibit caffeine degradation by CBB5. Thus, environmental caffeine decontamination applications, e.g., in treatment of caffeine contaminated waters as well as agro-industrial waste from coffee industry, may be feasible.

Degradation of Black Tea Extracts by *Pseudomonas* CBB1

*Pseudomonas* sp. CBB1 was grown in M9 mineral salts medium containing 2.5 g·l-1 caffeine and 4 g·l-1 yeast nitrogen base, at 30° C. with shaking at 200 rpm. Cell density was monitored by measuring the optical density at 600 nm ($OD_{600}$). Upon reaching log phase cells were harvested by centrifugation (13,800×g for 10 minutes at 4° C.) and washed twice in 50 mM potassium phosphate (KPi) buffer (pH 7.5). The cells are suspended in 5 ml of KPi buffer at a final $OD_{600}$ of 20. Black tea extract was prepared by boiling tea powder as described above and analyzed for caffeine content as described by Yu et al. (2008). The degradation experiment was carried out using resting cells in tea extract which contained 8.3 mM of caffeine. Caffeine at the same concentration in KPi buffer was used as control. Samples were removed at 30 minute intervals and analyzed by HPLC as described by Yu et al. (2008). *Pseudomonas* sp. CBB1 degraded caffeine in tea extract rather slowly, over a period of 250 minutes.

In contrast, caffeine was completely degraded in control solution in less than 100 minutes. TMU was detected in the controls, which eventually disappeared in 250 minutes. About 40% of caffeine degradation occurred in black tea extract, but TMU was not detected. The presence of various inhibitory compounds in the tea extract is likely the reason for very slow degradation of caffeine by CBB1.

Preliminary experiments indicate that CBB5 may be more efficient in decontaminating caffeine in both coffee and tea extracts. CBB1 was not tested with coffee extracts due to its poor performance with tea extracts. CBB5 and CBB1 use different enzymes to initiate caffeine degradation, i.e., N-demethylase vs. Cdh. Thus the nature and concentration of inhibitors in coffee and tea extracts could impact differently in terms of caffeine decontamination.

Development of Diagnostic Test for Caffeine

There is increasing health concern due to excessive caffeine consumption from coffee, tea or caffeine containing beverages, especially on breast-feeding mothers. The effect of caffeine via breast milk can have more pronounced effects on children. Hence, it would be desirable to have a rapid test to determine caffeine content in breast milk before feeding. Likewise, during field trips, a device for rapid measurement of caffeine in environmental samples is desirable. In both academic and industrial laboratories caffeine is routinely measured by GC, HPLC and these methods are not appropriate for domestic use and in field study to collect real-time data. There is only one rapid 'dip-test' available for measuring caffeine levels, which is the test strip, D+Caf™. This strip is based on lateral flow immunoassay (Landenson et al., 2006). It is a qualitative test for the presence or absence of caffeine. Also, this commercially available test strip does not have the desired sensitivity. Another limitation of this test strip is its inability to test caffeine in the presence of other components. For example, milk or coffee creamer in coffee interfere with this test (Landenson et al., 2006). There is also a need for detection of caffeine in formulations such as drugs, pharmaceutical products, and nutraceuticals, many of which contain caffeine.

Caffeine dehydrogenase (Cdh) from CBB1, which catalyzes the conversion of caffeine to TMU, is a suitable enzyme to develop a semi-quantitative 'dip-stick' test. There are several attributes to a Cdh-based diagnostic test. The enzyme is specific for caffeine with a $K_m$ of 3.7±0.9 µM (Yu et al., 2008) with no activity towards structurally related xanthine or theophylline. Preference for theobromine as a substrate is 50 times less than caffeine. Presence of oxygen in solution does not interfere with the detection of caffeine and the enzyme does not require any cofactors. A preliminary study was carried out in a 96-well format, to develop a Cdh-based caffeine diagnostic kit. Purified as enzyme, as described by Yu et al. (2008) was used for this purpose. Several tetraaolium dyes were tested as electron acceptors as well as for background reduction without the enzyme. The dyes used include Iodonitrotetrazolium Chloride (INT), Tetrazolium Blue Chloride (TB), Thiazolyl Blue Tetrazolium Bromide (MTT), Tetrazolium Violet (TV), Nitro Blue Tetrazolium (NBT) and Tetra nitro blue Tetrazolium (TNBT). The assay was carried out at various concentrations of caffeine ranging from 0-12 mg/L in buffer and whole milk. The color changes with various electron acceptors were distinct over different concentration of caffeine. Among the different electron acceptors studied the color change with Iodonitrotetrazolium Chloride (INT) was very sensitive, even at concentrations as low as 0.7 mg/L caffeine in milk. NBT was also quite sensitive in detecting caffeine at 3 mg/L and is readily available unlike other dyes. Caffeine dehydrogenase has several advantages over D+Caf™ like (i) high specificity for caffeine, (ii) the color formation will not be affected in presence of milk or creamer, (iii) high sensitivity, and (iv) speed of detection, etc. Further work is in progress to determine several parameters like the most suitable dye, stability and shelf life of the enzyme, activity at room temperature vs. higher temperature, in order to assess the development of Cdh-based dip-stick test.

*Pseudomonas putida* CBB5 for Preparation of Alkyl Xanthines

A variety of xanthines have been developed as potent and/or selective antagonists for adenosine receptors (Burns et al., 1980). Several xanthine derivatives are more potent and more selective inhibitors of cyclic nucleotide phosphodiesterase than caffeine or theophylline (Daly, 2000). Several alkylxanthines are also well known for their pharmacological roles such as antiasthmatic, analgetics, adjuvants, antitussives, and treatment of Parkinson's disease. Alkyxanthines have the potential to be effective therapeutic agents for conditions such as inflammatory cytokines and phagocytic damage, including the sepsis syndrome, ARDS, AIDS, and arthritis (Mandell, 1995).

Chemical synthesis of alkylxanthines from xanthine involves multi steps and is difficult to perform (Shamim et al., 1989). Each nitrogen atom on xanthine is chemically different; hence selective alkylation is not readily attained. In contrast, *Pseudomonas putida* CBB5 catalyzes selective and specific N-demethylation of several alkylated xanthines such as caffeine, theobromine, theophylline and paraxanthine. The full range of alkylated xanthines N-demethylated by CBB5 has not been explored. Nevertheless, CBB5 whole cells can be used to produce high value dimethyxanthines and mono methylxanthines from readily available starting material, caffeine. For example, this bacterium can be used for a novel approach to produce 1,7-dimethyl xanthine (paraxanthine), 1-methyl xanthine and 3-methyl xanthine from caffeine. Alternately, various N-demethylases in CBB5 can be cloned in an organism such as *E. Coli* and specific dimethyl- and monomethylxanthines can be produced using glucose as energy source.

EXAMPLE 2

Caffeine (1,3,7-trimethylxanthine), theophylline (1,3-dimethylxanthine), and related methylxanthines are naturally occurring purine alkaloids that are present in many plant species. As a major human dietary component, caffeine can be found in common food and beverage products such as coffee, tea, colas, and chocolates. Caffeine has been used in pharmaceutical preparations as a neurological, cardiac, and respiratory stimulant. It is also used as an analgesic enhancer in cold, cough, and headache medicines (Daly, 2007). Other pharmaceutical applications of methylxanthines include use as a diuretic, bronchodilator, relief of bronchial spasms, and control of asthma (Daly, 2007). 1-Methylxanthine, 1-methyluric acid, and uric acid have also been studied for their antioxidant properties (Lee, 2000). Because of their wide use in food and pharmaceutical industries, caffeine and related methylxanthines enter the environment via liquid effluents, solid wastes from processing facilities, decomposition of plant matter in coffee and tea fields, and domestic wastes. This can have adverse environmental effects, as methylxanthines serve as a soil sterilant by inhibiting seed germination (Smyth, 1992). Caffeine has been suggested as an anthropogenic marker for wastewater pollution of drinking water (Buerge et al., 2003; Ogunseitan, 1996; Seiler et al., 1999).

Some bacteria utilize caffeine as sole growth substrate and metabolize it via oxidation at the C-8 position to form 1,3,7-trimethyluric acid (Madyastha & Sridhar, 1998; Mohapatra et al., 2006; Yu et al., 2008). This reaction is catalyzed by a number of different enzymes in several bacteria. An 85-kDa, flavin-containing caffeine oxidase was purified from a mixed culture of *Rhodococcus* sp. and *Klebsiella* sp. (Madyastha et al., 1999). A 65-kDa caffeine oxidase was also purified from *Alcaligenes* sp. strain CF8 (Mohapatra et al., 2006). A heterotrimeric, non-NAD(P)$^+$-dependent caffeine dehydrogenase from *Pseudomonas* sp. strain CBB1 was recently purified. This enzyme stoichiometrically and hydrolytically oxidized caffeine to trimethyluric acid (Yu et al., 2008).

Several bacterial strains capable of utilizing caffeine as sole growth substrate metabolize caffeine via N-demethylation. The majority of these belong to the genera *Pseudomonas* (Asano et al., 1993; Blecher & Lingens, 1977; Dash & Gummadi, 2008; Sideso et al., 2001; Woolfolk, 1975; Yu et al., 2009), however a strain of *Serratia marcescens* was also found to N-demethylate caffeine (Mazzafera et al., 1996). N-Demethylation of caffeine in bacteria results in production of either theobromine (3,7-dimethylxanthine) or paraxanthine (1,7-dimethylxanthine). Paraxanthine and theobromine are further N-demethylated to 7-methylxanthine and xanthine. Xanthine is subsequently oxidized to uric acid by either xanthine oxidase/dehydrogenase, and the uric acid enters the normal purine catabolic pathway to form $CO_2$ and $NH_4^+$ (Dash & Gummadi, 2006). Theophylline, the major caffeine metabolite in filamentous fungi (Hakil et al., 1998), has not been reported as a bacterial metabolite of caffeine.

*Pseudomonas putida* CBB5 is capable of utilizing a number of natural purine alkaloids as sole source of carbon and nitrogen (Yu et al., 2009). This organism metabolizes caffeine via sequential N-demethylation to paraxanthine and theobromine, 7-methylxanthine, and xanthine. A previously unknown pathway for N-demethylation of theophylline to 1- and 3-methylxanthines, which were further N-demethylated to xanthine, was also discovered in CBB5. While caffeine and theophylline degradation pathways were co-expressed in the presence of caffeine, theophylline, and related methylxanthines, the intermediate metabolites of the two pathways do not overlap until xanthine (Yu et al., 2009). In spite of several N-demethylation reports on metabolism of purine alkaloids by bacteria, there is no report of a well characterized enzyme that enables the utilization of these substrates for growth. As described below, a soluble, broad specificity methylxanthine N-demethylase was purified from CBB5 and characterized. This enzyme is composed of a reductase component (Ccr) and a two-subunit N-demethylase component (Ndm).

Ndm activity is dependent on NAD(P)H oxidation, catalyzed by Ccr. Furthermore, Ndm is predicted to be a Rieske [2Fe-2S] domain-containing, non-heme iron oxygenase based on analysis of the N-terminal protein sequences of its subunits as well as distinct UV/visible absorption spectrum. When coupled with Ccr, Ndm exhibited broad-based activity towards caffeine, paraxanthine, theobromine, theophylline, 7-methylxanthine, and 3-methylxanthine, converting all of these to xanthine.

Methods

Chemicals. Caffeine, theophylline, theobromine, paraxanthine, 7-methylxanthine, 3-methylxanthine, xanthine, ammonium acetate, acetic acid, 2,4-pentanedione, spinach ferredoxin reductase, and spinach ferredoxin were purchased from Sigma-Aldrich. Reductase and ferredoxin of *Pseudomonas* sp. 9816 naphthalene dioxygenase were kindly provided by Dr. David T. Gibson. Soytone was obtained from Becton, Dickinson and Company. High-pressure liquid chromatography (HPLC)-grade methanol (J. T. Baker) was used in chromatographic studies.

Culture conditions. CBB5 was grown in M9 mineral salts medium (Sambrook et al., 1989) containing 2.5 g caffeine $L^{-1}$ and 4 g soytone $L^{-1}$, at 30° C. with shaking at 200 rpm. Cell density was monitored by measuring the optical density at 600 nm ($OD_{600}$). Upon reaching an $OD_{600}$ of 2.1, cells were harvested by centrifugation (10,000×g for 10 minutes at 4° C.) and washed twice in 50 mM potassium phosphate (KPi) buffer (pH 7.5). Pelleted cells were suspended in 50 mM KPi buffer with 5% (v/v) glycerol and 1 mM DTT (KPGD buffer) to a final volume of 2 ml for every 1 g cells (wet weight) and stored 120 at −80° C.

Cell Extract Preparation. About 16.6 g frozen cells suspended in 35 mL KPGD buffer were thawed and DNase I was added to a final concentration of 10 μg $ml^{-1}$. The cells were broken by passing through a chilled French press cell twice at 138 MPa. Unbroken cells and debris were removed from the lysate by centrifugation (16,000×g for 20 minutes at 4° C.), and the supernatant was designated as the cell extract.

Enzyme Purification. All purification procedures were performed at 4° C. using an automated fast protein liquid chromatography system (AKTA FPLC, Amersham Pharmacia Biotech). After each chromatographic step, eluant fractions were assayed for N-demethylase (Ndm) and cytochrome c reductase (Ccr) activities as described below. Fractions with activities were concentrated using Amicon ultrafiltration units with MWCO 10,000 (Millipore). Purity of the enzyme was determined under native and denaturing conditions with PAGE on 4-15% Tris-HCl gels (Bio-Rad) and 10% Bis-Tris gels with MOPS running buffer containing SDS (Invitrogen), respectively.

Cell extract was loaded onto a 160-mL (bed volume) DEAE Sepharose column (GE Healthcare) pre-equilibrated in KPGD buffer. After washing unbound proteins from the column with 160 ml KPGD buffer, the bound proteins were eluted from the column with a 540-mL linear gradient of KCl (0 to 0.4 M) in KPGD buffer. Fractions with Ndm activity were pooled and concentrated.

A 4.0 M ammonium sulfate solution was added to the Ndm activity-containing fractions from DEAE Sepharose to a final concentration of 0.25 M with constant stirring. After 20 minutes, the mixture was centrifuged (16,000×g for 20 minutes), and the supernatant was loaded onto a 30-mL (bed volume) Phenyl Sepharose High Performance column (Amersham) pre-equilibrated in KPGD buffer containing 0.25 M ammonium sulfate. Unbound proteins were eluted from the column with 60 mL KPGD buffer containing 0.25 M ammonium sulfate. Bound proteins were eluted with a 30-ml reverse linear gradient of ammonium sulfate (0.25 to 0 M in KPGD buffer) at a flow rate of 1 mL min$^{-1}$. The column was then washed with 45 mL KPGD buffer, followed by 60 mL deionized water containing 1 mM DTT and 5% (v/v) glycerol.

Phenyl Sepharose eluants with N-demethylase activity were pooled, concentrated to 2 mL, and loaded onto a 5-mL (bed volume) Q Sepharose column (GE Healthcare) pre-equilibrated in KPGD buffer containing 0.2 M KCl. After washing unbound proteins from the column with 10 mL equilibration buffer, bound proteins were eluted from the column using a 120-mL linear gradient of KCl (0.2 to 0.4 M) in KPGD buffer. Ndm was eluted from the Q Sepharose column as a single peak around 0.29 M KCl.

Enzyme Activity Assays. NADH:cytochrome c oxidoreductase (cytochrome c reductase, Ccr) activity was determined as described by Ueda et al. (1972). A typical 1-mL reaction contained 300 μM NADH, 87 μM bovine cytochrome c (type III; Sigma), and 1-20 μg CBB5 protein (depending on purity) in 50 mM KPi buffer. The activity was determined by monitoring the increase in absorbance at 550 nm due to reduction of 160 cytochrome c at 30° C. An extinction coefficient of 21,000 M$^{-1}$ cm$^{-1}$ for reduced minus oxidized cytochrome c was used for quantitating the activity. One unit of activity was defined as one μmol of cytochrome c reduced per minute.

Methylxanthine N-demethylase activity assay contained, in 1-mL total volume, 0.5 mM methylxanthine, 1 mM NADH, 50 μM Fe(NH$_4$)$_2$(SO$_4$)$_2$, and an appropriate amount of Ndm (0.08-7.5 mg protein, depending on purity of the protein) in 50 mM KPi buffer. Approximately 4 U of partially purified Ccr was added to reaction mixture when assaying Ndm in Phenyl Sepharose and Q Sepharose eluant-fractions (Ccr was not added to the enzyme reaction mixture when assaying Ndm activity in DEAE Sepharose eluant-fractions because Ccr co-eluted with Ndm). The reaction mixture was incubated at 30° C. with 300 rpm shaking on an incubating microplate shaker (VWR). Periodically, a small aliquot was sampled from the reaction mixture and mixed with equal volume of acetonitrile for quantifying concentrations of methylxanthines and N-demethylated products by HPLC. One unit of N-demethylase activity was defined as the consumption of one μmole methylxanthine per minute. When Ndm was coupled with the reductase and ferredoxin components of naphthalene dioxygenase of *Pseudomonas* sp. strain 9816 (Haigler & Gibson, 1990a; Haigler & Gibson, 1990b), 30 and 100 μg of the respective proteins were used. Spinach ferredoxin reductase and ferredoxin were also substituted for Ccr as described by Subramanian et al. (1979).

Molecular mass estimation. The molecular mass of the Ndm subunits were estimated under denaturing conditions by PAGE on 10% Bis-Tris gels with MOPS running buffer containing SDS (Invitrogen). Native molecular mass of Ndm was determined by gel filtration chromatography using an 80-mL ($V_c$, geometrical volume) Sephacryl S-300 HR column (Amersham) equilibrated with 0.1 M KCl in 50 mM Kpi buffer at 1 mL min$^{-1}$. Void volume ($V_o$) of the column was determined by measuring the elution volume ($V_e$) of a 1 mg mL$^{-1}$ solution of blue dextran 2000 (GE Healthcare). The column was calibrated with ferritin (440 kDa), catalase (232 kDa), adolase (158 kDa), and conalbumin (75 kDa). The $V_e$ of each standard protein was measured, from which the respective $K_{av}$ value was calculated according to the equation $$K_{av} = \frac{V_e - V_o}{V_c - V_o}.$$

A standard curve of $K_{av}$ values against the logarithmic molecular masses of the standard proteins was then used to determine the native molecular mass of Ndm.

Determination of pH Optimum. To determine pH optimum, Ndm activity was measured as described above at various pH values within the range of 6.0 to 8.0 by using 50 mM KPi buffer.

Determination of Kinetic Parameters. Apparent kinetic parameters of Ndm were determined by measuring the initial rate of disappearance ($v_o$) of paraxanthine or 7-methylxanthine in 50 mM KPi buffer (pH 7.5) at 30° C. The paraxanthine and 7-methylxanthine concentrations ([S]) used in these experiments were from 20 to 500 μM. Substrates were incubated with Ndm and Ccr under standard conditions for 15 minutes. At 1, 5, 10, and 15 minutes, samples were removed from the reaction mixtures to quantitate substrate concentrations by HPLC. Plots of substrate concentrations against time were used to determine the initial rates of disappearance of substrates which were linear over 15 minutes. The apparent kinetic parameters were determined from Michaelis-Menten plots of $V_o$ against [S] fitted with the equation $$v_o = \frac{k_{cat}[E_T][S]}{K_M + [S]},$$

where [$E_T$] is the concentration of enzyme in the reaction. All of the experiments were performed in triplicate and the data were analyzed by using GraFit 5.0 software (Erithacus Software Limited).

Determination of Oxygen Requirement. Oxygen consumption by Ndm during N-demethylation of paraxanthine was determined in a closed reaction vessel equipped with a Clarke-type oxygen electrode (Digitial Modell 0, Rank Brothers Ltd., Cambridge, England). The electrode was calibrated by using glucose oxidase (Sigma) and glucose for consumption of oxygen. Ndm activity assay was performed at 30° C. in a total volume of 1 ml of air-saturated 50 mM KPi buffer (pH 7.5) with 100 μM paraxanthine, 200 μM NADH, 50 μM Fe(NH$_4$)$_2$(SO$_4$)$_2$, 0.2 mg purified Ndm, and 4 U partially purified Ccr. The reaction was initiated by adding Ndm and partially purified Ccr after equilibration of all other reaction components for 3.3 minutes. After 13 minutes, a 100-μL aliquot was withdrawn from the reaction, immediately mixed with equal volume of acetonitrile to stop the enzyme reaction, and analyzed for N-demethylation product by HPLC. Background oxygen consumption, possibly due to NADH oxidase enzyme activity in the partially purified Ccr, was quantitated in control reactions containing all reaction components except paraxanthine.

Formaldehyde Determination. Production of formaldehyde during N-demethylation of paraxanthine was determined by derivatizing formaldehyde with Nash reagent prepared by the method of Jones et al. (1999). Twenty μL Nash reagent was added to 50 μl Ndm reaction sample plus 50 μl acetonitrile. This mixture was incubated at 51° C. for 12 minutes. After cooling to room temperature, 3,5-diacetyl-1,4-dihydrolutidine formed from formaldehyde and Nash reagent was analyzed at 412 nm by a HPLC equipped with a photodiode array detector. Standards were prepared with known concentrations of formaldehyde added to control Ndm enzyme reaction mixtures without paraxanthine.

Analytical Procedures. Identification and quantification of methylxanthines and their metabolites were conducted with a Shimadzu LC-20AT HPLC system equipped with a SPD-M20A photo diode array detector and a Hypersil BDS C 18 column (4.6 by 125 mm) as described previously (Yu et al., 2009). For analysis of 3,5-diacetyl-1,4-dihydrolutidine, methanol-water-acetic acid (30:20:0.5, v/v/v) was used as an isocratic mobile phase at a flow rate of 0.5 mL min$^{-1}$. Protein concentration was determined by the Bradford method (Bradford, 1976) using bovine serum albumin as the standard with a dye reagent purchased from Bio-Rad. The N-terminal amino acid sequences of both Ndm subunits were determined at the Protein Facility, Iowa State University, Ames, Iowa. Iron content in Ndm was determined by ICP-MS. An aliquot of purified Ndm was mixed with equal volume of trace metal-free, ultrapure concentrated nitric acid. The mixture was heated at 160° C. for 1 hour to breakdown all organic materials. The acid digest was then diluted appropriately with ultrapure water for quantification of iron by a Thermo X-series II ICP-MS system at the Department of Geosciences, University of Iowa. The ICP-MS system was calibrated with high purity iron standard solution. Bovine cytochrome c was used as positive control.

Results

N-Demethylase Activity of CBB5 Cell Extracts. NADH-dependent N-demethylase (Ndm) activity in cell extracts prepared from CBB5 grown on caffeine plus soytone was tested on caffeine, theophylline, paraxanthine, and theobromine in order to determine which substrate was utilized most rapidly. A 0.5 mM paraxanthine solution was completely utilized by 7.2 mg mL$^{-1}$ protein in about 20 minutes (FIG. 1). Degradation of theobromine, caffeine, and theophylline were significantly slower. Hence, paraxanthine was chosen as the substrate to monitor the purification of the enzyme, and in subsequent enzyme activity assays.

Purification of Ndm. Ndm was purified from CBB5 cell extracts (Table 3).

TABLE 3

Purification of methylxanthine N-demethylase from *Pseudomonas putida* CBB5.

| Purification Step | Total Protein (mg) | Total Activity (mU)* | Sp Act (mU/mg) | Purification (fold) | Yield (%) |
|---|---|---|---|---|---|
| Cell extract | 2361 | 5053 | 2.1 | 1 | 100 |
| DEAE Sepharose | 480.2 | 1767 | 3.7 | 1.7 | 35 |
| Phenyl Sepharose HP | 37.5 | 962 | 25.6 | 12 | 19 |
| Q Sepharose | 7.0 | 388 | 55.4 | 26 | 7.7 |

*One unit activity = 1 μmole paraxanthine consumed min$^{-1}$, in the presence of saturating amounts of Ccr and 50 μM Fe$^{2+}$, as described in the Materials and Methods.

The 3-step procedure resulted in a 26-fold purification of Ndm, relative to the activity in cell extract. A NAD(P)H: cytochrome c oxidoreductase (Ccr) activity co-eluted with Ndm from the DEAE Sepharose column at 0.23 M KCl in KPGD. NADH is the preferred substrate of Ccr; activity with NADPH was only 22% of that with NADH. When this DEAE Sepharose eluant was loaded onto the Phenyl Sepharose column, Ccr eluted from the column at 0.05 M $(NH_4)_2SO_4$ and was gold in color. Meanwhile, Ndm was dark red in color and eluted from the column with water, indicating that this component is more hydrophobic. Ndm eluted from Phenyl Sepharose did not contain any Ccr activity. Neither Ccr, Ndm, nor any other Phenyl Sepharose eluant had paraxanthine N-demethylase activity when assayed singly in the presence of NADH. When Ccr and Ndm fractions were combined in the presence of NADH, N-demethylation activity was negligible. However, exogenous addition of 50 μM Fe$^{2+}$ to this reaction mixture resulted in N-demethylation activity of 25.6 mU mg$^{-1}$. This partially purified Ccr fraction was used for assay in the presence of Fe$^{2+}$ during further purification of Ndm in a Q Sepharose column. The dark red color was retained throughout purification. Specific activity of this purified Ndm, in the presence of saturating amount of Ccr, was 55.4 mU 272 mg$^{-1}$. 7-Methylxanthine and xanthine were detected as products.

Biochemical Characterization of Ndm. Analysis of Ndm fraction from Q Sepharose in PAGE gel under denaturing conditions revealed two bands (FIG. 2), with apparent molecular masses of 40 kDa (NdmA) and 35 kDa (NdmB). When this solution was loaded onto a gel filtration chromatography column, the protein eluted as a single, symmetric peak, and the native molecular mass was estimated to be about 240 kDa. Both 40 kDa- and 35 kDa-proteins co-eluted from the gel filtration column, as determined by SDS-PAGE (data not shown). Other chromatographic methods could not further resolve these two proteins. These results suggest that the native Ndm enzyme is likely composed of the two subunits in a hexameric configuration. Ndm stored in KPGD buffer was stable for at least five days at 4° C. and over one month at −80° C. without significant loss of activity (data not shown).

The N-terminal sequence, determined by Edman degradation, of NdmA was MEQAIINDEREYLRHFWHPVCTVTE (SEQ ID NO:3), while that of NdmB was MKEQLKPLLED-KTYLRHFWHPVCTL (SEQ ID NO:4). A BlastP (Altschul et al., 1997) search of the GenBank database, using NdmA and NdmB N-terminal protein sequences as queries, showed that both subunits were most similar to the gene product of *P. putida* strain IF-3 caffeine demethylase gene (accession no. AAB15321) in U.S. Pat. No. 5,550,041 (Koide et al., 1996), and a hypothetical protein in *Janthinobacterium* sp. Marseille (mma_0224, accession no. YP_001351914). NdmA and NdmB N-terminal sequences were 84 and 48%, respectively, identical to the first 25 residues of caffeine demethylase, and 52 and 64%, respectively, identical to the first 25 residues of mma_0224 (FIG. 3A).

Sequence analyses of the caffeine demethylase gene product and mma_0224 predicted both proteins to be Rieske [2Fe-2S] domain-containing, non-heme iron oxygenases (FIG. 3B). UV/visible absorption spectmm of oxidized Ndm had maxima at 318, 440, and 538 nm (FIG. 2B), characteristic of proteins with Rieske-type [2Fe-2S] clusters (Capyk et al., 2009; Fee et al., 1984; Subramanian et al., 1979; Yu et al., 2007). Purified Ndm preparation had an R-value ($A_{280}/A_{440}$) of 11.1 and contained 8.5±0.1 mole of iron per mole of hexameric Ndm, with specific activity of 55 mU mg$^{-1}$ when the enzyme reaction mixture had 50 µM $Fe^{2+}$. Specific activity decreased to 10 mU mg$^{-1}$ if 50 µM $Fe^{2+}$ was not included in the enzyme reaction mixture. Pre-incubation of Ndm for 15 minutes with 1 mM $Fe^{2+}$, followed by desalting, increased the iron content to 20.1±0.3 mole/mole hexameric Ndm. In addition, Ndm specific activities increased to 161 mU mg$^{-1}$ and 127 mU mg when 50 µM $Fe^{2+}$ was present or absent, respectively, in the enzyme reaction mixtures.

Stoichiometric Analysis of Ndm Reaction. Under anaerobic conditions, Ndm had no N-demethylation activity on paraxanthine. Exposure of the anaerobic enzyme reaction mixture to air immediately resumed Ndm activity (data not shown), indicating N-demethylation by Ndm could be oxygen dependent. Stoichiometric consumption of oxygen during N-demethylation of paraxanthine by Ndm was demonstrated by monitoring the reaction with a Clark-type oxygen electrode. After 13 minutes of reaction, 79.5 µM of oxygen was consumed (FIG. 4) while 60.2 µM of paraxanthine was N-demethylated. Approximately 39.9 µM of 7-methylxanthine and 20.3 µM of xanthine were present. These results indicate approximately 1 molecule of $O_2$ was consumed per methyl group removed from paraxanthine. These results also indicate Ndm could remove both methyl groups at the N-I and N-7 positions from paraxanthine.

N-Demethylation of paraxanthine by Ndm also resulted in production of formaldehyde. After 90 minutes of incubation, 338.5±7.7 µM of paraxanthine was N-demethylated by 7.4 units of Ndm and approximately 540.6±20.9 µM of formaldehyde was produced (FIG. 5). 7-Methylxanthine (126.9±6.40 µM) and xanthine (193.7±4.0 µM) were the N-demethylated products. Tallying up all the products formed from paraxanthine, it was determined that approximately one molecule of formaldehyde was produced per methyl group removed.

Substrate Preference of Ndm.

Maximal Ndm activity was observed at pH 7.5 in 50 mM KPi buffer but Ndm was active in the pH range of 6-8. The optimal temperature for Ndm activity was determined to be 30° C. (data not shown). Therefore, kinetic parameters for Ndm, in the presence of saturating amounts of Ccr and 50 µM $Fe^{2+}$, were determined at 30° C. in 50 mM KPi (pH 7.5) buffer. Apparent $K_M$ and $k_{cat}$ values for paraxanthine and 7-methylxanthine were 50.4±6.8 µM and 16.2±0.6 min$^{-1}$ and 63.8±7.5 µM and 94.8±3.0 min$^{-1}$, respectively. Ndm exhibited broad-based activity towards caffeine, theophylline, theobromine, 7-methylxanthine, and 3-methylxanthine, all of which are growth substrates for CBB5. The relative activities in reference to paraxanthine are reported in Table 4. Production of xanthine from all of these methylxanthines was confirmed. Ndm was most active on 7-ethylxanthine, followed by paraxanthine, theobromine, 3-methylxanthine, caffeine, and theophylline. Ndm did not catalyze O-demethylation of vanillate or vanillin even after prolonged incubation.

TABLE 4

Substrate preference of Ndm towards methylxanthines, relative to paraxanthine.

| Substrate | Relative N-demethylase activity at Various substrate conc. (µM) | | Products identified* |
|---|---|---|---|
| | 500 | 200 | |
| Paraxanthine | 100.0 + 3.1 | 100.0 + 3.7 | 7-methylxanthine, xanthine |
| 7-Methylxanthine | 455.7 + 17.6 | 664.2 + 61.1 | xanthine |
| Theobromine | 59.8 + 1.9 | 80.2 + 7.8 | 3- & 7-methylxanthine, xanthine |
| 3-Methylxanthine | 55.2 + 6.0 | 68.9 + 2.6 | xanthine |
| Caffeine | 30.8 + 1.7 | 48.2 + 4.8 | paraxanthine, theobromine, 7-methylxanthine, xanthine |
| Theophylline | 17.6 + 1.0 | 14.2 + 1.6 | 1- & 3-methylxanthine, xanthine |

*Same products were identified at both conc. of substrates.

Reductase Requirement of Ndm. No N-demethylase activity was observed when purified Ndm was assayed without the Ccr fraction. Ndm is predicted to be a Rieske [2Fe-2S]domain-containing, non-heme iron oxygenase and these types of oxygenases are known to be promiscuous in terms of the partner reductases (Subramanian et al., 1979; Yu et al., 2007). However, Ndm did not function in the presence of the reductase and ferredoxin components of *Pseudomonas* sp. 9816 naphthalene dioxygenase, a well-characterized Rieske [2Fe-2S] domain-containing, non-heme iron oxygenase (Ensley & Gibson, 1983). Likewise, Ndm did not couple with ferredoxin reductase plus ferredoxin from spinach.

Discussion

Figure 4:
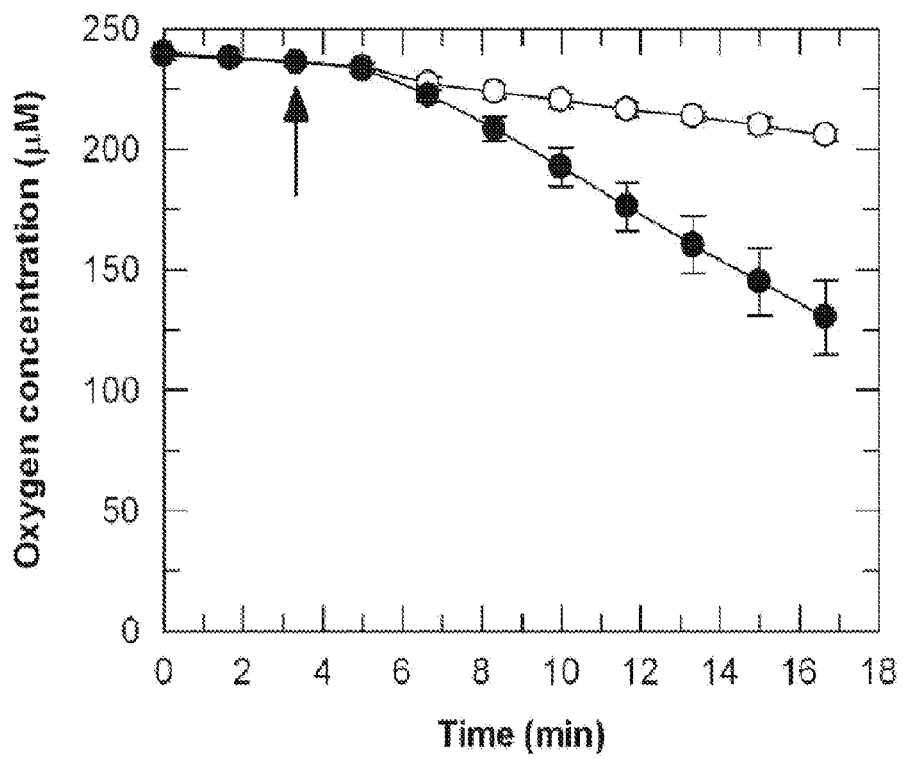
FIG. 4. Oxygen consumption by 0.2 mg of purified Ndm with 4 U of partially purified Ccr with (●) or without (○) 100 μM paraxanthine in the reaction mixture. The reactions were carried out in air-saturated buffer and equilibrated at 30° C. for 3.3 minutes before addition of Ndm plus partially purified Ccr to initiate the reactions (indicated by arrow). Thirteen min after initiation of the reactions, a 100-μL aliquot was withdrawn from the reaction mixture and immediately quantitated for N-demethylation products by HPLC. Concentrations reported were means of 4 replicates with standard deviations.
Figure 5:
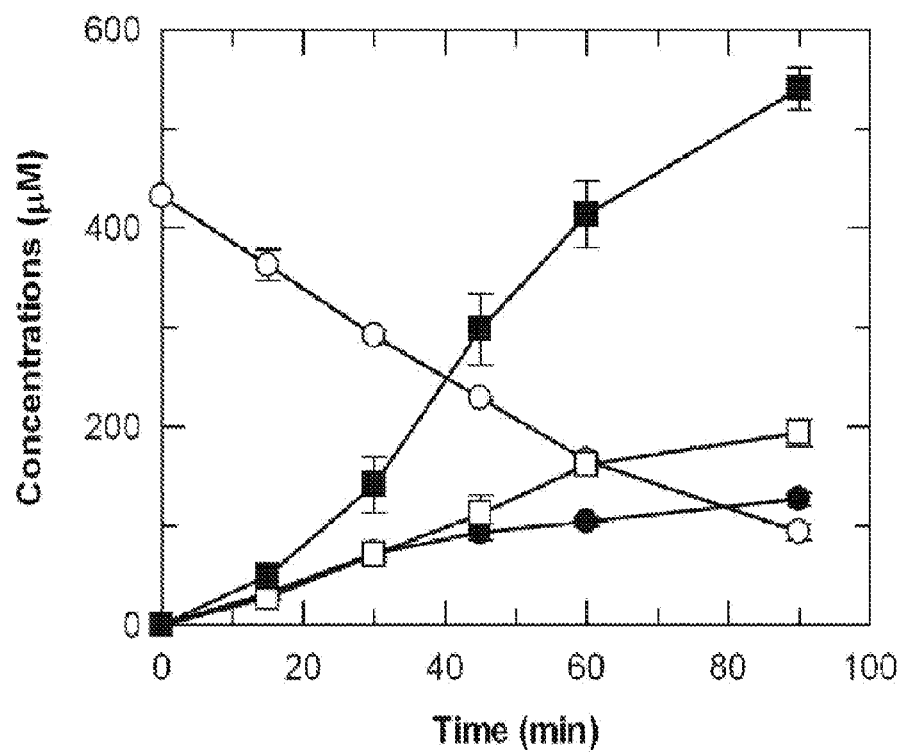
FIG. 5. Stoichiometric N-demethylation of paraxanthine (○), via 7-methylxanthine (●) to xanthine (□) by purified Ndm with concomitant production of formaldehyde (■). Concentrations reported were means of triplicates with standard deviations. Approximately 338.5±7.7 μM of paraxanthine was consumed by 7.4 mU of Ndm in 90 minutes, with the production of 126.9±6.4 μM of 7-methylxanthine, 193.7±14.0 μM xanthine, and 540.6±20.9 μM of formaldehyde.

The first purification and characterization of a broad specificity, soluble I-demethylase from CBB5 is described herein. This enzyme is composed of a reductase component (Ccr) and an oxygenase N-demethylase component (Ndm). The N-demethylase component (Ndm) itself is a two-subunit enzyme with broad substrate specificity. It can remove N-methyl groups from caffeine, all three natural dimethylxanthines, 3-methylxanthine, and 7-methylxanthine (Table 4) to produce xanthine. 7-Methylxanthine was the best substrate for Ndm, with a $k_{cat}/K_M$ value almost six-fold higher than that for paraxanthine. No O-demethylation was observed when vanillate and vanillin were provided as the substrates for Ndm. Enzyme activity of Ndm was absolutely dependent on oxygen as a co-substrate. One molecule of $O_2$ was consumed for each N-methyl group removed from paraxanthine (FIG. 4). N-methyl groups removed from methylxanthines were stoichiometrically oxidized to formaldehyde (FIG. 5). It should be noted that formation of formaldehyde from bacterial N-demethylation of caffeine had been reported previously (Asano et al., 1994; Blecher & Lingens, 1977) but the stoichiometry of the reaction was not established. Whether the formaldehyde produced is utilized by CBB5 needs to be determined.

Figure 2B:
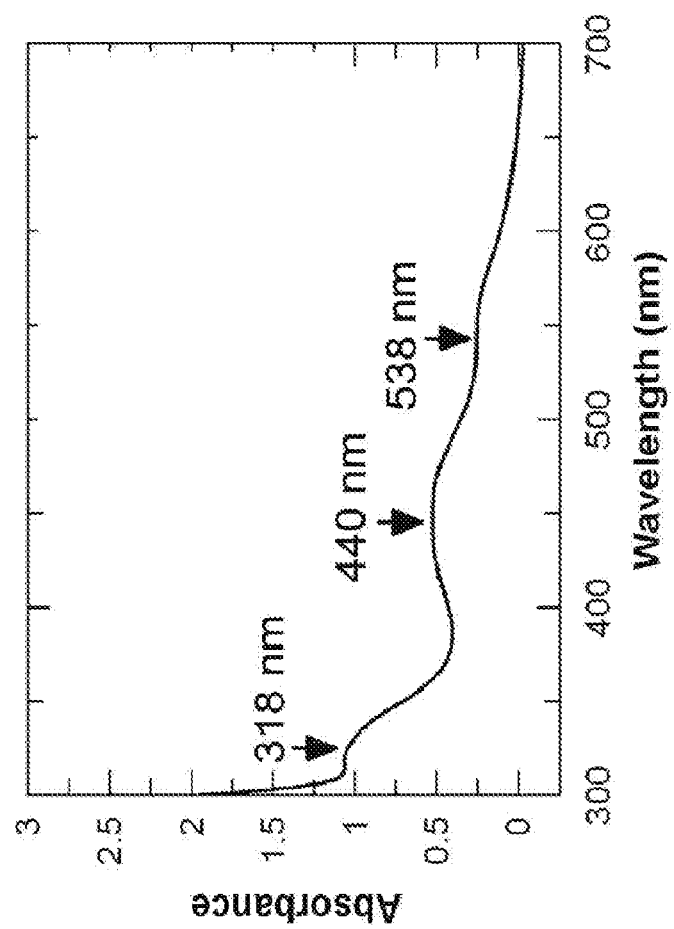
FIG. 2. (A) SDS-PAGE analysis of P. putida CBB5 N-demethylase, Ndm, during the purification process. Molecular masses of markers (in kDa) are shown on the left. Ndm is composed of two subunits with apparent molecular masses of 40 kDa (NdmA) and 35 kDa (NdmB). Lane M, MW marker; lane 1, cell extracts of CBB5 grown on soytone alone; lane 2, cell extracts of CBB5 grown on soytone plus caffeine; lane 3, DEAE-Sepharose eluant; lane 4, Phenyl Sepharose eluant; lane 5, Q-Sepharose eluant. (B) UV/visible absorption spectrum of Ndm (1.7 mg ml$^{-1}$) from Q-Sepharose.
Figure 2A:
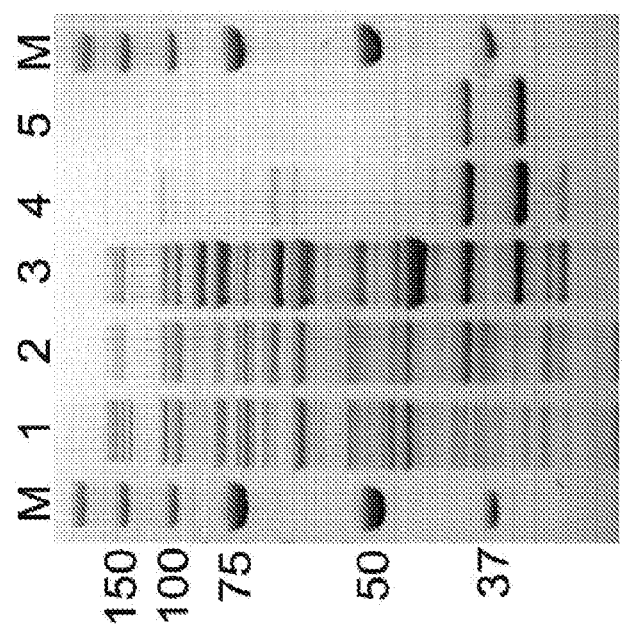

The N-terminal protein sequences of both Ndm subunits were substantially identical to the gene product of an uncharacterized caffeine demethylase gene in *P. putida* IF-3 (Koide et al., 1996) and a hypothetical protein in *Janthinobacterium* sp. Marseille. The physiological functions of these proteins have not been established; however, both of these proteins were predicted to be Rieske [2Fe-2S] domain-containing, non-heme iron oxygenases. UV/visible absorption spectrum of Ndm was characteristic of a protein with a Rieske [2Fe-2S] cluster (FIG. 2B). Exogenous addition of 50 µM $Fe^{2+}$ to the Ndm enzyme reaction mixture stimulated Ndm enzyme activity, similar to other Rieske [2Fe-2S] domain-containing non-heme iron oxygenases such as toluene, naphthalene, and biphenyl dioxygenases (Ensley & Gibson, 1983; Subramanian et al., 1979; Yu et al., 2007). Generally, the mononuclear ferrous iron in Rieske oxygenases is not tightly bound and often dissociates during protein purification. However, it could be reconstituted by incubating the oxygenase with excess $Fe^{2+}$. In fact, after incubating Ndm alone with 1 mM $Fe^{2+}$, iron content of Ndm increased from 8.5 to 20.1 mole/mole hexameric Ndm. Furthermore, Ndm specific activity also increased from 55 mU $mg^{-1}$ to 161 mU $mg^{-1}$. Additional exogenous $Fe^{2+}$ in the enzyme reaction mixture was not absolutely necessary for high Ndm activity. All of these data support the hypothesis that Ndm is a Rieske [2Fe-2S] domain-containing, non-heme iron oxygenase.

Native molecular mass of Ndm was estimated to be 240 kDa by gel filtration chromatography. Meanwhile, both subunits of Ndm, NdmA and NdmB, were approximately 40 kDa in size (FIG. 2A), suggesting Ndm is possibly a hexameric protein. Since 20.1 iron atoms were present per mole of Ndm, it is very likely that NdmA and NdmB each contains 3 iron atoms, in agreement with the presence of a [2Fe-2S] cluster and a mononuclear ferrous iron in each subunit. This finding is intriguing because the mononuclear ferrous iron is known to be the catalytic center of Rieske oxygenases (Ferraro et al., 2005). Both NdmA and NdmB are proposed to contain a mononuclear ferrous iron, which may suggest there are two catalytic centers in native Ndm. However, this remains to be substantiated via cloning of NdmA and NdmB individually. Some Rieske oxygenases are known to be in hexameric $\alpha_3\beta_3$ configuration (Dong et al., 2005; Friemann et al., 2005; Kauppi et al., 1998; Yu et al., 2007) but only the α subunits contain the [2Fe-2S] cluster and the mononuclear ferrous iron, while the β subunits are mainly for structural purposes (Ferraro et al., 2005). The 2-oxo-I,2-dihydroquinoline 8-mono oxygenase of $P.$ $putida$ 86 was reported to be in an $\alpha_6$ configuration, determined by gel filtration chromatography (Rosche et al., 1995), but crystal structure showed that it is actually an homotrimer (Martins et al., 2005). The proposed presence of two catalytic centers in Ndm raises some important questions such as (i) how reducing equivalents generated from the reductase component are distributed between these two catalytic centers (ii) are both catalytic centers functional, and (iii) if they have different or overlapping substrate specificities which in combination account for Ndm substrate preferences. Moreover, the data could not completely exclude the possibility that NdmA and NdmB are individual Rieske oxygenases that co-purify or agglomerate together during purification and each of them could have different or overlapping substrate specificity. Heterologous expression of each subunit separately will answer some of these questions.

Figure 6:
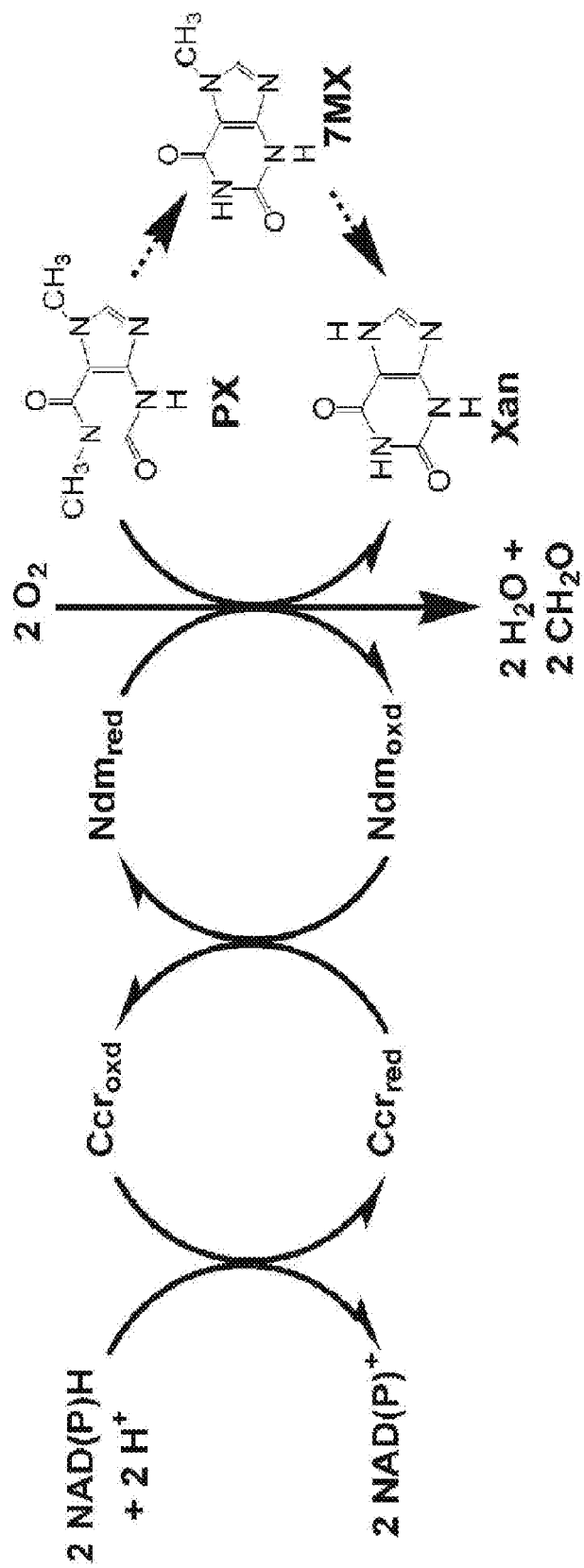
FIG. 6. Proposed reaction scheme for paraxanthine N-demethylation by P. putida CBB5 two-component N-demethylase. Reducing equivalents are transferred from NAD (P)H to the two-subunit N-demethylase component (Ndm) by a specific Ccr. One mole of paraxanthine (PX) is N-demethylated to xanthine (Xan) through 7-methylxanthine (7MX) as an intermediate (dashed arrow).

Ndm enzyme activity was dependent on the presence of a reductase component. This reductase component oxidized NAD(P)H and concomitantly reduced cytochrome c in vitro, hence, it was designated as Ccr (cytochrome c reductase component). The reductases of several well-characterized Rieske, non-heme iron oxygenases are also known to reduce cytochrome c in vitro (Subramanian et al., 1979; Haigler & Gibson, 1990b; Yu et al., 2007). Partially purified Ccr was used for the purification of the Ndm component and the Ccr requirement for N-demethylation by Ndm was specific. Ferredoxins and/or reductases of either spinach or $Pseudomonas$ sp. 9816 naphthalene dioxygenase system (Haigler & Gibson, 1990a; Haigler & Gibson, 1990b) did not support the N-demethylase reaction by Ndm. In contrast, the reductase components of toluene dioxygenase of $P.$ $putida$ (Subramanian et al., 1979) and biphenyl dioxygenase of $Sphingohium$ $yanoikuyae$B1 (Yu et al., 2007) are easily substituted by spinach ferredoxin reductase and the reductase of naphthalene dioxygenase, respectively. A proposed reaction scheme for N-demethylation of paraxanthine (and other methylxanthines) by Ccr plus Ndm is presented in FIG. 6. This scheme is similar to other known microbial mono- and dioxygenases; however, none of the other oxygenases is known to catalyze N-demethylation. A specific Ccr likely transfers electrons to Ndm, where the oxygenase component exhibits broad-based N-demethylation activity on purine alkaloids, thus enabling CBB5 to utilize these substrates. Molecular oxygen is incorporated into formaldehyde and water.

It is not clear whether additional N-demethylases are present in CBB5. Some indirect experiments by others indicate the presence of specific, maybe multiple N-demethylases in caffeine-degrading bacteria. A recent study by Dash & Gummadi (2008) showed that caffeine and theobromine N-demethylases in $Pseudomonas$ sp. NCIM5235 were inducible in nature but caffeine N-demethylase activity in theobromine grown cells was 10-fold lower than that of caffeine grown cells. This implies different N-demethylases for caffeine and theobromine N-demethylation. Glock & Lingens (1998) partially purified a specific 7-methylxanthine N-demethylase from caffeine-degrading $P.$ $putida$ WS, which exhibited no activity on caffeine, theobromine, or paraxanthine. Caffeine and theobromine also did not inhibit 7-methylxanthine N-demethylation by this enzyme. These results also imply multiple N-demethylases in $P.$ $putida$ WS for degradation of caffeine. Finally, multiple N-demethylases were also implied in caffeine-degrading $P.$ $putida$ No. 352 (Asano et al., 1994). Caffeine N-demethylase activity from this strain was partially purified and resolved into three distinct fractions. At the same time, a theobromine N-demethylase activity which produced 7-methylxanthine was reported to co-elute with one of the caffeine N-demethylase fractions. This activity was inhibited by $Zn^{2+}$ while caffeine N-demethylase activities in all three fractions were not. The theobromine N-demethylase was subsequently purified to homogeneity and reported to have a native molecular mass of 250 kDa and a subunit molecular mass 41-kDa (homohexamer). This enzyme was brown in color and displayed an absorbance maxima of 415 nm. Unfortunately, this N-demethylase is not well characterized. Thus, a case could be built that multiple N-demethylases may enable the utilization of purine alkaloids in some bacteria. Nevertheless, Ndm of CBB5 is distinct from all of the above N-demethylase in terms of substrate specificity, UV/visible absorption spectrum, subunit structure, as well as the requirement of a reductase component.

Although the caffeine demethylase gene in $P.$ $putida$ IF-3 (Koide et al., 1996) was predicted to encode a Rieske, non-heme iron oxygenase, the gene function was assigned solely based on reversion of a caffeine-negative phenotype of a mutated strain of $P.$ $putida$ IF-3. Also, the physiological function of this enzyme with respect to the ability of bacteria to utilize purine alkaloids as sole source of carbon and nitrogen is unknown. Naphthalene dioxygenase of $Pseudomonas$ sp. strain 9816 has been reported to N-demethylate N-methylaniline and N,N-dimethylaniline to aniline (Lee, 1995). This reaction is not well characterized and indicates only the promiscuity of naphthalene dioxygenase, and not its physiological role in N-demethylation. This enzyme in fact enables the utilization of naphthalene by converting it to cis-dihydroxy-1,2-dihydronaphthalene (Ensley & Gibson, 1983). To our knowledge, the $P.$ $putida$ CBB5 methylxanthine Ndm provides the first concrete example of a Rieske, non-heme iron oxygenase with broad-based N-demethylase activity on a number of purine alkaloids. N-demethylation (or N-dealkylation) reactions in eukaryotes and prokaryotes are known to be catalyzed only by cytochrome P450s (Abel et al., 2003; Asha & Vidyavathi, 2009; Caubet et al., 2004; Cha et al., 2001; Guengerich, 2001; Tassaneeyakul et al., 1994), various flavo-enzymes (Chang et al., 2007; Kvalnes-Krick & Joms, 1986; Meskys et al., 2001; Nishiya & Imanaka, 1993; Philips et al., 1998; Shi et al., 2004; Wagner, 1982), and a ketoglutarate-dependent non-heme iron oxygenase (Tsukada et al., 2006). This study therefore broadens our understanding of the possible enzymatic mechanism for N-demethylation and will aid the discovery of new microbial N-demethylases in the future.

In summary, Pseudomonas putida CBB5 uses a broad-specificity, two-component N-demethylase system to initiate biotransformation of caffeine and related natural purine alkaloids. The N-demethylation of these compounds is catalyzed by the terminal N-demethylase (Ndm), a two-subunit oxygenase. A specific Ccr component with cytochrome c reductase activity is involved in the transfer of electrons from NADH to the Ndm. N-terminal protein sequences of Ndm subunits were significantly homologous to two proteins predicted to be Rieske [2Fe-2S] domain-containing, non-heme iron oxygenase.

EXAMPLE 3

More than 19,091 natural products and xenobiotics out of approximately 500,000 entries in the Combined Chemical Dictionary database (http://ccd.chemnetbase.com), contain N-methyl groups. N-demethylations of many of these compounds, catalyzed by members of several enzyme families, are critical biological processes in living organisms. For example, humans use cytochrome P450s to N-demethylate a multitude of drugs and xenobiotic compounds (Hollenberg, 1992). N-Demethylation of methylated lysine and arginine residues in histones, important for regulating chromatin dynamics and gene transcription, are mediated by flavin-dependent amine oxidase LSD1(Shi et al., 2004), and JmjC-domain-containing enzymes that belong to the 2-ketoglutarate-dependent non-heme iron oxygenase (KDO) family (Tsukada et al., 2006). The bacterial enzyme AlkB and its human homologs ABH2 and ABH3 (Aas et al., 2003) are also KDOs which catalyze N-demethylation of methylated purine and pyrimidine bases to repair alkylation damages in nucleic acids. The obesity-associated FTO gene is also a KDO which N-demethylates 3-methylthymine (Gerken et al., 2007). Members of the aforementioned enzyme families also catalyze O-demethylation reactions (Hegel et al., 2010). Bacteria have evolved highly substrate-specific Rieske [2Fe-2S] domain-containing O-demethylases that belong to the Rieske oxygenase (RO) family for the degradation of methoxybenzoates (Brunel et al., 1988; Herman et al., 2005). However, there is no description of N-demethylation by ROs.

Caffeine (1,3,7-trimethylxanthine) and related N-methylated xanthines are purine alkaloids that are extensively used as psychoactive substances and food ingredients by humans. Humans metabolize caffeine via N-demethylation catalyzed by the hepatic cytochrome P450s 1A2 and 2E1 (Arnaud, 2011). In contrast, there are very few reports on bacterial utilization of caffeine. Various bacteria have been reported to metabolize caffeine and related methylxanthines by N-demethylation, but nothing is known about the genes and enzymes involved (Dash et al., 2006). Pseudomonas putida CBB5 was recently isolated from soil and is capable of living on caffeine as sole source of carbon and nitrogen (Yu et al., 2009). CBB5 is unique because it completely N-demethylated caffeine and all related methylxanthines, including theophylline (1,3-dimethylxanthine which has not been reported to be metabolized by bacteria), to xanthine.

A novel methylxanthine N-demethylase (Ndm) with broad substrate specificity was purified from CBB5 (Summers et al., 2011; see Example 2). This was characterized as a soluble enzyme composed of two subunits, NdmA and NdmB, with apparent molecular mass of 40 and 35 kDa, respectively. The N-demethylation activity of Ndm, the oxygenase component, was dependent on a specific electron carrier reductase present in CBB5, NAD(P)H and oxygen. Ndm was hypothesized to be a RO based on its reductase dependence, stimulation of activity by exogenous $Fe^{2+}$, UV/visible absorption spectrum, utilization of oxygen as a co-substrate, and homology of the N-terminal amino acid sequences of NdmA and B to two hypothetical ROs. The oxygenase components of all crystallized ROs are either in $\alpha_3$ or $\alpha_3\beta_3$ configurations, with the $\alpha$ subunit being the catalytic subunit and $\beta$ subunit serving a structural purpose (Ferraro et al., 2005). Molecular masses of the $\alpha$ and $\beta$ subunits are approximately 40-50 kDa and 20 kDa, respectively. Both NdmA and NdmB, inseparable by several choromatographic steps, are similar in size to the $\alpha$ subunits of ROs. This led to the hypothesis that they are likely individual N-demethylating ROs with different properties that co-purified from CBB5.

Materials and Methods
Chemicals

Caffeine, theophylline, theobromine, paraxanthine, 1-methylxanthine, 3-methylxanthine, 7-methylxanthine, xanthine, ammonium acetate, acetic acid, 2,4-pentanedione, and bovine cytochrome c were purchased from Sigma-Aldrich (St. Louis, Mo.). Tryptone, yeast extract, and agar were obtained from Becton, Dickinson and Company (Sparks, Md.). NADH, isopropyl β-D-thiogalactopyranoside (IPTG), 5-bromo-4-chloro-3-indolyl β-D-galactopyranoside (X-gal), and Tris Base were obtained from RPI Corp. (Mt. Prospect, Ill.). Restriction enzymes were purchased from New England Biolabs (Ipswich, Mass.). PfuUltra DNA polymerase (Stratagene, Santa Clara, Calif.), Taq DNA polymerase (New England Biolabs), and Phusion HF polymerase (New England Biolabs) were used in various PCR reactions as indicated. PCR primers were purchased from Integrated DNA Technologies (Coralville, Iowa). High-pressure liquid chromatography (HPLC)-grade methanol (J. T. Baker, Phillipsberg, N.J.) was used in all chromatographic studies.

Genomic DNA Libraries Preparation

Plasmid pUC19-Kan, a plasmid with the aph gene that confers kanamycin resistance, was constructed as the vector backbone for genomic DNA libraries. A DNA fragment containing aph was amplified by PCR from pET28a (EMD Biosciences, La Jolla, Calif.) using primers Kan-F and Kan-R (Table 5) plus PfuUltra DNA polymerase. The PCR product was digested with AatII and AvaII, and ligated into pUC19 previously digested with AatII and AvaII, producing pUC19-Kan.

TABLE 5

PCR Primers

| Primer | DNA sequence (restriction enzyme sites are underlined) |
|---|---|
| Kan-F | 5'-AGCTCT<u>GACGTC</u>CTGCGCCTTATCCGGTAACTATCG-3' (SEQ ID NO: 5) |
| Kan-R | 5'-AGCTAG<u>GGTCC</u>AACGTTTACAATTTCAGGTGGCACT-3' (SEQ ID NO: 6) |
| A-degF1 | 5'-ATGGARCARGCNATYATYAA-3' (SEQ ID NO: 7) |
| cdm-rev1 | 5'-CAGCCATTTTCTATACTGGATCGA-3' (SEQ ID NO: 8) |
| ndmA-speF2 | 5'-TACAGTAAGTGGAAACCGCC-3' (SEQ ID NO: 9) |
| ndmA-speF3 | 5'-CAATGTGTCATGTCCGGTAG-3' (SEQ ID NO: 10) |
| Marcy | 5'-CAG GAAACAGCTATGACC-3' (SEQ ID NO: 11) |
| ndmA-speR2 | 5'-GGCGGTTTCCACTTACTGTA-3' (SEQ ID NO: 12) |
| pUC19R | 5'-CATTCAGGCTGCGCAACTGT-3' (SEQ ID NO: 13) |
| pUC19R2 | 5'-GCAGATTGTACTGAGAGTGC-3' (SEQ ID NO: 14) |
| B-degF1 | 5'-ATGAARGARCARCTSAARCC-3' (SEQ ID NO: 15) |
| cdm-rev3 | 5'-AARTCNGTRAARTTYTCCCA-3' (SEQ ID NO: 16) |
| B-iPCR-F2 | 5'-CTGACAAAAGCATCTCTCCTCGGGCCAAGATT-3' (SEQ ID NO: 17) |
| B-iPCR-R2 | 5'-AATCTTGGCCCGAGGAGAGATGCTTTTGTCAG-3' (SEQ ID NO: 18) |
| B-speF3 | 5'-ACAAAAGCATCTCTCCTCGG-3' (SEQ ID NO: 19) |
| B-speF6 | 5'-GGCTGGATAACAGCTTCGAT-3' (SEQ ID NO: 20) |
| B-speR10 | 5'-TTTCCGGCGTTGCTGCAAAC-3' (SEQ ID NO: 21) |
| B-speR11 | 5'-CCAACACCAATTTCTCGCCT-3' (SEQ ID NO: 22) |
| B-speF7 | 5'-TGTGGAAAGATGACTCACGT-3' (SEQ ID NO: 23) |
| B-speF8 | 5'-CGCTAGCCCTGTCGATAACA-3' (SEQ ID NO: 24) |
| ROx-F1 | 5'-TAGAGGATTGCGGTTGACAC-3' (SEQ ID NO: 25) |
| ROx-F2 | 5'-AACGAGTTGCGGTGTCAGTA-3' (SEQ ID NO: 26) |
| pET-ndmA-F | 5'-GCACGG<u>CATATG</u>GAGCAGGCGATCATCAATGATGA-3' (SEQ ID NO: 27) |
| pET-ndmA-R | 5'-GCGCGC<u>GAATTC</u>TTATATGTAGCTCCTATCGCTTT-3' (SEQ ID NO: 28) |
| ndmA-Histag-F | 5'-GCGATAGGAGCTACATATAAGAATTCGAGCTCCGT-3' (SEQ ID NO: 29) |
| ndmA-Histag-R | 5'-ACGGAGCTCGAATTCTTATATGTAGCTCCTATCGC-3' (SEQ ID NO: 30) |
| OE_PCR-F2 | 5'-GAAATAATTTTGTTTAACTTTAAGAAGGAGATATACATATGAAGGAGCAACTGAAGCCGCTGCTAG-3' (SEQ ID NO: 31) |
| OE_PCR-R | 5'-ATCTCAGTGGTGGTGGTGGTGGTGCTCGAGCTGTTCTTCTTCAATAACATTCGTCAAGAC-3' (SEQ ID NO: 32) |
| ndmD-F-NdeI | 5'-GGCCGG<u>CATATG</u>AACAAACTTGACGTCAAC-3' (SEQ ID NO: 33) |
| ndmD-R-HindIII | 5'-GGCCGG<u>AAGCTT</u>TCACAGATCGAGAACGATTT-3' (SEQ ID NO: 34) |

About 28 μg of *P. putida* CBB5 genomic DNA was partially digested by either EcoRI (2.5 units, 8 minutes at 37° C.) or SmaI (5 units, 3 minutes at 25° C.) followed by immediate from the SmaI library for plasmid extraction and 26 were found to contain inserts, with an average size of 5.2 kb. Moreover, 18 out 26 plasmids contained inserts with an internal SmaI heat inactivation. DNA fragments of the two partially digested genomic DNA samples were then resolved on 0.7% agarose gels. DNA fragments of 4- to 8-kb in size were extracted from the gels and ligated into phosphatase-treated, EcoRI- or HincII-digested (because there is a SmaI site inside aph) pUC19-Kan. The two ligations were independently electroporated into ElectoMax DH10B *E. coli* cells (Invitrogen, Carlsbad, Calif.) and plated on LB agar supplemented with 30 μg·mL$^{-1}$ kanamycin, 0.5 mM IPTG and 80 μg·mL$^{-1}$ X-gal. Ligation of the EcoRI-digested fragments and the SmaI-digested fragments into pUC19-Kan resulted in approximately 100,000 and 17,200 white colonies, respectively. Fifteen white colonies were randomly picked from the EcoRI library for plasmid extraction. All of the plasmids contained DNA inserts with an average size of 6 kb. Three out of the 15 plasmids contained inserts with an internal EcoRI site. Thirty white colonies were randomly picked site. Remaining colonies from each library were pooled and plasmid DNA was extracted from the two populations. These 2 plasmid pools were designated as the EcoRI and SmaI gDNA libraries of *P. putida* CBB5.

Cloning and Heterologous Expression of NdmA, NdmB, and NdmD

Forward primer pET-ndmA-F and reverse primer pET-ndmA-R2 (Table 5) were used for PCR amplification of ndmA from CBB5 genomic DNA using PfuUltra DNA polymerase with a thermal profile of 30 s at 95° C., 30 s at 58° C., and 60 s at 72° C. for 30 cycles. The PCR product was digested with NdeI and EcoRI and then ligated into the plasmid pET32a previously digested with NdeI and EcoRI, producing plasmid pET-ndmA. DNA sequencing of pET-ndmA confirmed the cloned ndmA did not have any point mutation resulted from PCR amplification. However for the ease of protein purification, it was desired to produce recombinant NdmA protein as a His-tagged protein. Therefore, a site-directed mutagenesis procedure was carried out using the procedure described in QuikChange II Site-Directed Mutagenesis kit (Stratagene) to remove ndmA stop codon and fused the His$_6$-tag on pET32a to ndmA 3' end. PCR primers ndmA-Histag-F and ndmA-Histag-R (Table 5) were used in this site-directed mutagenesis procedure and the resultant plasmid was designated as pET-ndmA-His. DNA sequencing of pET-ndmA-His confirmed the cloned ndmA Did not have any Point Mutation Resulted from PCR Amplification ndmB was Cloned into pET32a as a C-terminal His-taq Fusion Gene Using the Overlap Extension PCR Procedure Chimeric primers OE_PCR-F2 and OE_PCR-R (Table 5) were used in PCR to amplify ndmB from CBB5 genomic DNA using Taq DNA polymerase, with the thermal profile of 30 s at 94° C., 30 s at 60° C., and 45 s at 72° C. for 30 cycles. The 1.1-kb PCR product was gel-purified and used as a mega primer in a second round of PCR, using 3 ng of pET32a as template and Phusion HF DNA polymerase. The thermal profile was 10 s at 98° C., 30 s at 60° C., and 3.5 minutes at 72° C. for 20 cycles. After completion of the PCR, 20 units of DpnI was directly added to the PCR and incubated at 37° C. for 1 hour. The reaction was then electroporated into electrocompetent *E. Cloni*® 10G cells (Lucigen, Middleton, Wis.) and plasmid pET32-ndmB-His was recovered. DNA sequencing of pET-ndmB-His confirmed the cloned ndmB did not have any point mutation resulted from PCR amplification.

Forward primer ndmD-F-NdeI and reverse primer ndmD-R-HindIII (Table 5) were designed to amplify ndmD from CBB5 genomic DNA using Taq DNA polymerase with a thermal profile of 30 s at 95° C., 30 s at 55° C., and 90 s at 72° C. for five cycles, followed by 30 at 95° C., 30 s at 60° C., and 90 s at 72° C. for 30 cycles. Taq DNA polymerase was used because PfuUltra could not amplify the ndmD. The PCR product was digested with NdeI and HindIII restriction enzymes and then ligated to pET28a which was previously digested with NdeI and HindIII, resulting in plasmid pET28-His-ndmD. DNA sequencing of pET28-His-ndmD confirmed integration of ndmD into the plasmid as an N-terminal His-tag fusion gene without any mutations.

Plasmid pET32-ndmA-His, pET32-ndmB-His, and pET28-His-ndmD were individually transformed into *E. coli* BL21(DE3) for over-production of recombinant proteins. Expression of ndmA-His and ndmB-His was carried out in the same manner. The cells were grown in LB broth with 100 μg·mL$^{-1}$ ampicillin at 37° C. with agitation at 250 rpm. When the cell density reached an OD$_{600}$ of 0.5, sterile FeCl$_3$ was added to the culture at a final concentration of 10 μM and the culture was shifted to 18° C. for incubation. IPTG at a final concentration of 0.1 mM (for ndmA) or 1 mM (for ndmB) was added to induce gene expression when the OD$_{600}$ reached 0.8-1.0. Induced cells were then incubated at 18° C. for 18 hours and harvested by centrifugation. Cells were stored at −80° C. prior to lysis.

Expression of His-ndmD was carried out in similar manner, with minor modifications. Cells were grown in Terrific Broth with 30 μg·mL$^{-1}$ kanamycin at 37° C. with agitation at 250 rpm. When the cell density reached an OD$_{600}$ of 0.5, sterile FeCl$_3$ and ethanol were added to the culture at final concentrations of 10 μM and 0.1% (v/v), respectively, and the culture was shifted to incubation at 18° C. When the OD$_{600}$ of the culture reached 0.8, IPTG was added to a final concentration of 0.2 mM. The culture was incubated at 18° C. for 18 hours and harvested by centrifugation. Cells were stored at −80° C. prior to lysis.

Purification of His-taqged NdmA, NdmB, and NdmD

About 5.2 g frozen cells containing NdmA-His$_6$ and 4.2 g cells containing NdmB-His$_6$ were thawed and each suspended to a final volume of 30 mL in 25 mM potassium phosphate (KP$_i$) buffer (pH 7) containing 10 mM imidazole and 300 mM NaCl. Similarly, 40.3 g frozen cells containing His$_6$-NdmD were suspended to 100 mL in the same buffer. Cells were lysed by passing twice through a chilled French press at 138 MPa. The lysates were centrifuged at 30,000×g for 20 minutes and the supernatants were saved as cell extracts for purification of NdmA-His$_6$, NdmB-His$_6$, and His$_6$-NdmD.

Cell extracts containing soluble enzyme were purified on a 40-mL (bed volume) Ni-NTA column (GE Healthcare) at a flow rate of 5 mL·min$^{-1}$ at 4° C. using an AKTA Purifier FPLC system. The column was pre-equilibrated in binding buffer consisting of 300 mM NaCl and 10 mM imidazole in 25 mM KP$_i$ buffer (pH 7). Thirty mL of cell extracts containing NdmA-His$_6$ or NdmB-His$_6$ and 80 mL cell extract containing His$_6$-NdmD were passed through the Ni-NTA column to allow for binding of His-tagged proteins. Unbound protein was washed from the column with 200 mL binding buffer. Bound protein was then eluted with 120 mL elution buffer consisting of 300 mM NaCl and 250 mM imidazole in 25 mM KP$_i$ buffer (pH 7) and concentrated using Amicon ultrafiltration units (MWCO 30,000). Each concentrated enzyme solution was dialyzed (MWCO 10,000) at 4° C. four times against 1 50 mM $KP_i$ buffer (pH 7.5) with 5% (v/v) glycerol and 1 mM DTT (KPGD buffer) with 3 changes of dialysis buffer within 24 hours to remove imidazole. All purified enzymes were stored short-term on ice and at –80° C. for long term storage.

Enzyme Activity Assays

NADH:cytochrome c oxidoreductase activity was determined as described by Ueda et al. (1972). A typical 1-ml reaction in 50 mM $KP_i$ buffer (pH 7.5) contained 300 µM NADH, 87 µM bovine cytochrome c (type III; Sigma), and 1.8 µg of partially purified reductase from CBB5 or 0.2 µg of purified $His_6$-NdmD. The activity was determined by monitoring the increase in absorbance at 550 nm due to reduction of cytochrome c at 30° C. An extinction coefficient of 21,000 $M^{-1} cm^{-1}$ for reduced minus oxidized cytochrome c was used for quantitating the activity. One unit of activity was defined as one pmol of cytochrome c reduced per minute.

Methylxanthine N-demethylase activity assay contained, in 1-ml total volume, 0.5 mM methylxanthine, 1 mM NADH, 50 µM $Fe(NH_4)_2(SO_4)_2$, and an appropriate amount of $NdmA-His_6$ or $NdmB-His_6$ (7.4 µg-2.5 mg protein depending on substrate specificity) in 50 mM $KP_i$ buffer (pH 7.5). Approximately 4 U of partially purified reductase, prepared as described previously (Summers et al., 2011) or 59 U of purified $His_6$-NdmD was added to reaction mixture. Catalase from bovine liver (4,000 U) was also added to reactions containing $His_6$-NdmD. The reaction mixture was incubated at 30° C. with 300 rpm shaking on an incubating microplate shaker (VWR, Radnor, Pa.). Periodically, a small aliquot was sampled from the reaction mixture and mixed with equal volume of acetonitrile for quantifying concentrations of methylxanthines and N-demethylated products by HPLC. One unit of N-demethylase activity was defined as the consumption of one pmole methylxanthine per minute.

Molecular Mass Estimation

The molecular mass of the $NdmA-His_6$, $NdmB-His_6$, and $His_6$-NdmD were estimated under denaturing conditions by PAGE on 10% Bis-Tris gels with MOPS running buffer containing SDS (Invitrogen, Carlsbad, Calif.). Native molecular masses of these His-tagged proteins were determined by gel filtration chromatography using an 80-ml ($V_s$, geometrical volume) Sephacryl S-300 HR column (Amersham) equilibrated with 0.1 M KCl in 50 mM $KP_i$ buffer at 1 ml $min^{-1}$. Void volume ($V_o$) of the column was determined by measuring the elution volume ($V_e$) of a 1 mg $ml^{-1}$ solution of blue dextran 2000 (GE Healthcare). The column was calibrated with ferritin (440 kDa), catalase (232 kDa), adolase (158 kDa), and conalbumin (75 kDa). The $V_e$ of each standard protein was measured, from which the respective $K_{av}$ value was calculated according to the equation $$K_{av} = \frac{V_e - V_o}{V_c - V_o}.$$

A standard curve of $K_{av}$ values against the logarithmic molecular masses of the standard proteins was then used to determine the native molecular mass of Ndm.

Determination of Kinetic Parameters

Apparent kinetic parameters of $NdmA-His_6$ and $NdmB-His_6$ were determined by measuring the initial rate of disappearance ($v_o$) of methylxanthines in 50 mM KPi buffer (pH 7.5) at 30° C. The initial substrate concentrations (ESI) used in these experiments were from 25 to 500 µM. Substrates were incubated with $His_6$-NdmD plus either $NdmA-His_6$ or $NdmB-His_6$ under standard conditions for 15 minutes. At 1, 5, 10, and 15 minutes, samples were removed from the reaction mixtures to quantitate substrate concentrations by HPLC. Plots of substrate concentrations against time were used to determine the initial rates of disappearance of substrates which were linear over 15 minutes. The apparent kinetic parameters were determined from Michaelis-Menten plots of $v_o$ against [S] fitted with the equation $$v_o = \frac{k_{cat}[E_T][S]}{K_M + [S]},$$

where $[E_T]$ is the concentration of enzyme in the reaction. All of the experiments were performed in triplicate and the data were analyzed by using GraFit 5.0 software (Erithacus Software Limited, Surrey, United Kingdom).

Determination of Oxygen Requirement

Oxygen consumptions by $NdmA-His_6$ and $NdmB-His_6$ during N-demethylation of caffeine and theobromine, respectively, were determined in a closed reaction vessel equipped with a Clarke-type oxygen electrode (Digitial Model 10, Rank Brothers Ltd., Cambridge, England). The electrode was calibrated by using glucose oxidase (Sigma) and glucose for consumption of oxygen. Enzyme activity assay was performed at 30° C. in a total volume of 1.2 mL of air-saturated 50 mM KPi buffer (pH 7.5) with 200 µM caffeine (or theobromine), 200 µM NADH, 50 µM $Fe(NH_4)_2(SO_4)_2$, 4,000 U catalase, 295 µg $NdmA-His_6$ or 627 µg $NdmB-His_6$, and 49 U $His_6$-NdmD. The reaction was initiated by adding $NdmA-His_6$ (or $NdmB-His_6$) plus $His_6$-NdmD after equilibration of all other reaction components for 5 minutes. After 5.5 minutes, a 120-µL aliquot was withdrawn from the reaction, immediately mixed with equal volume of acetonitrile to stop the enzyme reaction, and analyzed for N-demethylation product by HPLC. Background oxygen consumption was quantitated in control reactions containing all reaction components except the methylxanthine substrate.

Formaldehyde Determination

Production of formaldehyde during N-demethylation of caffeine by $NdmA-His_6$ and theobromine by $NdmB-His_6$ was determined by derivatizing formaldehyde with Nash reagent prepared by the method of Jones et al. (1999). Twenty µL Nash reagent was added to 50 µl $NdmA-His_6$ or $NdmB-His_6$ reaction sample plus 50 µl acetonitrile. This mixture was incubated at 51° C. for 12 minutes. After cooling to room temperature, 3,5-diacetyl-1,4-dihydrolutidine formed from formaldehyde and Nash reagent was analyzed at 412 nm by a HPLC equipped with a photodiode array detector. Standards were prepared with known concentrations of formaldehyde added to control enzyme reaction mixtures without the methylxanthine substrates.

Analytical Procedures

Identification and quantification of methylxanthines and their metabolites were conducted with a Shimadzu LC-20AT HPLC system equipped with a SPD-M20A photodiode array detector and a Hypersil BDS C18 column (4.6 by 125 mm) as described. For analysis of 3,5-diacetyl-1,4-dihydrolutidine, methanol-water-acetic acid (30:20:0.5, v/v/v) was used as an isocratic mobile phase at a flow rate of 0.5 ml $min^{-1}$. Protein concentration was determined by the Bradford method[8] using bovine serum albumin as the standard with a dye reagent purchased from Bio-Rad. Iron content in $NdmA-His_6$ and $NdmB-His_6$ was determined by ICP-MS. An aliquot of purified $NdmA-His_6$ and $NdmB-His_6$ was mixed with equal volume of trace metal-free, ultrapure concentrated nitric acid.

The mixture was heated at 160° C. for 1 hour to breakdown all organic materials. The acid digest was then diluted appropriately with ultrapure water for quantification of iron by a Thermo X-series II ICP-MS system at the Department of Geosciences, University of Iowa. The ICP-MS system was calibrated with high purity iron standard solution. Bovine cytochrome c was used as positive control. Acid-labile sulfur content in enzyme was determined colorimetrically using the N,N-dimethyl-p-phenylenediamine assay (Suhara et al., 1975).

TABLE 6

Deduced function of each Ndm ORF.

| Gene | Size (amino acids) | Database used in BlastP serach | Homologous protein | GenBank accession number | % Identity[a] | Proposed function |
|---|---|---|---|---|---|---|
| orf1 | 331 | NR | Janthinobacterium sp. Marseille mma_0222 | YP_001351912 | 48 | AraC family transcription regulator |
| | | SwissProt | Sinorhizobium meliloti GlxA | O87389 | 20 | |
| orf2 | 370 | NR | Pseudomonas mendocina NK-01 MDS_2843 | YP_004380626 | 90 | Glutathione-dependent formaldehyde dehydrogenase |
| | | SwissProt | Synechocystis. sp. PCC 6803 FrmA | NP_440484 | 72 | |
| orf4 | 263 | NR | P. putida TJI-51 G1E_06918 | EGB99698 | 53 | Putative outer membrane protein |
| | | SwissProt | Vibrio parahaemolyticus OmpK | P51002 | 18 | |
| orf5 | 220 | NR | Janthinobacterium sp. Marseille mma_3679 | YP_001355369 | 63 | GntR family transcriptional regulator |
| | | SwissProt | Bacillus subtilis YdhC | O05494 | 21 | |
| orf7 | 447 | NR | Janthinobacterium sp. Marseille mma_PbuX7 | YP_001355365 | 65 | Methylxathine transport |
| | | SwissProt | E. coli K-12 YgfU | Q46821 | 51 | |
| orf8 | 361 | NR | Pseudomonas sp. TJI-51 G1E_06893 | EGB99693 | 67 | Protein with conserved domain belongs to pfam01261; no proposed function |
| | | SwissProt | Not found | — | — | |
| orf9 | 284 | NR | Pseudomonas sp. TJI-51 G1E_06898 | EGB99694 | 57 | Unknown |
| | | SwissProt | Chlamydomonas reinhardtii CAO | Q9ZWM5 | 17 | |

[a]% identity was determined by aligning the gene product of each orf with the homologous protein using ClustalW2 (http://www.ebi.ac.uk/Tools/msa/clustalw2/).

ndmA
(SEQ ID NO: 37)

```
ATGGAGCAGGCGATCATCAATGATGAACGGGAGTATCTTCGCCATTTCTGGCATCCCG

TATGTACTGTAACTGAGCTTGAAAAGGCGCATCCTTCCAGCCTCGGCCCCCTGGCCGT

TAAGCTGCTGAATGAACAGCTCGTTGTCGCCAAGCTAGGCGATGAGTACGTCGCGATG

CGTGATAGATGCGCTCATCGATCAGCTAAGCTTTCCTTGGGTACAGTAAGTGGAAACC

GCCTACAGTGCCCCTATCACGGATGGCAATATGATACGCATGGCGCTTGCCAGCTCGT

ACCAGCGTGCCCCAACAGCCCAATACCCAACAAGGCTAAAGTTGATCGCTTCGATTGC

GAAGAACGCTATGGATTGATTTGGATTCGATTGGACTCTAGTTTTGACTGCACTGAAAT

TCCCTACTTTAGTGCAGCCAACGATCCTAGGTTGCGTATTGTTATACAAGAACCTTACT

GGTGGGATGCGACTGCAGAACGTAGATGGGAAATTTTACAGATTTTTCTCACTTTGCA

TTCATTCACCCAGGCACGCTTTTCGATCCAAATAATGCTGAACCTCCAATTGTTCCGAT

GGATCGATTCAATGGTCAGTTTCGGTTTGTCTACGACACGCCAGAAGATATGGCTGTC

CCAAATCAGGCTCCAATTGGTTCATTTTCGTATACTTGCAGCATGCCGTTTGCTATTAA
```

```
CCTTGAAGTATCCAAATACTCCAGCAGTTCGCTGCATGTGTTATTCAATGTGTCATGTC

CGGTAGACAGCCACACCACGAAAAACTTTCTGATCTTCGCTAGGGAGCAATCGGACGA

CTCGGATTATCTGCACATTGCATTTAATGATCTCGTCTTCGCTGAAGACAAACCAGTAA

TTGAGTCCCAATGGCCTAAAGACGCGCCAGCAGATGAGGTCTCAGTAGTCGCAGATAA

GGTATCGATACAATATAGAAAATGGCTGCGGGAACTAAAAGAAGCTCATAAAGAAGGT

TCACAAGCCTTCCGAAGTGCTTTGTTAGACCCAGTCATTGAAAGCGATAGGAGCTACA

TATAA
``` ndmB (SEQ ID NO: 38)
```
ATGAAGGAGCAACTGAAGCCGCTGCTAGAAGACAAGACTTACCTTCGCCACTTCTGGC

ATCCCGTGTGTACCCTTAATGAATTCGAACGCGCCAACGCCAGTGGGCACGGCCCCA

TGGGCGTCACCTTGCTAGGCGAGAAATTGGTGTTGGCCAGGTTAAATTCAAAGATCAT

TGCGGCTGCTGACCGATGTGCTCATCGATCGGCACAGCTCTCCATCGGCCGCGTTTG

CAGCAACGCCGGAAAGGACTATCTCGAATGCCCGTATCACGGCTGGCGCTACGATGA

GGCTGGGGCCTGTCAACTGATCCCTGCTTGCCCTGACAAAAGCATCTCTCCTCGGGC

CAAGATTTCCTCATTCGATTGTGAGGTGAAATACGACATCGTGTGGGTACGGCTGGAT

AACAGCTTCGATTGCACTCAGATTCCATACCTCAGCGATTTCGATAATCCCGACATGCA

GGTAATCGTTGCCGATTCGTATATTTGGGAGACTGTTGCCGAGCGGCGGTGGGAGAA

CTTTACAGATTTTTCGCACTTTGCCTTCGTACACCCAGGGACGCTCTATGATCCGTTTT

TCGCTAGCCACCCAACTGTTTACGTGAATCGCGTTGATGGTGAGTTGCAATTCAAACTT

GCTCCGCCGCGTGAAATGAAAGGCATCCCGCCAGAAGCACCGATGGGTGACTTCACC

TACCGCTGCACAATGCCGTATTCAGTAAATCTTGAAATCAAATTGTGGAAAGATGACTC

ACGTTTCGTTCTTTGGACTACCGCTAGCCCTGTCGATAACAAGTCTTGCCGGAATTTTA

TGATTATTGTGCGTGAGAAGGATAACCAACCTGATCATATGCACCTGGCTTTCCAGAAG

CGGGTGCTTGACGAAGACCAGCCTGTTATCGAATCGCAATGGCCTCTCGAAATACAGA

CCTCGGAAGTCTCCGTTGCAACCGATAAAATTTCCGTCCAGTTCCGCAAATGGCATAA

AGAGCTATCTCTGTCAGCCGTTGAAGGACGGGAGGCGTTCCGCGATTCCGTCTTGAC

GAATGTTATTGAAGAAGAACAGTAA
``` ndmC (SEQ ID NO: 39)
```
ATGTCTACTGACCAAGTAATTTTTAACGACTGGCATCCAGTCGCTGCTTTGGAAGATGT

ATCTCTCGATAAACGATACCGCTGTCGACTACTAGGTCGTACAGTTAGTTATGTGAAAA

CATCTGATGCTGTTAATGCTCATTGGAAGAAAGTGCAGATGAAATTAAGACCATCCGC

GCTAAAGAAATCTATGGTCTTCTGTGGCTCTCCTTTGCCGACAAACCCAGTGAGATGTT

CGATATTGCAGAGTTCAAGGAACCTGATCGCCGAATCGTCAGCGCTGGATCTGTGCGC

GTAAATGTCTCAGGACTGCGTGCTATCGAAAACTTTCTGGACATGGCTCATTTCCCTTT

TGTTCATACGGATATTTTGGGTGCAGAGCCACTGACGGAAGTTGAGCCGTATAACGTC

AACTATGATGAAACTGTTGATGAGATCTTCGCTACTGAGTGTAAGTTCCCGCAACCTAA

AGGCTCAGCTACTGCTGTCGAGCCAATTGATATGCAGTATATATACCGCATTACACGG

CCATATTCCGCCATTTTATATAAAACTTGCCCGCCCGAACCGCATAGATGGGATGCCCT

CGGTCTGTTTATTCAACCTGTAGACGAAGATTGGTGCATAGCGCATACAATTATGTGCT

ATGTGGATGACGTTAACTCAGATCAACAACTTCGCCATTTCCAGCAGACGATTTTTGGC
```

```
CAGGACTTGATGATTCTTATCAACCAAGTTCCAAAGCGTCTTCCCCTGGCTGCAAGTC

GAGAGAGCCCAGTCCGGGCCGATGTGCTTGCAACAGCTTATCGTCGCTGGCTGCGTG

AGAAAGGTGTGCAATATGGTGCTCTGCGGGACTAA
``` ndmD (SEQ ID NO: 43)
```
ATGAACAAACTTGACGTCAACCAGTGGTTTCCTATTGCTACCACTGAAGATCTCCCGAA

GCGCCATGTCTTTCATGCCACGTTGTTGGGGCAAGAAATGGCCATCTGGCGCGATGA

CTCTGGTTCAGTTAATGCTTGGGAGAACCGCTGCCCGCATAGAGGATTGCGGTTGACA

CTGGGTGCTAATACCGGTAACGAGTTGCGGTGTCAGTATCATGGATGGACTTATGAAA

GCGGGACTGGTGGCTGCACTTTTGTCCCAGCCCATCGCGATGCACCACCCCCAAATG

CCGCGCGGGTTAATACTTTTCCTGTCCGCGAAAAGCACGGCTTTATCTGGACGACATT

AGGTCAGCCGCCAGGAGAGCCCATTTCAATCCTCGATGACGCTCAGCTTGTAAACGCT

GTAAAAACAAATCTGCATAGCGTAGTTATAGATGCTGATATTGACGGAGTTGTCAGCGT

CCTACGTCAGAATCTTTCAGCGTTCATCGATGTGTTTGGTGCGGCCAGCGCTGAAGAT

CTGCATTTGAAATCCATGCTGCAAGATCGAGGGATTCTGGTAACAAGATCAGGCTCTAT

TGCTATTCATTTTTATATGCAGCGCTCAACCATTAGTAAATGCGTTGTACATGCGCAAG

TACTTACTCCGGGACGTCCAGGATACGAACTTCAAAAGAACTACTCGTATGCCATGAA

CGTTATCCGCAGGGCAGCAGAAGCTGTAGCTACCGACTTGATTAGCATTACAGATATC

AGCGATCAGACTATCGAAAAGCTTGAAGTCGTTAGAGAAAACATGACTAAGGCTCCTC

CAACCCACTATATCTGCGAAGTGGTTACGCGTACTCAAGAGACAGGTGATATTAACTCA

TACTGGCTGAAGCCTATCGGCTACCCACTACCAGCATTCAGTCCAGGGATGCACATCA

GCATCACAACGCCGGAGGGTAGCATTCGACAATATTCCCTCGTGAACGGGCCTGACG

AGCGTGAATCCTTCATCATCGGTGTGAAGAAAGAGATTCAGTCCCGTGGCGGCTCCAG

ATCAATGCACGAAGATGTGAAGGTTGGAACGCAACTAAAAGTTACACTTCCGAGGAAC

GGTTTTCCACTCGTCCAAACCAGAAAACACCCGATTCTCGTAGCAGGTGGCATCGGTA

TCACCCCAATTTTGTGTATGGCACAGGCTCTGGATCAGCAAGGTTCATCGTATGAAATA

CATTATTTTGCTCGTGCATTTGAGCATGTTCCATTCCAGGATCGACTGACTGCGTTGGG

CGATCGTTTGAATGTGCATCTTGGCCTCGGCCCAGACGAGACTAGAGCAAAACTTCCC

GACATCATGGAGATTCATAACGCCCAAGACGTAGATGTTTACACTTGCGGCCCGCAAC

CAATGATCGAAACTGTATCTGCTGTCGCTCTTGCTCATGGCATCGCTGAAGAGTCCAT

CCGATTTGAATTTTTCAGTAAAAAGAACGATGTTCCCGTTTCTGATGAAGAATATGAGG

TTGAGCTCAAAAAAACTGGTCAAATATTCACTGTCTCGCCTGGCTCTACGTTGTTGCAA

GCTTGTTTGGACAACGATGTTCGTATCGAAGCTTCTTGTGAGCAGGGTGTATGCGGGA

CTTGTATAACTCCAGTCGTATCCGGCGATCTCGAGCATCATGACACTTACCTTTCTAAG

AAAGAAAGGGAAAGCGGTAAGTGGATCATGCCGTGTGTTTCGCGCTGCAAGTCCAAAA

AAATCGTTCTCGATCTGTGA
```

Results

The N-terminal amino acid sequence of NdmA was MEQAIINDEREYLRHF?HPVVTVTE, as determined by Edman degradation (Summers et al., 2011). Using the N-terminal amino acid sequence as a query in a BlastP search (Altschul et al., 1997), the gene product of a hypothetical caffeine demethylase gene (cdm) in U.S. Pat. No. 5,550,041 and a hypothetical protein in *Janthinobacterium* sp. Marseille (mma_0224, GenBank accession no. YP_001351914) were found to be homologous to NdmA with E-values in the range $10^{-23}$. Cdm was aligned with the hypothetical gene that encoded mma_0224 and a specific reverse PCR primer cdm-rev1 (Table 5) was designed from a conserved region near the 3' ends of these 2 genes. By using cdm-rev1 together with a forward degenerate primer A-degF1 (Table 5) that was designed from amino acid residues 1 to 7 of NdmA (MEQAIIN), an approximately 1-kb PCR product (FIG. 7A, fragment a) was amplified from CBB5 genomic DNA using Taq DNA polymerase and a thermal profile of 30 s at 95° C., 30 s at 55° C., and 45 s at 72° C. for 5 cycles, followed by 30 s at 95° C., 30 s at 58° C., and 45 s at 72° C. for 25 cycles. Control PCR reactions using either primer alone or without genomic DNA in PCR reactions yielded no PCR product. This PCR product was cloned into vector pGEMT-easy (Promega, Madison, Wis.), and three clones were randomly chosen for DNA sequencing. This PCR product was also gel-purified and directly sequenced. Results from DNA sequencing showed that the inserts in the three pGEMT-easy clones were 963 bp in length and were identical to the results generated from direct DNA sequencing of the PCR product. An incomplete ORF was identified within this 963 bp of DNA. The deduced N-terminal protein sequence of this incomplete ORF was MEQAIINDEREYLRHFWH-PVCTVTE (SEQ ID NO:35), almost completely matched NdmA N-terminal protein sequence determined by Edman degradation. A stop codon was missing from this incomplete ORF. Since NdmA was about 40 kDa in size, it was estimated that approximately 100-120 nucletoides near the 3' end of ndmA were missing.

Figure 7A:
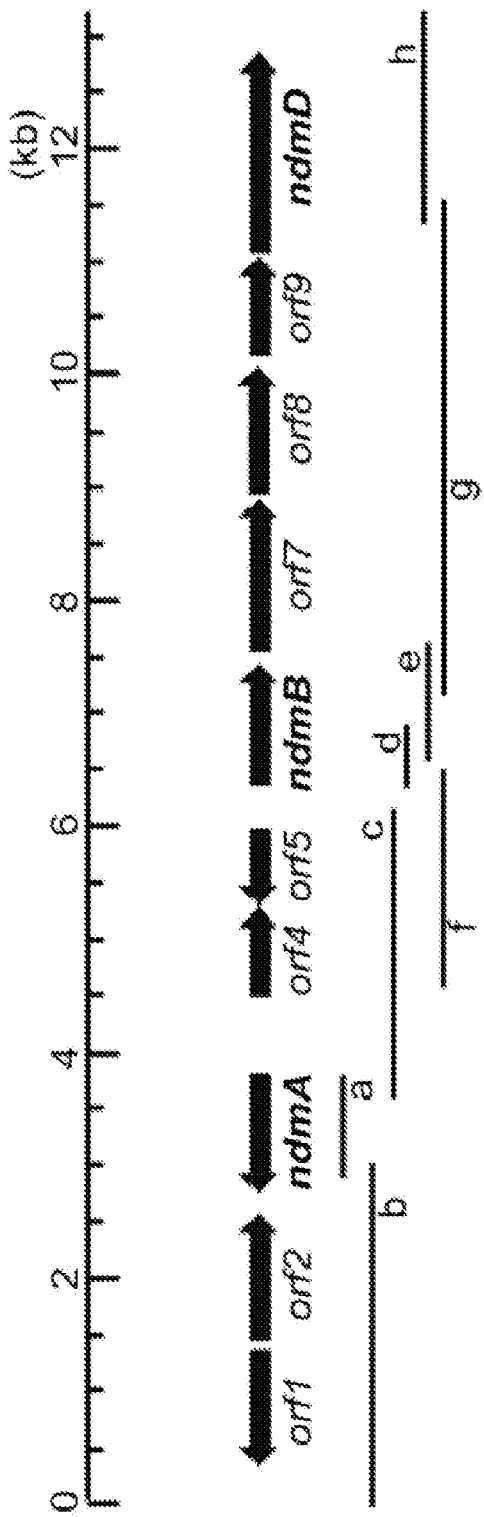
FIG. 7. A 13.2-kb gene cluster in P. putida CBB5 containing genes that catalyze N-demethylation of methylxanthines. (A) Organization of the ndm genes and various ORFs. Black arrows indicate the position and direction of each ORF. The black lines (labeled a to h) represent the 8 overlapping PCR products used to assemble this map. Functions of ndmA, ndmB, and ndmD are discussed in this report. (B) Schematic organization of conserved domains identified in the deduced protein sequence of ndmD. Designations: [2Fe-2S]$_R$, Rieske [2Fe-2S] domain; [FAD/FMN], flavin dinucleotide or flavin monophosphate-binding domain; [NADH], reduced nicotinamide adenine dinucleotide binding domain; [2Fe-2S]$_{Fd}$, plant-type ferredoxin [2Fe-2S] domain. (C) Schematic organization of the 14.8 kb gene cluster in P. putida CBB5 containing genes that catalyze N-demethylation of methylxanthines. (D) Substrate specificity of NdmA-His$_6$. (E) Substrate specificity of NdmB-His$_6$. (F) Activity of NdmABCDE in the caffeine and theophylline metabolic pathways. (G) Specificity of NdmA and NdmB.
Figure 7B:

A nested PCR approach was used to amplify the missing 3' end of ndmA as well as DNA that flanked ndmA. Two new specific forward primers, ndmA-speF2 and ndmA-speF3, and a specific reverse primer, Marcy (Table 5), were respectively designed from the incomplete ndmA ORF and the vector backbone of pUC19-Kan. Using primers ndmA-speF2 plus Marcy, a primary PCR reaction was run using the EcoRI gDNA library as template with Taq DNA polymerase and a thermal profile of 30 s at 95° C., 30 s at 58° C., and 3 min at 72° C. for 30 cycles. Then, 0.5 μL of the primary PCR product was used as template in a second round of PCR with primers ndmA-speF3 plus Marcy and Taq DNA polymerase. A thermal profile of 30 s at 95° C., 30 s at 60° C., and 3 min at 72° C. for 30 cycles was used. An approximately 3-kb PCR product was amplified in this second round of PCR (FIG. 7A, fragment b). Control PCR reactions using either ndmA-speF3 or Marcy alone or without the primary PCR product as template did not yield this 3-kb PCR product. This 3-kb PCR product was gel-purified and sequenced directly. The missing 3' end of ndmA was identified when this 3-kb PCR product was sequenced using primer ndmA-speF3. In addition, two ORFs were also identified 3' to ndmA in this 3-kb PCR product and were designated as orf1 and orf2 (FIG. 7A).

A similar nested PCR approach was used to amplify the DNA 5' to ndmA. A specific reverse primer ndmA-speR2 was designed from ndmA and 2 specific forward primers pUC19R and pUC19R2 (Table 5) were designed from the vector backbone of pUC19-Kan. Using primers pUC19R2 plus cdm-rev1, a primary PCR reaction was run using the EcoRI gDNA library as template with Taq DNA polymerase and a thermal profile of 30 s at 95° C., 30 s at 60° C., and 3 minutes at 72° C. for 30 cycles. Then, 0.5 μL of the primary PCR product was used as template in a second round of PCR with primers ndmA-speR2 plus pUC19R and Taq DNA polymerase. A thermal profile of 30 s at 95° C., 30 s at 60° C., and 3 minutes at 72° C. for 30 cycles was used. An approximately 3-kb PCR product was amplified in this second round of PCR (FIG. 7A, fragment c). Control PCR reactions using either ndmA-speR2 or pUC19R alone or without the primary PCR product as template did not yield this 3-kb PCR product. This 3-kb PCR product was gel-purified and sequenced directly. This PCR product contained the 5'-half of ndmA and two complete ORFs (orf4 and orf5) 5' to ndmA (FIG. 7A).

The N-terminal amino acid sequence of NdmB was MKEQLKPLLEDKTYLRHFWHPVVTL (SEQ ID NO:36) (Summers et al., 2011) and was also homologus to cdm gene product and mma_0224 in *Janthinobacterium* sp. Marseille genome, with E-values in the range $10^{-25}$. A forward degenerate primer, B-degF1 (Table 5), was designed from amino acid residues 1-7 of NdmB (MKEQLKPL). When B-degF1 was used together with the specific reverse PCR primer cdm-rev1 primer designed from an alignment of cdm and the gene encoding mma_0224, no PCR product could be amplified from genomic DNA of CBB5. Therefore, another degenerate reverse PCR primer, cdm-rev3 (Table 6), was designed from the alignment of cdm plus the gene encoding mma_0224. Primer cdm-rev3 was located around the center of both hypothetical genes. Using B-degF1 with cdm-rev3, an approximately 500-bp PCR product (FIG. 7A, fragment d) was amplified from CBB5 genomic DNA using Taq DNA polymerase, with a thermal profile of 30 s at 95° C., 30 s at 55° C., and 45 s at 72° C. for 5 cycles, followed by 30 s at 95° C., 30 s at 58° C., and 45 s at 72° C. for 25 cycles. Control PCR reactions using either primer alone or without genomic DNA in PCR reactions yielded no PCR product. This PCR product was cloned into vector pGEMT-easy (Promega, Madison, Wis.) and three clones were randomly chosen for DNA sequencing. Results from DNA sequencing showed that the inserts in the three pGEMT-easy clones were 530 bp in length. An incomplete ORF was identified within this 530 bp of DNA. The deduced N-terminal protein sequence of this incomplete ORF was MKEQLKPLLEDKTYLRHFWHPV-VTL (SEQ ID NO:36), completely identical to NdmB N-terminal protein sequence. Approximately 500 nucletoides near the 3' end of ndmB were missing.

The nested PCR approach that successfully amplified ndmA flanking regions could not directly amplify the missing 3' end of ndmB. Therefore, a modified procedure was used. First, PCR primers B-iPCR-F2 and B-iPCR-R2 (Table 5) were designed from the 5' half of ndmB. Using these 2 primers plus the EcoRI gDNA library as template, an inverse PCR reaction was run using PfuUltra DNA polymerase with a thermal profile of 30 s at 95° C., 60 s at 55° C., and 8 minutes at 68° C. for 15 cycles. After completion of the PCR, 20 units of DpnI was directly added to the PCR reaction and incubated for 1 hour at 37° C. to destroy all the plasmid DNAs of the gDNA library. The purpose of this DpnI treatment was to enrich DNA fragments that contained ndmB. Then, 1 μL of the DpnI-treated PCR was used as template in a PCR reaction with primers B-speF3 (Table 6) plus pUC19R2 and Taq DNA polymerase, using a thermal profile of 30 s at 94° C., 30 s at 62° C., and 2 minutes at 72° C. for 10 cycles, and 30 s at 94° C., 30 s at 60° C., and 2 minutes at 72° C. for 20 cycles. After this first round of PCR, 0.5 μL of it was used in a second round of PCR using primers B-speF6 (Table 5) plus pUC19R and Taq DNA polymerase, using a thermal profile identical to the first round. A 1.1-kb PCR product was formed as the only PCR product (FIG. 7A, fragment e). This PCR product was gel-purified, subjected to DNA sequencing directly, and confirmed that it contained the missing 3' half of ndmB plus 194 nucleotides downstream to ndmB.

A nested PCR approach was also used to amplify the DNA both 5' and 3' to ndmB. The sequence 5' to ndmB was amplified with specific reverse primer B-speR10 (Table 5) and Marcy using the SmaI gDNA library as template with Taq DNA polymerase and a thermal profile of 30 s at 95° C., 30 s at 58° C., and 3 minutes at 72° C. for 30 cycles in the primary reaction. Following this primary reaction, 0.5 μL primary PCR product was used as a template in a second round of PCR with primers B-speR11 (Table 5) and Marcy and Taq DNA polymerase. A thermal profile of 30 s at 95° C., 30 s at 60° C., and 3 minutes at 72° C. for 30 cycles was used in this secondary reaction, resulting in amplification of a PCR product of 1.9 kb (FIG. 7A, fragment f). Control reactions using either B-speR11 or Marcy alone or without the primary PCR product did not yield this 1.9-kb PCR product. The 1.9-kb PCR product was gel purified and sequenced directly, and was found to contain 150 bp of the 5' end of ndmB, one complete ORF (orf5), and 79% of the 3' end of orf4 (FIG. 7A).

Two specific forward primers, B-speF7 and B-speF8 (Table 5), were designed to amplify the DNA region 3' to ndmB. Primers B-speF7 and Marcy were used in a primary PCR reaction using the SmaI gDNA library as template with Taq DNA polymerase and a thermal profile of 30 s at 95° C., 30 s at 58° C., and 3 minutes at 72° C. for 30 cycles. Subsequently, 0.5 µL of the primary PCR product was used as template in a second round of PCR with primers B-speF8 plus Marcy and Taq DNA polymerase with a thermal profile of 30 s at 95° C., 30 s at 60° C., and 3 minutes at 72° C. for 30 cycles. An approximately 4.3-kb PCR product (FIG. 7A, fragment g) was amplified in this second round of PCR, which was not produced in control reactions using either B-speF8 or Marcy alone or without the primary PCR product as template. Following gel purification, the 4.3-kb PCR product was directly sequenced. The 295 bp of the 3' end of ndmB were contained in the 4.3-kb PCR product. Also, three complete ORFs, orf7, orf8, orf9, and a partial ORF, designated as ndmD.

Degenerate PCR primers were designed from the N-terminal amino acid sequences of NdmA and NdmB and the conserved protein and nucleotide sequences in other ROs (Table 5) to successfully amplify eight PCR products from two CBB5 genomic libraries.

The complete ndmD gene sequence was obtained with an additional nested PCR reaction. Primers ROx-F1 and Marcy were used with the EcoRI gDNA library and Taq DNA polymerase, running with a thermal profile of 30 s at 95° C., 30 s at 58° C., and 3 minutes at 72° C. for 30 cycles. A 0.5 µL aliquot of this primary PCR reaction was used as the template for a second round of PCR with primers ROx-F2 plus Marcy and Taq DNA polymerase. A thermal profile of 30 s at 95° C., 30 s at 60° C., and 3 minutes at 72° C. for 30 cycles was used in this second round of PCR, which resulted in a 2-kb DNA fragment (FIG. 7A, fragment h). This fragment was not produced in control reactions using either ROx-F2 or Marcy alone or without the primary PCR product as template. The 2-kb PCR product was directly sequenced following gel purification, and contained the 3' end of ndmD.

ndmD was cloned into pET28a as an N-terminal $His_6$-tagged fusion gene. Expression $His_6$-NdmD yields cytochrome c reductase activity.

There are three conserved domains in the reductase (Rieske [2Fe-2S], flavin binding site and plant type [2Fe-2S]. hhhh-hhssglvprgshmnkldvnqwfpiat-
tedlpkrhvfhatllgqemaiwrddsgs-
vnawenrcphrglrltlgantgnelrcqy
hgwtyesgtggctfvpahrdappp-
naarvntfpvrekhgfiwttlgqp-
pgepisilddaqlvnavktnlhsvvidadidgvvsylrqnl safldvfgaa-
saedlhlksmlqdrgilvtrsgsiaihfymqrstiskcvvhaqvltp
rpgyelqknysyamnvirraaeavatdlisitdi sdqtieklevvrenmt-
kappthyicevvtrtgetgdinsywlk-
pigyplpafspgmhisittpegsirgyslvngpderesfiigvkkei
qsrggsrsmhedvkvgtqlkvtlprngfplvqtrkhpilvaggigitpilcmaq
ldqqgssyeihyfarafehvpfqdrltalgdrinv hlglgpdetraklpdimeih-
naqdvdvytcgpqpmietvsavalahgi-
aeesirfeffskkndypysdeeyevelkktgqiftvspgstl lqacldndvriea-
sceqgvcgtcitpvvsgdlehhdtylskkeresgkwimpcvsrckskkivldl (SEQ ID NO :85)

The conserved Rieske [2Fe-2S] motif ($CXHX_{16}CX_2H$) and the catalytic triad motif for the non-heme iron [(E/D)$X_2HX_4H$] were identified in deduced protein sequences of both ndmA and ndmB. ndmA and ndmB transcribed divergently from each other, indicating they are not part of the same transcriptional unit. Moreover, unlike most known ROs for which the genes encoding the reductase and the oxygenase are co-transcribed (reference), a reductase gene was not found directly next to either ndmA or ndmB. However, the deduced protein sequence of an ORF, designated as ndmD was located 3.6 kb downstream to ndmB (FIG. 7A). The arrangement of these 3 conserved domains at the NdmD C-terminus is similar to FNRc-type reductases of RoS (Kweon et al., 2008). Some ROs are 3-component systems requiring a reductase and a ferredoxin, for electron transfer to RO components. In these 3-component ROs, the iron-sulfur clusters in the ferredoxins are either the Rieske [2Fe-2S] type or [3Fe-4S] type (Kweon et al., 2008). ndmD could represent a unique gene fusion of a ferredoxin gene and a reductase gene into a single ORF, and encode a functional reductase that specifically coupled to NdmA and/or NdmB.

Figure 8A:
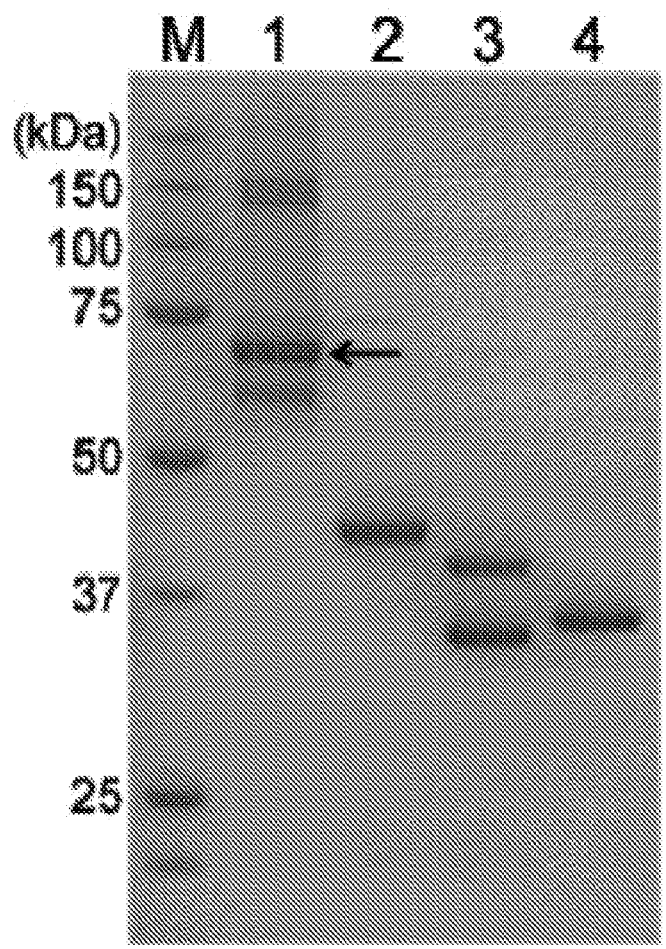
FIG. 8. (A) SDS-PAGE gel of NdmA-His$_6$, NdmB-His$_6$, and His$_6$-NdmD purified from E. coli using Ni-affinity chromatography. Lane M, MW marker; Lane 1, His$_6$-NdmD (indicated by the arrow); lane 2, NdmB-His$_6$; lane 3, natural Ndm purified from P. putida CBB5; lane 4, NdmA-His$_6$. Apparent MW of the NdmB subunit of natural Ndm (lower band of lane 3) was estimated to be 35,000 on SDS-PAGE gel. Theoretical MW deduced from gene sequence was 40,888. Purified NdmA-His$_6$ and NdmB-His$_6$ both contained approximately 2 moles of sulfur and 2 moles of iron per mole of enzyme monomer, as determined by N,N-dimethyl-p-phenylenediamine assay and ICP-MS, respectively. The iron content is lower than the expected value of 3 Fe per α subunit for ROs, which is probably due to dissociation of non-heme Fe from proteins during purification. (B) UV-vis absorption spectrum of NdmA-His$_6$. (C) UV-vis absorption spectrum of NdmA-His$_6$. UV/visible absorption spectra of oxidized NdmA-His$_6$ and NdmB-His$_6$ are similar to other well-characterized ROs, with absorption maxima at 319, 453, and 553 nm and 320, 434, and 550 nm, respectively.
Figure 8B:
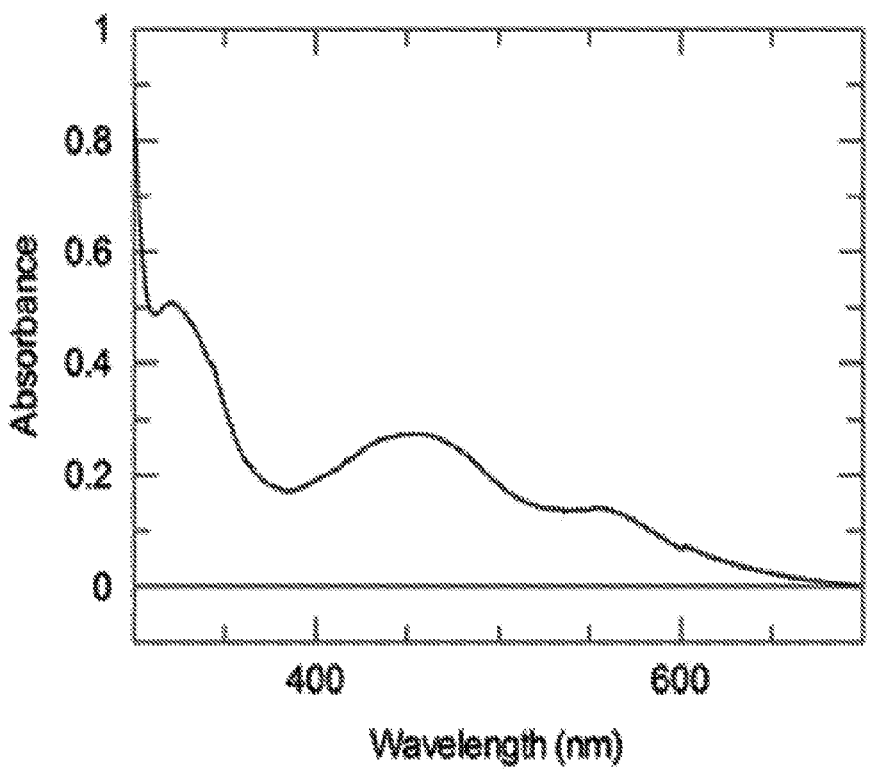
Figure 8C:
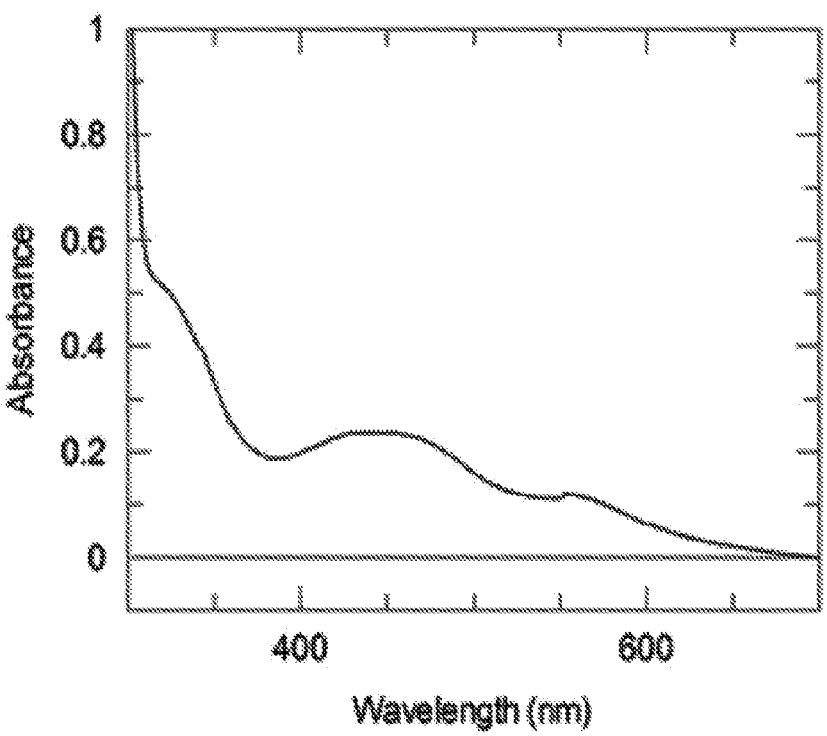
Figure 9A:
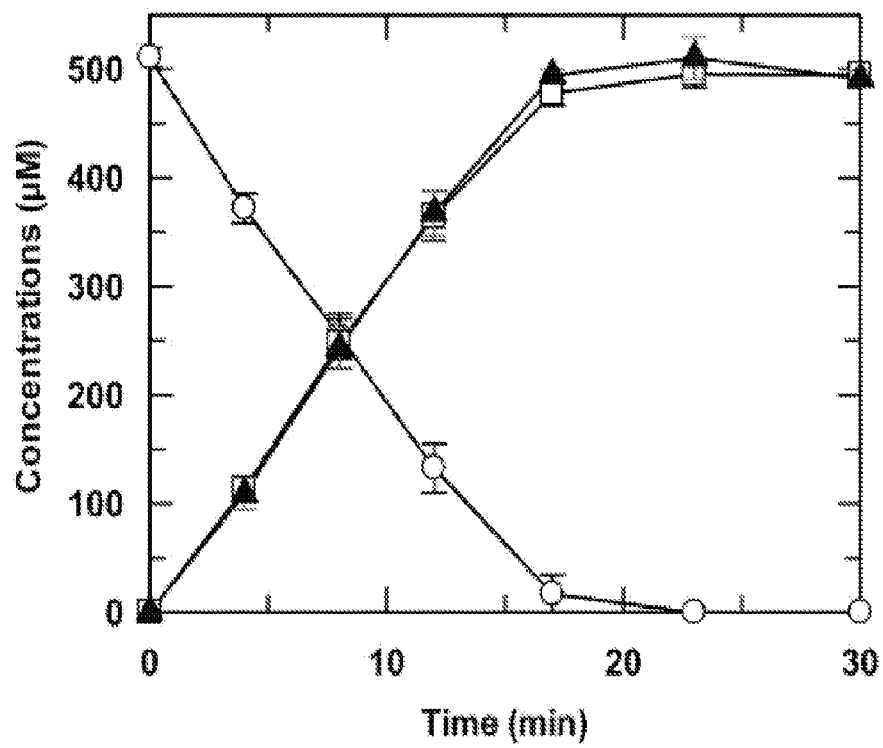
FIG. 9. Stoichiometric N-demethylation of methylxanthine by NdmA-His$_6$ and NdmB-His$_6$. (A) NdmA-His$_6$ N-demethylated caffeine (○) to theobromine (□). One mole of formaldehyde was produced (▲) per mole of theobromine formed. (B) NdmB-His$_6$ N-demethylated theobromine (■) to 7-methylxanthine (◇). Again, one mole of formaldehyde was produced (▲) per mole of 7-methylxanthine formed. Concentrations reported were means of triplicates with standard deviation.
Figure 9B:
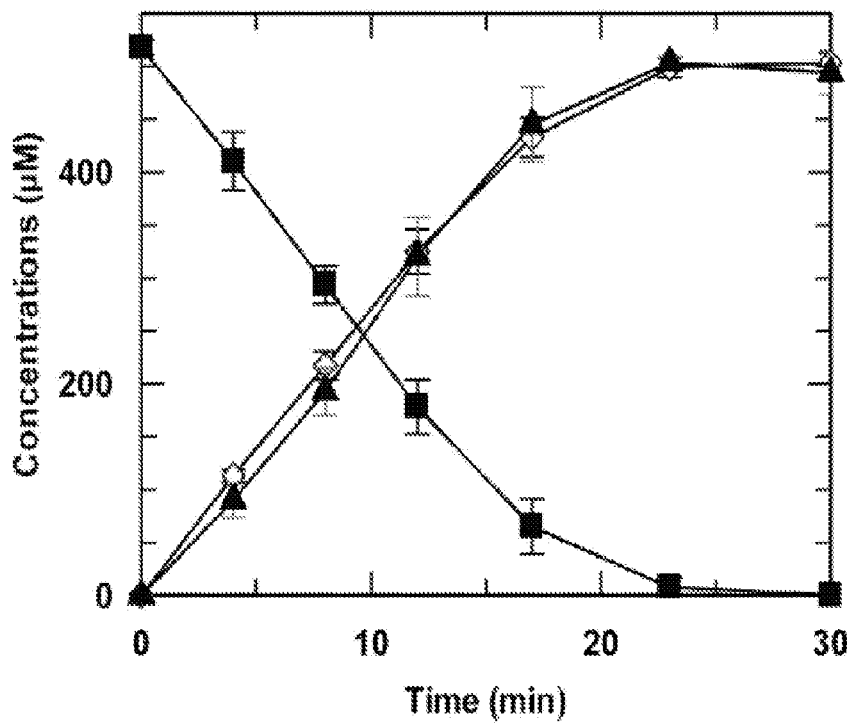

In order to substantiate the hypotheses that ndmA and ndmB individually encoded ROs with methylxanthine N-demethylation activity, and ndmD encoded a specific reductase component for ndmA and/or ndmB, the 3 genes were individually expressed as His-tagged fusion proteins in *E. coli* and were purified using nickel-affinity chromatography (FIG. 8). $His_6$-NdmD oxidized NADH and reduced cytochrome c concomitantly, similar to several RO reductase components (Subramanian et al., 1979; Yu et al., 2007; Haigler et al., 1990). NdmA-$His_6$ and NdmB-$His_6$ could neither oxidize NADH nor reduce cytochrome c. $His_6$-NdmD, NdmA-$His_6$, or NdmB-$His_6$ individually could not N-demethylate caffeine or any related methylxanthines in the presence or absence of NADH and $Fe^{2+}$. However, when NdmA-$His_6$ was incubated with $His_6$-NdmD, caffeine, NADH, and exogenous $Fe^{2+}$, caffeine was stoichiometrically demethylated at $N_1$ to theobromine (3,7-dimethylxanthine) (FIG. 9A). NdmB-$His_6$ with $His_6$-NdmD, theobromine, NADH, and $Fe^{2+}$ resulted in stoichiometric demethylation at $N_3$ of theobromine to 7-methylxanthine (FIG. 9B).

The functions of NdmA and NdmB as position-specific methylxanthine N-demethylases were further supported by the steady-state kinetic parameters of these two enzymes (Table 8).

TABLE 8

Kinetic parameters of NdmA and NdmB

| Enzyme | Substrate | Product | $K_m$ (µM)$^a$ | $k_{cat}$ (min$^{-1}$)$^a$ | $k_{cat}/K_m$ (min$^{-1}$·µM$^{-1}$) |
|---|---|---|---|---|---|
| NdmA-$His_6$ | Caffeine | Theobromine | 37.6± | 192.3± | 5.1 |
| | Theophylline | 3- | 9.1± | 82.9± | 9.1 |
| | Paraxanthine | 7- | 52.9± | 132.9± | 2.5 |
| | Theobromine | — | ∞ | NA$^b$ | NA |

TABLE 8-continued

Kinetic parameters of NdmA and NdmB

| Enzyme | Substrate | Product | $K_m$ (μM)[a] | $k_{cat}$ (min$^{-1}$)[a] | $k_{cat}/K_m$ (min$^{-1}$ · μM$^{-1}$) |
|---|---|---|---|---|---|
| NdmB-His$_6$ | 1- | Xanthine | 266.6± | 15.6± | 0.06 |
| | 3- | — | ∞ | NA | NA |
| | 7- | — | ∞ | NA | NA |
| | Caffeine | Paraxanthine | 41.7± | 0.23± | 0.006 |
| | Theophylline | 1- | 169.0± | 0.27± | 0.016 |
| | paraxanthine | — | ∞ | NA | NA |
| | Theobromine | 7- | 25.3 ± 5.1 | 46.3 ± 1.9 | 1.8 |
| | 1- | — | ∞ | NA | NA |
| | 3- | Xanthine | 22.4 ± 5.2 | 31.7 ± 1.5 | 1.4 |
| | 7- | — | ∞ | NA | NA |

Figure 11:
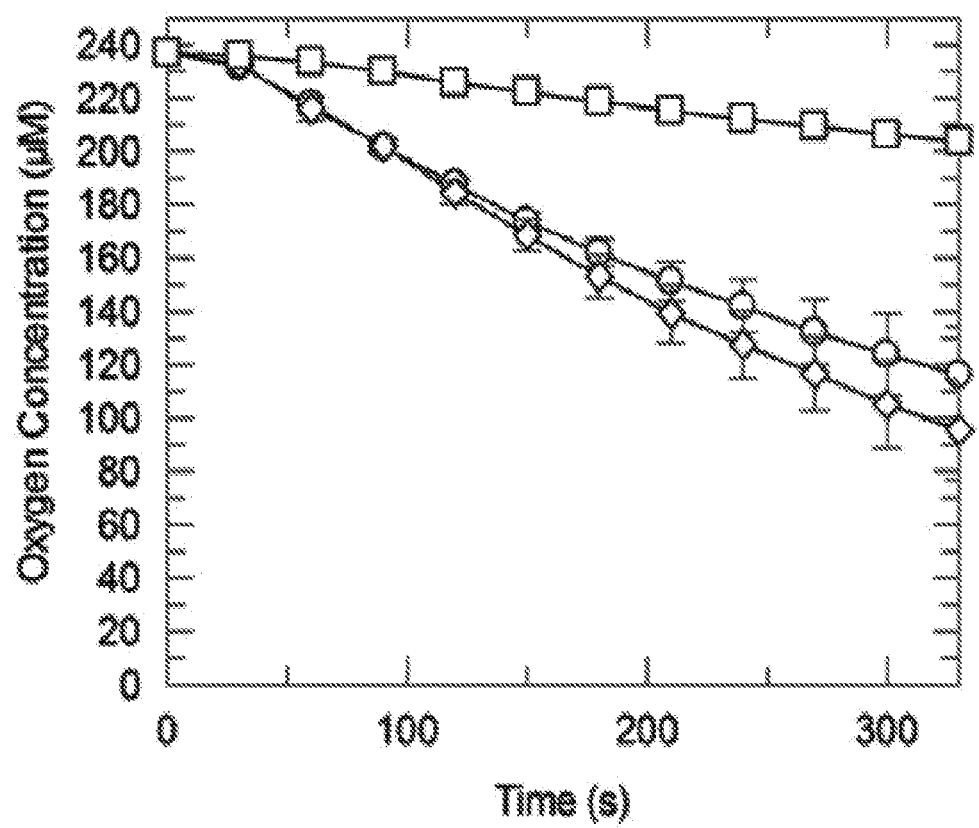
FIG. 11. Stoichiometric consumption of O$_2$ by NdmA-His$_6$ and NdmB-His$_6$ during N-demethylation of caffeine and theobromine, respectively. O$_2$ consumption, determined by using a Clarke-type oxygen electrode, when NdmA-His$_6$ (295 μg) N-demethylated 200 μM caffeine to theobromine (○), or when NdmB-His$_6$ (627 μg) N-demethylated 200 μM theobromine to 7-methylxanthine (◇). Background oxygen consumption in an enzyme reaction with either NdmA-His$_6$ or NdmB-His$_6$ but without methylxanthine is shown (□). Both reactions contained 200 μM NADH, 50 μM Fe(NH$_4$)$_2$ (SO$_4$)$_2$, 4,000 U catalase, and 49 U His$_6$-NdmD. The reactions were carried out in air-saturated buffer and equilibrated at 30° C. for 5 minutes before addition of NdmA-His$_6$ (or NdmB-His$_6$) plus His$_6$-NdmD to initiate the reactions (t=0 sec). Five and a half minutes after initiation of the reactions, 120-µL aliquot was withdrawn from the reaction mixture and immediately quantitated for N-demethylation products by HPLC. Concentrations reported were means of triplicates with standard deviations.

[a]Average and standard deviation were derived from 3 independent assays. Initial reaction rates were determined by following substrate disappearance using HPLC. Initial reaction rates were then plotted against initial substrate concentrations and the data were fit with the Michaelis-Menten equation for determining the kinectic paratmeters.
[b]NA, no activity Theobromine was the preferred substrate for NdmB, with the highest $k_{cat}/K_M$ value of 1.8 min$^{-1}$ μM$^{-1}$, followed closely by 3-methylxanthine. The catalytic efficiencies of NdmB for methylxanthines containing an $N_1$-methyl group were almost $10^2$-$10^3$ times lower than those of theobromine or 3-methylxanthine, while NdmB had no activity on paraxanthine, 1-methylxanthine, or 7-methylxanthine. Clearly, NdmB was highly specific for $N_3$-linked methyl groups of methylxanthines. In contrast, theophylline was the preferred substrate for NdmA, with the highest catalytic efficiency of 9.1 min$^{-1}$ μM$^{-1}$, followed by caffeine, and paraxanthine. The catalytic efficiency of NdmA on 1-methylxanthine was two orders of magnitude lower than that of theophylline. NdmA was inactive on theobromine, 3-methylxanthine, and 7-methylxanthine. Thus, NdmA catalyzed the demthylation only at the $N_1$-position of methylxanthines. Challenging other substrates further substantiated that NdmA and NdmB are $N_1$-specific and $N_3$-specific methylxanthine N-demethylases, respectively. Various methylated purine and pyrimidine analogs were not N-demethylated by NdmA and NdmB, suggesting both enzymes are unlikely to be broad-specificity purine demethylases involved in nucleic acid repair. Both NdmA and NdmB are monooxygenases specific for degradation of methylxanthines. One oxygen is consumed per formaldehyde produced from each N-methyl group removed (FIGS. 9 and 11).

When purified Ndm (containing both NdmA and NdmB) was coupled with a partially purified reductase fraction from CBB5, caffeine was completely N-demethylated to xanthine (Summers et al., 2011; Example 2). This indicated that there is a $N_7$-specific N-demethylase activity in CBB5. This activity was neither associated with NdmA nor with NdmB. This $N_7$-specific N-demethylase activity, designated as NdmC, co-purified with reductase. This fraction specifically N-demethylated 7-methylxanthine to xanthine at the same rates observed in reactions containing active NdmA-His$_6$ or NdmB-His$_6$. Caffeine, paraxanthine, and theobromine were not N-demethylated by this fraction, indicating 7-methylxanthine was the sole substrate for NdmC. Cloning of NdmC has proven difficult; nevertheless based on the fact that purified His$_6$-NdmD had no activity on 7-methylxanthine, we annotate orf8 as aanother RO with highly specific N-7 demthylase activity.

Figure 12:
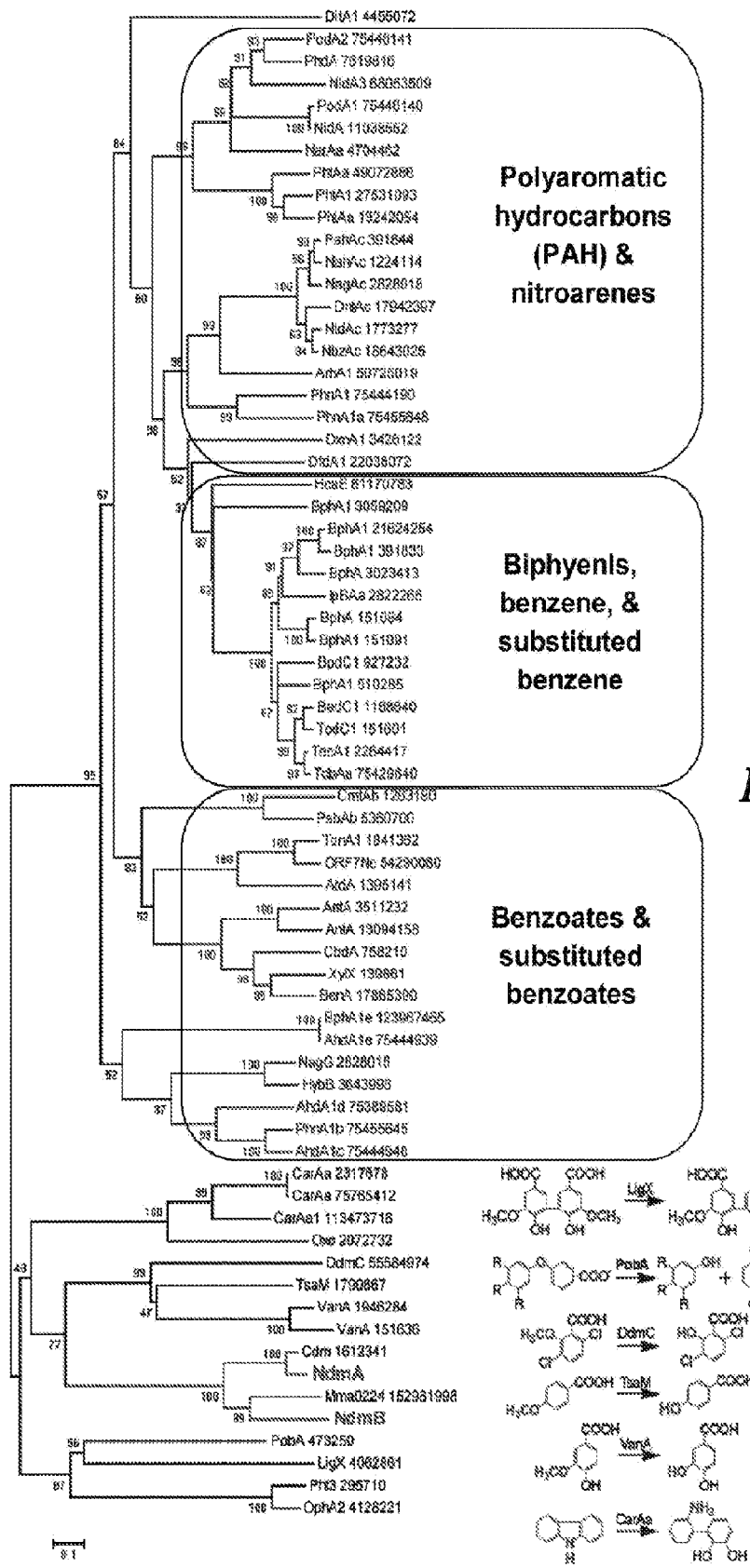
FIG. 12. Phylogenetic analysis of NdmA and NdmB with 64 Rieske [2Fe-2S] domain-containing oxygenases (ROs). Name of the proteins and their GI numbers are displayed in this unrooted phylogenetic tree. ClustalX2.1 (Larkin et al., 2007) was used to align all protein sequences. The multiple sequence alignment was then imported into MEGA software (version 4.0.2; Tamura et al., 2007) and a phylogenetic tree was constructed by Neighbor-Joining method. The bootstrap consensus tree inferred from 5,000 replicates is taken to represent the evolutionary history of the sequences analyzed. Branches corresponding to partitions reproduced in less than 50% bootstrap replicates are collapsed. The percentages of replicate trees in which the associated sequences clustered together in the bootstrap test are shown at the nodes. The tree is drawn to scale, with branch lengths in the same units as those of the evolutionary distances used to infer the phylogenetic tree. The evolutionary distances were computed using the Poisson correction method and are in the units of the number of amino acid substitutions per site. All positions containing gaps and missing data were eliminated from the dataset (Complete deletion option). There were a total of 207 positions in the final dataset. Clustering of ROs into families according to the ROs' respective native substrate is clearly displayed and generally agrees with the results of a similar analysis by Parales and Gibson (2000)). NdmA and NdmB clearly cluster together with ROs such as VanA, CarAa, PobA, DdmC, TsaM, plus LigX. These ROs are known to catalyze O-demethylation or reactions that result in the cleavage of C—N, but not N-demethylation catalyzed by NdmA and NdmB.

A phylogenetic tree comparing the catalytic α subunit of 64 well-characterized ROs placed NdmA and NdmB into a distinctive clade (FIG. 12). In this clade, the closest relatives to NdmA and NdmB are a hypothetical caffeine demethylase (Cdm) reported in U.S. Pat. No. 5,550,041 (Koide et al., 1996) and a hypothetical protein in *Janthinobacterium* sp. Marseille genome (mma_0224). Cdm, 89% identical to NdmA, is likely to be a caffeine N-demethylase. The function of mma_0224 is not clear since it is only approximately 50% identical to NdmA or NdmB. The nearest-neighbor clades to NdmA and NdmB contain ROs that catalyze O-demethylation, C—N bond, or C—O bond-cleaving reactions. The homology between these enzymes and either NdmA or NdmB is solely limited to the N-terminal regions of these proteins where the Rieske [2Fe-2S] domain is located. The low homology among ROs is not surprising considering the diversity of highly hydrophobic specific substrates used by these enzymes. The specific substrate binding locus is predominantly at the C-terminal portion of RO α subunits (Ferraro et al., 2005). Furthermore, phylogenetic analysis did not support monophylogeny between NdmA/NdmB with the majority of ROs that catalyze hydroxylation of aromatic ring substrates. It is likely that divergent evolution of ROs resulted in two groups, one for catalyzing aromatic ring hydroxylations and one for C—O/C—N bond-cleaving reactions.

| SeqA | Name | Len(aa) | SeqB | Name | Len(aa) | Score |
|---|---|---|---|---|---|---|
| 1 | NdmA | 351 | 2 | NdmB | 355 | 49 |
| 1 | NdmA | 351 | 3 | Cdm | 355 | 89 |
| 1 | NdmA | 351 | 4 | mma_0224 | 365 | 53 |
| 2 | NdmB | 355 | 3 | Cdm | 351 | 48 |
| 2 | NdmB | 355 | 4 | mma_0224 | 365 | 58 |
| 3 | Cdm | 351 | 4 | mma_0224 | 365 | 53 |

At least one of the genes in the gene cluster may have a methylxanthine-responsive promoter because the enzymes involved in methylxanthine degradation are induced in the presence of caffeine, the metabolites formed from caffeine, or theophylline (Yu et al. 2009). Moreover, gntR and/or araC may play arole in regulating these promoters (eee FIG. 7C).

Figure 10:
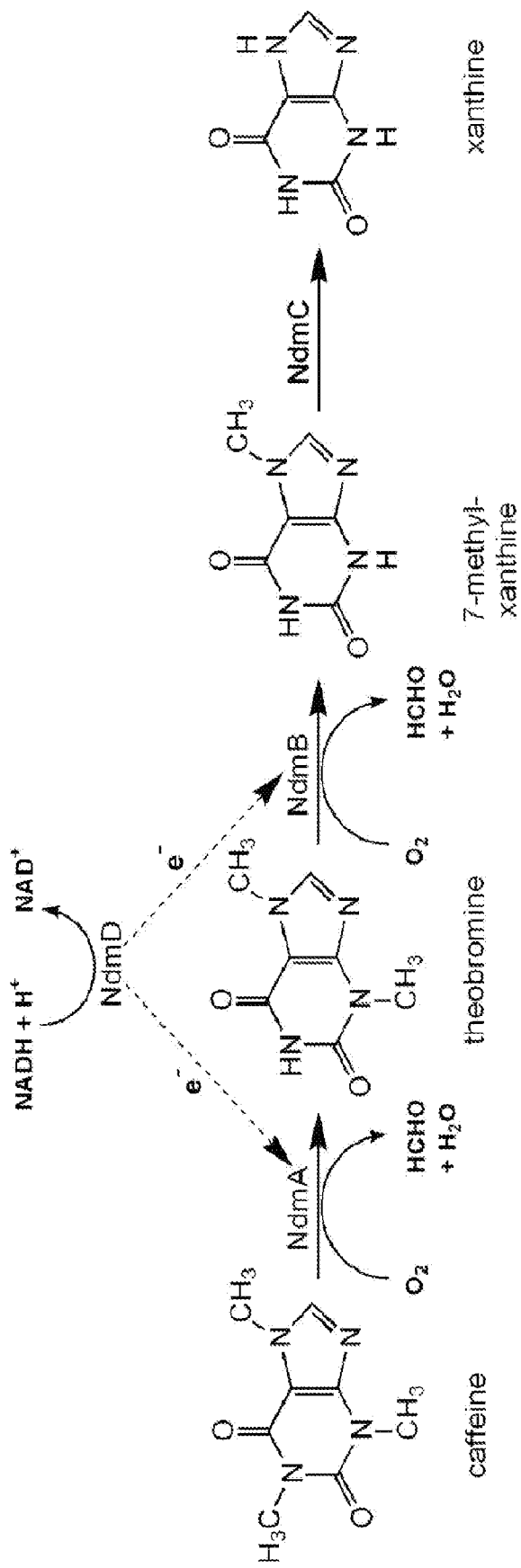
FIG. 10. Sequential N-demethylation of caffeine by Pseudomonas putida CBB5. N-demethylation of caffeine is initated at the N$_1$-position by NdmA, forming theobromine. Then, NdmB catalyzes removal of the N-linked methyl group at the N$_3$ position, producing 7-methylxanthine. Oxygen is the co-substrate for NdmA and NdmB. NdmD couples with NdmA and NdmB by transferring electrons from NADH to NdmA and NdmB for oxygen activation. Each methyl group removed results in the formation of one formaldehyde. NdmC (orf 8 in FIG. 7) is proposed to be specific for N-demethylation of 7-methylxanthine to xanthine.

In conclusion, the utilization of caffeine by CBB5 likely occurs via N-demethylation in a preferential sequence (FIG. 10). The $N_1$-methyl group is first removed from caffeine by NdmA, forming theobromine, which is the preferred substrate of NdmB. NdmB then removes the $N_3$-methyl group, producing 7-methylxanthine. Based on activity in partially purified fraction as well as gene-annotation, NdmC is proposed to catalyze $N_7$-demethylation. This ordered N-demethylation of caffeine is supported by the catalytic efficiencies of NdmA and NdmB on various methylxanthines. Both NdmA and NdmB are monooxygenases; one oxygen is consumed per N-methyl group removed as formaldehyde. NdmD appears to be the sole reductase for transfer electrons from NADH to NdmA, NdmB and possibly NdmC for oxygen activation and N-demethylation to formaldehyde.

The discovery of highly specific methylxanthine N-demethylases has shed light on the long-standing question of how bacteria are able to use caffeine and other methylxanthines as sole source of carbon and nitrogen. CBB5 is able to use xanthine, formaldehyde and formate, which are liberated from caffeine and other methylxanthines. NdmA B and C could have broad applications in bioremediation of environments contaminated by caffeine and related methylxanthines, particularly in countries with large coffee- and tea-processing industries. These genes could also find utility in detecting caffeine, a marker for human activities in wastewater streams (Buerge et al., 2006). These genes could also be used in converting the enormous waste generated via manufacturing of coffee and tea to animal feed and feedstocks for fuels and fine chemicals (Mussatto et al., 2011). Last, but not least, these genes could prove useful in production of pharmaceutically-useful modified xanthine analogs, which are currently being synthesized by challenging multi-step processes. Finally, the assignment of NdmA and NdmB to the RO enzyme family broadens our understanding on the enzymatic mechanism for N-demethylation reactions, as we generally have less knowledge regarding demethylases than methylating enzymes (Hagel et al., 2010). This first report of a RO, soluble bacterial N-demethylase will certainly stimulate the discovery of new N-demethylases involved in the degradation of many natural products and xenobiotics.

EXAMPLE 4

Figure 13:
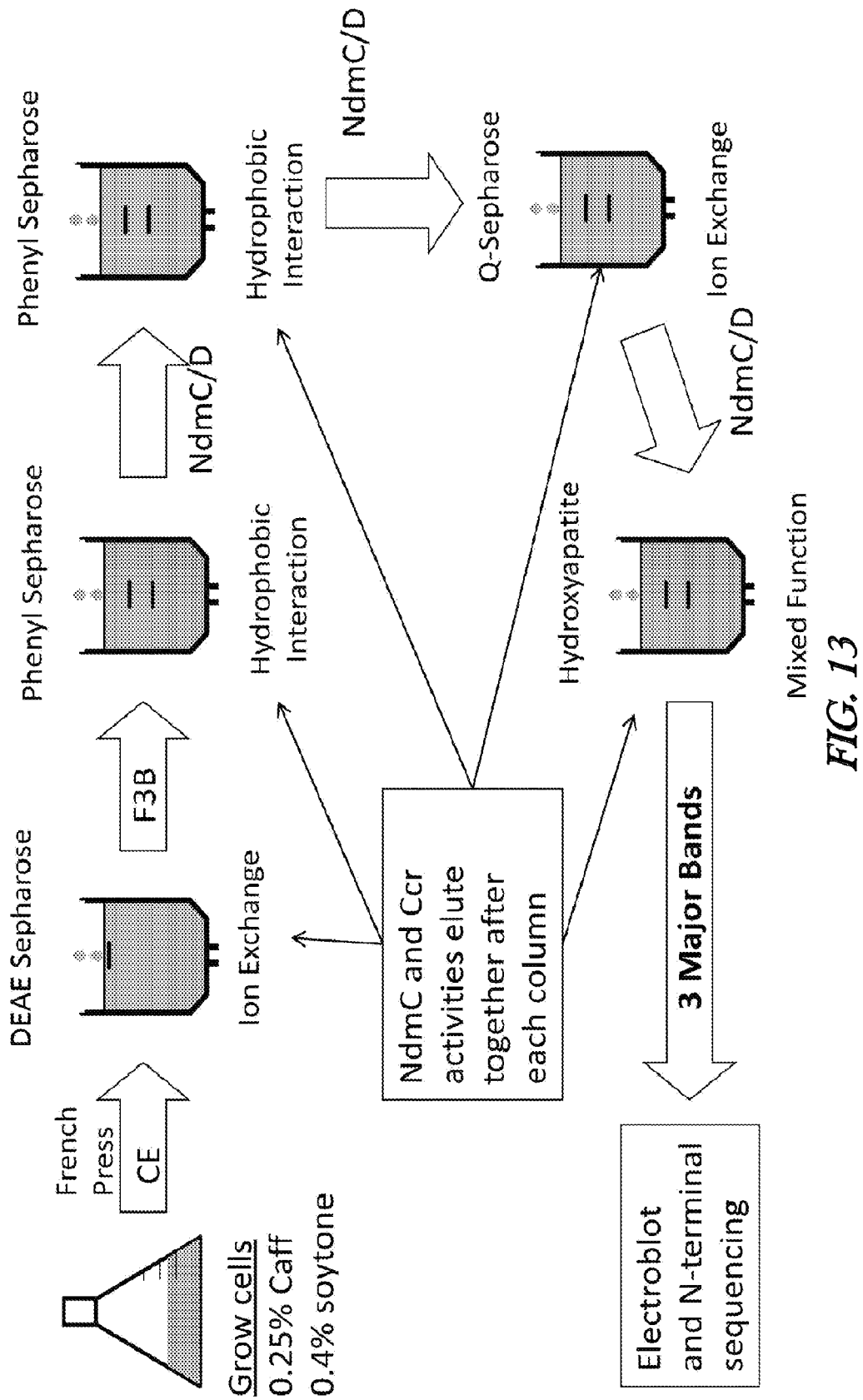
FIG. 13. A schematic of a protocol for the partial purification of NdmC/D.
Figure 14A:
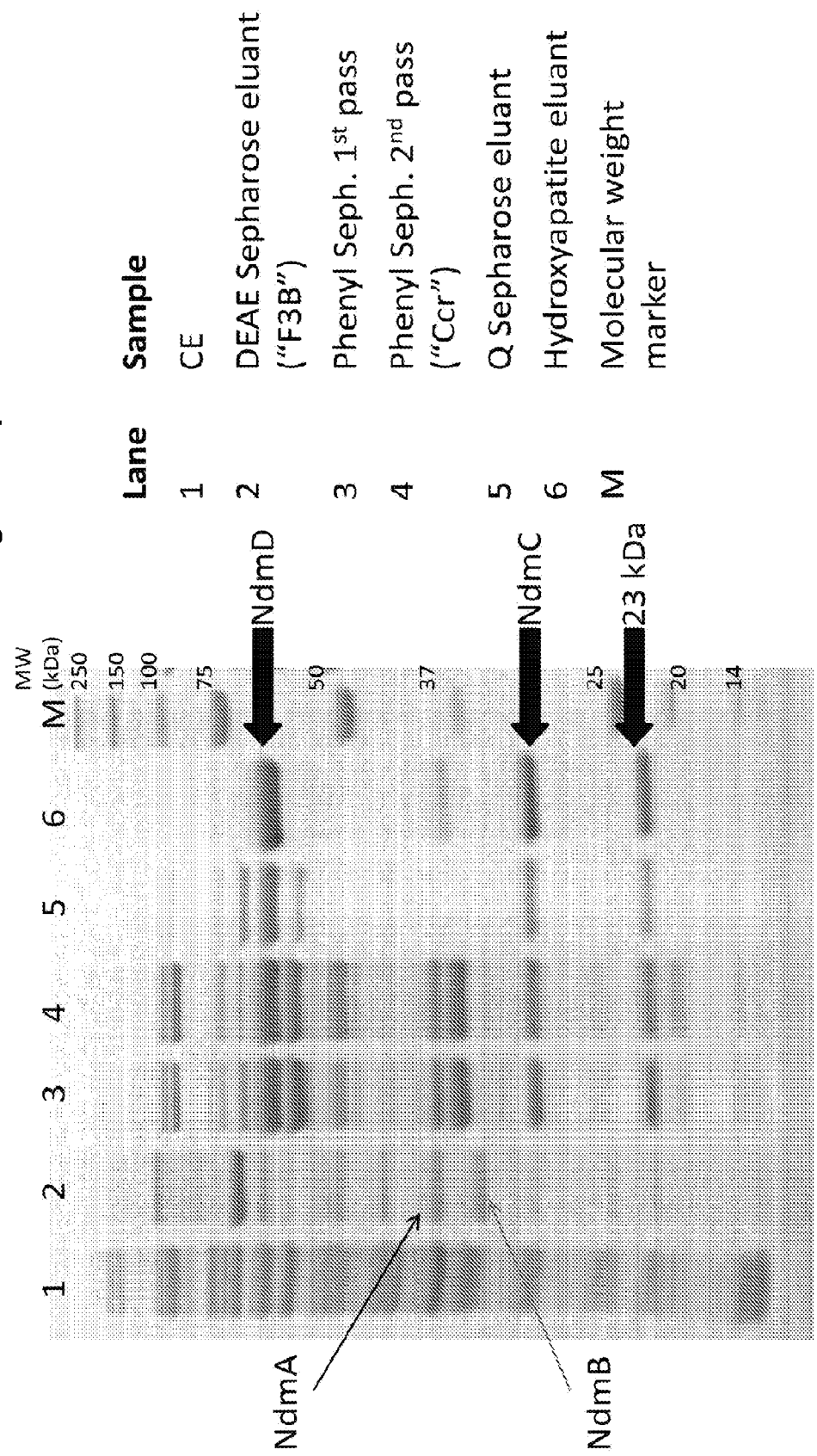
FIG. 14. (A) SDS-PAGE analysis of NdmC and NdmD proteins after multi-column purification. (B) SDS-PAGE analysis of His-Ccr after multi-column purification.

FIG. 13 shows the partial purification of NdmC/D. After passing through 5 chromatographic steps, including DEAE, phenyl, and Q sepharose and hydroxyapatite columns, the three major bands of 67 (NdmD), 32 (NdmC), and 23 kDa downstream of NdmD were not resolved. The fraction still had NdmD and NdmC activity. FIG. 14 shows a SDS gel with the fraction for NdmD, the N-terminal sequence MNKLDVNQ?FPIATTEDLPKRHVFHATLLG (SEQ ID NO:40) matched ORF 9 (3 ORFs downstream of ndmB), and for the N-terminal sequence NdmC, STDQVIFND?HPVAALEDVSLDKR?R?RLL (SEQ ID NO:41) matched ORF 8 (2 ORFs downstream of ndmB). A 23 kDa protein had the following N-terminal sequence MITL?D?ELSGN??KIRLFLSILNMG?QTE (SEQ ID NO:42), which matched ORF 10 (4 ORFs downstream of ndmB). To solubilize NdmC, cells are stressed by adding ethanol to improve solubility.

EXAMPLE 5

To produce alkylxanthines, NdmA is introduced to host cells, e.g., *Pichia* cells which may be spray-dried. Sources of caffeine or theophylline are mixed with spray-dried cells and the redox reactions yield products such as theobromine 3-methylxanthine. NdmB is introduced to host cells, e.g., *Pichia* cells which may be spray-dried. Sources of caffeine, theobromine or theophylline are mixed with the cells and the redox reactions yield products 1,7-dimethylxanthine, 7-methylxanthine, 1-methylxanthine.

NdmA and NdmB are introduced to *Pichia* cells which are spray-dried, and caffeine or theobromine is added. Redox reactions with those cells, e.g., spray-dried cells, yield products 7-methylxanthine.

NdmC is introduced to host cells such as *Pichia* cells, which may be spray-dried, and caffeine or theobromine is added to these cells. Redox reactions in the presence of the cells provide products 1,3-dimethylxanthine and/or 3-methylxanthine.

NdmA, B and C are introduced to host cells such as *Pichia* cells which may be spray-dried, and a source of caffeine, theobromine or theophylline is added to those cells. Redox reactions result in products including a variety of di- and mono-methylxanthines.

EXAMPLE 6

Figure 7C:
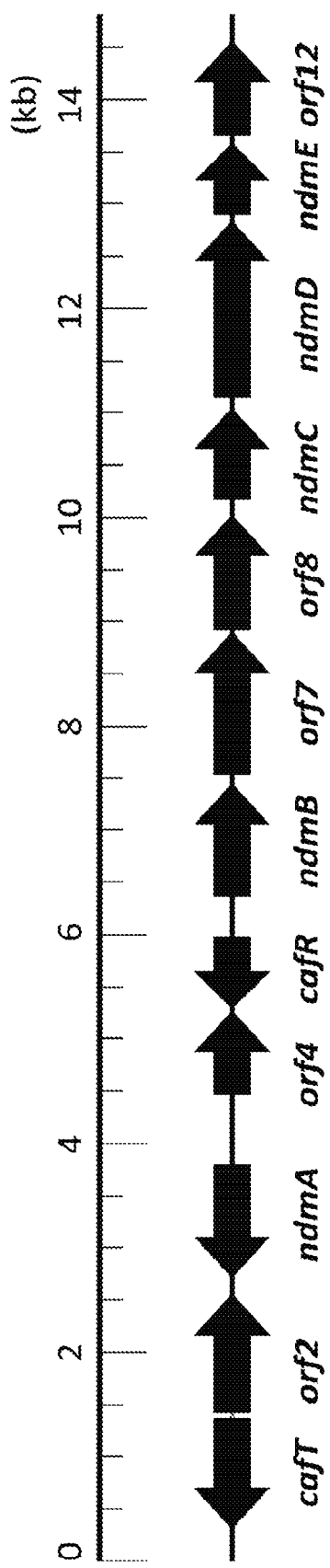
Figure 7F:
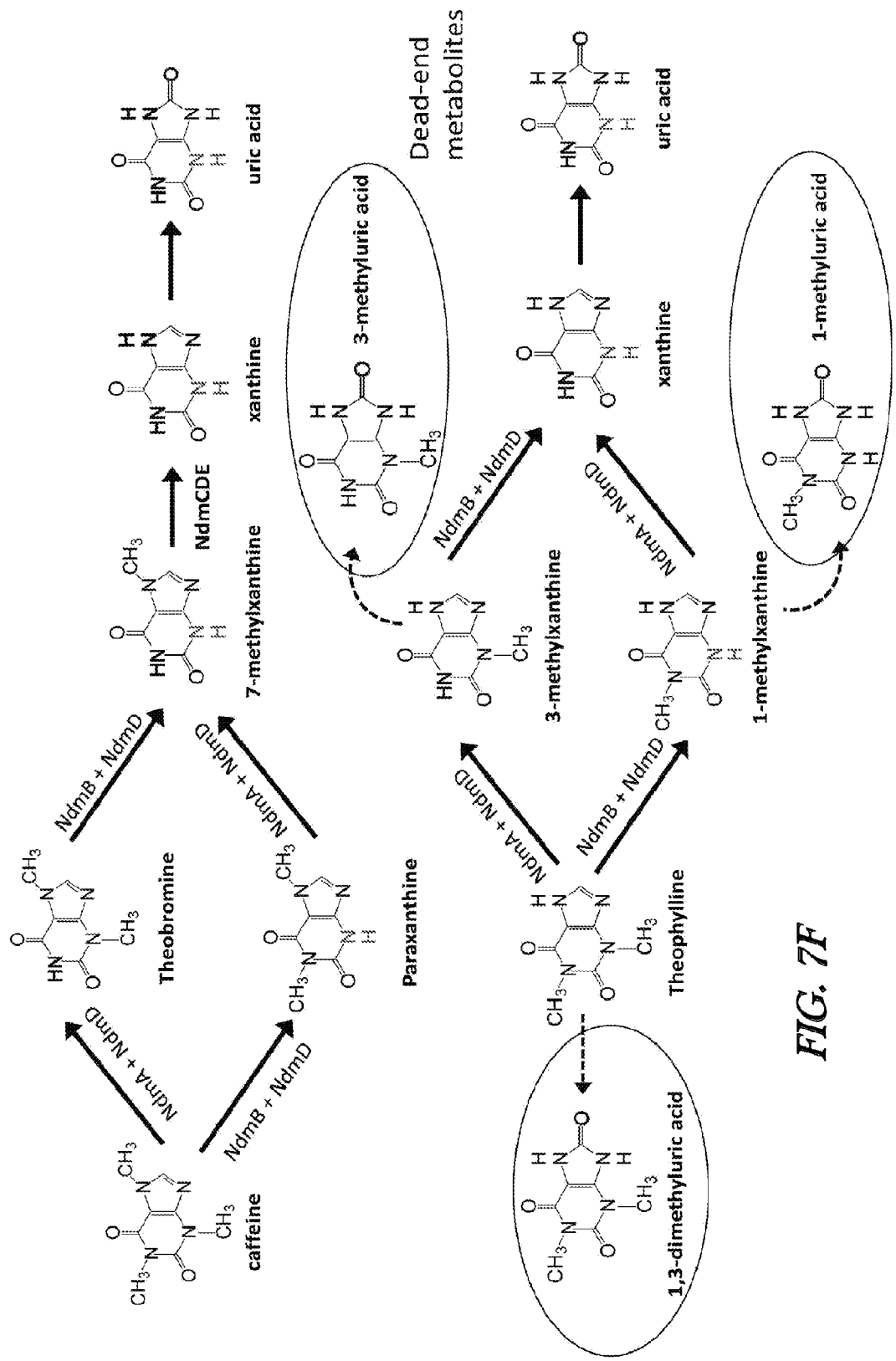
Figure 7G:
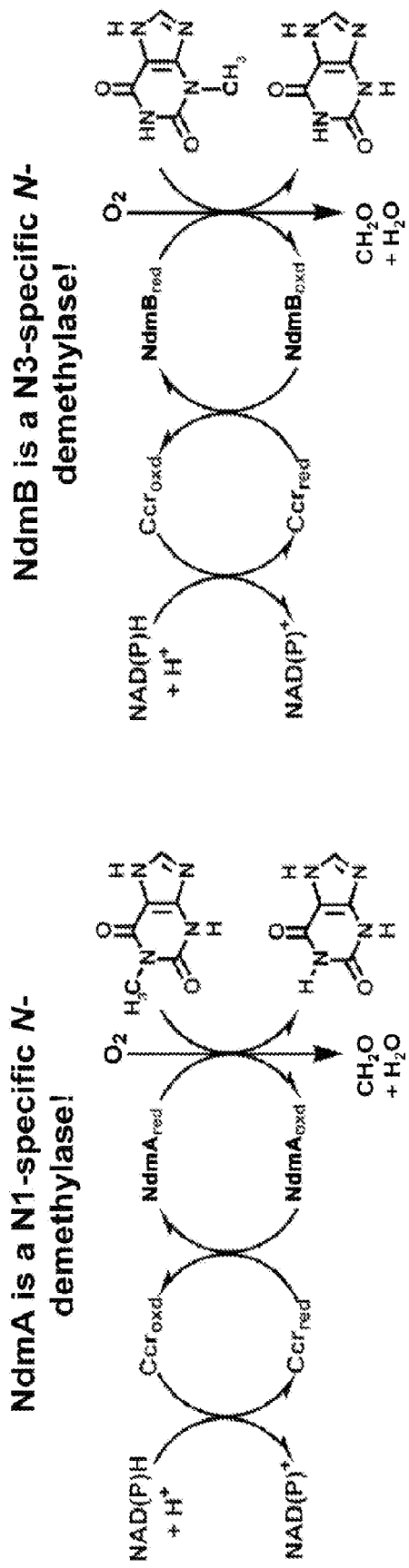

A gene denoted as encoding a glutathione S transferase (GST) in FIG. 7C was cloned and is referred to as NdmE. The nucleotide sequence for NdmE and the sequence of the encoded protein are provided below:

```
NdmE DNA sequence
                                                      (SEQ ID NO: 44)
GTGATTACACTCTATGACTATGAGCTTTCCGGGAACTGCTACAAGATCAGGCTTTTTTGTCCATTC

TGAATATGGGATACCAAACTGAGCCTGTAGAGTTCTATCCGTCGCGTGAGCATAAATCTGAAGCGTT

CCTGAAAATCAATCCTCTCGGCCAACTTCCTGCTTTGAAGGATGGTGATCTCGTGCTGAGGGACGCA

CAGGCAATTCTCGTCTATCTGGCCACTCAGTATGATAAGAGCTGCTACTGGTACCCGACCGCCCGCC

CGGATCTGATGGCTGAGGTCAACATGTGGATGGCCTTTGCTGATAGCCTGACCAGCACCATTTCTTC

CGCGCGATTACATGACTTGTTTTCTATGAATTCGATGTAAATGCATGCCGCCTGCGTGCCCGAGA

TTTGTTGAGGATATTGGATGAACATCTTTGGTTCAGGGATCTAAAGGGTCTTCAATATATTTGT

AGTTCGCTGCATCCTACGATCGCAGACATCGCCTGTTTCCCATACATCGCTTTGTCAGATGAGG

CGGGCGTATCCCTAGAAGACTTCCCTGCCGTACGTCGGTGGGTTGATAGGGTAAAACGCCTACC
```

-continued

```
AGGCTTTGTTGTAATGTCGGGAGTATTCCCCACGTCACCTATGTATGAAGGTTCCGCGCGACGG

GTGAGTGCATAG

NdmE Peptide Sequence
                                                                  (SEQ ID NO: 45)
VITLYDYELSGNCYKIRLFLSILNMGYQTEPVEFYPSREHKSEAFLKINPLGQLPALKDGDLVLRDA

QAILVYLATQYDKSCYWYPTARPDLMAEVNMWMAFADSLTSTISSARLHDLFFYEFDVNACRLRARD

LLRILDEHLWFRDLKGLQYICSSLHPTIADIACFPYIALSDEAGVSLEDFPAVRRWVDRVKRLPGFV

VMSGVFPTSPMYEGSARRVSA
```

It was found that in the absence of expression of NdmE, recombinant *E. coli* cells that contain NdmABCD synthesized 7-methylxanthine from caffeine, but not xanthine. Also, when 7-methylxanthine was provided as a substrate to cells containing only NdmABCD, xanthine was not produced and the 7-methylxanthine remained untouched. Conversely, *E. coli* cells expressing NdmABCDE converted both caffeine and 7-methylxanthine to xanthine.

The NdmE protein is related to proteins of *Janthinobacterium* and *Mesorhizobium* (see the alignments below; the NdmE protein from CBB5 is depicted on the top line, the middle line show residues that are identical, are conservative (+) or not conservative (open space) between proteins from CBB5 and *Janthinobacterium* or *Mesorhizobium*, and the lower line is a homolog of NdmE from *Janthinobacterium* (upper alignment) or *Mesorhizobium* (lower alignment)).

```
                VITLYDYELSGNCYKIRLFLSILNMGYQTEPVEFYPSREHKSEAFLKINPLGQLPALKDG (SEQ ID NO: 46)
                +ITLYDYELSGNCYK+R +LSIL + Y  E VEF+PSREHKS AFL+INPLGQLP L+D  (SEQ ID NO: 47)
                MITLYDYELSGNCYKVRMLLSILKLPYTIETVEFFPSREHKSPAFLRINPLGQLPVLRDD (SEQ ID NO: 48)

DLVLRDAQAILVYLATQYDKSCYWYPTARPDLMAEVNMWMAFADSLTSTISSARLHDLFF
                D VLRDAQAILVYLA +YD S  WYPT  P ++ +  NMW+AFAD LT +IS+ARLHDLFF
                DFVLRDAQAILVYLANKYDTSLTWYPTHAPAILGQANMWLAFADGLTGSISAARLHDLFF

YEFDVNACRLRARDLLRILDEHLWFRDLKGLQYICSSLHPTIADIACFPYIALSDEAGVS
                Y+F+   CR RA +LLRILDEHLW  +  G Q++C +  PTIAD+ACFPYIALSDEAGVS
                YDFNAEQCRARAHELLRILDEHLWAAEQNGHQWLCPAAAPTIADLACFPYIALSDEAGVS

LEDFPAVRRWVDRVKRLPGFVVMSGVFPTSPMYEGSA
                L D+PAVRRW+DRVKR+PGF VMSG+FPTS  +E ++
                LLDYPAVRRWLDRVKRIPGFTVMSGIFPTSASFEPAS

VITLYDYELSGNCYKIRLFLSILNMGYQTEPVEFYPSREHKSEAFLKINPLGQLPALKDG (SEQ ID NO: 58)
                +ITLYDYELSGNCYK+RL +S L +GY+T PV+FYP REHKSE FLK+NPLGQLP L+D  (SEQ ID NO: 59)
                MITLYDYELSGNCYKLRLMMSFLGIGYKTVPVDFYPGREHKSEWFLKLNPLGQLPVLEDD (SEQ ID NO: 60)

DLVLRDAQAILVYLATQYDKSCYWYPTARPDLMAEVNMWMAFADSLTSTISSARLHDLFF
                L+LRDAQAILVYLA++YD S  WYP   P L+ E++   W+AFAD +T T S+ARLHD F
                GLLLRDAQAILVYLASKYDPSNRWYPRDNPALLGEISQWLAFADGITGTASAARLHDGLF

YEFDVNACRLRARDLLRILDEHLWFRDLKGLQYICSSLHPTIADIACFPYIALSDEAGVS
                YE D++A R+ A   L RILDEHLWF + +G  +ICS+ HPTIAD+ACFPY+ LS+E G+
                YELDIDAARVGAHRLFRILDEHLWFGEQEGRDWICSANHPTIADVACFPYVILSEEGGIP

LEDFPAVRRWVDRVKRLPGFVVMSGVFPTSP
                +D+PA+RRW DRVKR+ GF+VMSGVFP   P
                RQDYPAIRRWCDRVKRIKGFIVMSGVFPAGP
```

Reference

Aas et al., *Nature*, 421:859 (2003).
Abel et al., *Enz. Microb. Technol.*, 33:743 (2003).
Altschul et al., *Nucleic Acids Res.*, 25:3389 (1997).
Ames et al., *Proc. Natl. Acad. Sci. USA*, 78:6858 (1981).
Arnaud, *Methylxanthines*, 200:33 (2011).
Asano et al., *Biosci. Biotechnol. Biochem.*, 57:1286 (1993).
Asano et al., *Biosci. Biotechnol. Biochem.*, 58:2303 (1994).
Asha et al., *Biotechnol. Adv.*, 27:16 (2009).
Blecher et al., *Physiol. Chem. Bd*, 358:807 (1977).
Blecher, *Zentrabl Bakeriol.[orig b]*, 162:180 (1976).
Bradford, *Anal. Biochem.*, 72:248 (1976).
Brand et al., *Enzyme and Microbial Technology*, 27:127 (2000).
Brunel et al., *J. Bacteriol.*, 170:4924 (1988).
Bruns et al., *Proc. Natl. Acad. Sci. USA*, 77:5547 (1980).
Bryksin et al., *Biotechniques*, 48:463 (2010).
Buerge et al., *Environ. Sci. Technol.*, 37:691 (2003).
Buerge et al., *Environ. Sci. Technol.*, 40:4096 (2006).
Capyk et al., *J. Bioi. Chem.*, 284:9937 (2009).
Caubet et al., *J. Pharma. Biomed. Anal.*, 34:379 (2004).
Cha et al., *Appl. Environ. Microbiol.*, 67:4358 (2001).
Chang et al., *Science*, 318:444 (2007).
Daly, *Cell Mol. Life. Sci.*, 64:2153 (2007).
Daly, *J. Autonomic Nervous System*, 81:44 (2000).
Dash et al., *Biotechnol. Lett.*, 28:1993 (2006).
Dash et al., *J. Basic Microbiol.*, 48:227 (2008).
Dikstein et al., *J. Biol. Chem.*, 224:67 (1957).
Dong et al., *J. Bacterial.*, 187:2483 (2005).
Ensley et al., *J. Bacteriol.*, ISS:505 (1983).
Evgeny et al., *Carcinogenesis*, 29:1228 (2008).
Fee et al., *J. Biol. Chem.*, 259:124 (1984).
Ferraro et al., *Biochem. Biophys. Res. Commun.*, 338:175 (2005).
Fetzner, *Naturwissenschaften*, 87:59 (2000).
Floyd, *FASEB J.* 4:2587 (1990).
Friemann et al., *J. Mol. Biol.*, 348:1139 (2005).
Gerken et al., *Science*, 318:1469 (2007).
Glock et al., *Appl. Microbiol. Biotechnol.*, 28:59 (1988).
Guengerich, *Chem. Res. Toxicol.*, 14:611 (2001).
Nagel et al., *Front Physiol.*, 1:14 (2010).
Haigler et al., *J. Bacteriol.*, 172:465 (1990).
Haigler et al., *J. Bacteriol.*, 1n:457 (1990b).
Haigler et al., *J. Bacteriol.*, 1n:465 (1990a).
Hakil et al., *Enz. Microb Technol.*, 22:355 (1998).
Heckman et al., *J. Food Science*, 75:77 (2010).
Herman et al., *J. Biol. Chem.*, 280:24759 (2005).
Hille, *Arch. Biochem. Biophys.*, 433:107 (2005).
Hollenberg, *Faseb. J.*, 6:686 (1992).
Ina, *Nippon Nodeikadaku kaishi*, 45:378 (1971).
Jones et al., *Anal. Chem.*, 71:4030 (1999).
Kauppi et al., *Structure*, 6:571 (1998).
King and Sternberg, *Protein Sci.*, 5:2298 (1996).
Koide et al., U.S. Pat. No. 5,550,041 (1996).
Koide et al., United States; 1996.
Kurtzman et al., *Experiencia*, 127:481 (1971).
Kvalnes-Krick et al., *Biochemistry*, 25:6061 (1986).
Kweon et al., *BMC Biochem.*, 9:11 (2008).
Ladenson et al., *Anal. Chem.*, 78:4501 (2006).
Larkin et al., *Bioinformatics*, 23:2947 (2007).
Lee, Biochemical studies on toluene and naphthalene dioxygenases. Ph.D. Thesis. The University of Iowa, Iowa City, Iowa (1995).
Lee, *Clin. Chim. Acta*, 295:141 (2000).
Leimkuhler et al., *J. Biol. Chem.*, 278:20802 (2003).
Madyashta et al., *Biochem. Biophys. Res. Commun.*, 263:460 (1999).
Madyastha et al., *Biochem. Biophys. Res. Commun.*, 249:178 (1998).
Mandell, *J. Cardiovascular Pharma.*, 25:20 (1995).
Martins et al., *Structure*, 13:817 (2005).
Mazzafer et al., *Microb. Ecol.*, 31:199 (1996).
Mazzafera, *Frontiers in Bioscience*, 9:1348 (2004).
Mazzafera, *Scientia Agricola*, 59:815 (2002).
McGuffin et al., *Bioinformatics*, 16:404 (2000).
Meskys et al., *Eur. J. Biochem.*, 268:3390 (2001).
Middelhoven et al., *European J. Appl. Microbiol. Biotechnol.*, 15:214 (1982).
Mohapatra et al., *J. Biotechnol.*, 125:319 (2006).
Mussatto et al., *Food Bioprocess Tech.*, 4:661 (2011).
Nishida, 43:885 (1991).
Nishiya et al., *J. Ferment. Bioenq.*, 75:239 (1993).
Ogunseitan, *World J. Microbial. Biotechnol.*, 12:251 (1996).
Ogunseitan, *World J. Microbial. Biotechnol.*, 18:423 (2002).
Parales and Gibson, *Cur. Opin. Biotechnol.*, 11:236 (2000).
Philips et al., *Appl. Environ. Microbial.*, 64:3954 (1998).
Pollastri et al., *Bioinformatics*, 21:1719 (2005).
Ramanaviciene et al., *Acta Medica Lituanica*, 10:185 (2003).
Rosche et al., *J. Biol. Chem.*, 270:17836 (1995).
Sambrook et al., *Molecular Cloning: A Laboratory Manual*, 2nd ed. Cold Spring Harbor, N.Y: Cold Spring Harbor Laboratory (1989).
Sauer et al., *Develop. Biochem.*, 23:452 (1982).
Schrader et al., *Eur. J. Biochem.*, 264:862 (1999).
Schultz et al., *J. Bacteriol.*, 188:3293 (2001).
Schwimmer et al., *Arch. Biochem. Biophys.*, 147:109 (1971).
Seiler et al., (1999). *Ground Water,* 37:405 (1989).
Shamim et al., *J. Med. Chem.*, 32:1231 (1989).
Shi et al., *Cell*, 119:941 (2004).
Sideso et al., *Int. J. Food Sci. Technol.*, 36, 693 (2001).
Simic et al., *J. Am. Chem.Soc.*, 111:5778 (1989).
Smyth, *J. Plant Growth Requl.*, 11:125 (1992).
Subramanian et al., *Biochem. Biophys. Res. Commun.*, 91:1131 (1979).
Suhara et al., *Anal. Biochem.*, 68:632 (1975).
Summers et al., *Microbiology*, 157:583 (2011).
Tamura et al., *Mol. Biol. Evol.*, 24:1596 (2007).
Tassaneeyakul et al., *Biochem. Pharmaco.*, 147:1767 (1994).
Taylor et al., *J. Org. Chem.*, 26:4961 (1961).
Thakur et al., U.S. Pat. No. 7,141,411 B2.
Tsukada et al., *Nature*, 439:811 (2006).
Ueda et al., *J. Biol. Chem.*, 247:2109 (1972).
Vogels et al., *Bacteriol. Rev.*, 40:403 (1976).
Wagner, *Ann. Rev. Nutr.*, 2:229 (1982).
Westerterp-Plantenga et al., *Physiol. Behav.*, 89:85 (2006).
Woolfolk, *J. Bacteriol.*, 123:1088 (1975).
Yamaoka-Yano et al., *Allelopathy J.*, 5:23 (1998).
Yamaoka-Yano et al., *Rev. Microbiol.*, 30:62 (1999).
Yu et al., *J. Bacteriol.*, 190:772 (2008).
Yu et al., *J. Bacteriol.*, 191:4624 (2009).
Yu et al., *J. Ind. Microbiol. Biotechnol.*, 34:311 (2007).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is

1. An isolated chimeric polypeptide which comprises a N-demethylase or a reductase having at least 96% amino acid sequence identity to a polypeptide encoded by a polynucleotide comprising SEQ ID NO: 37, or having at least 85% identity to a polypeptide encoded by a polynucleotide comprising SEQ ID NO:38 or 39 or SEQ ID NO:43.

2. The isolated chimeric polypeptide of claim 1 which has at least 98% amino acid sequence identity to a polypeptide encoded by a polynucleotide comprising SEQ ID NO:37.

3. The isolated chimeric polypeptide of claim 1 which has at least 90% amino acid sequence identity to a polypeptide encoded by a polynucleotide comprising SEQ ID NO:38.

4. The isolated chimeric polypeptide of claim 1 which has at least 90% amino acid sequence identity to a polypeptide encoded by a polynucleotide comprising SEQ ID NO:39.

5. The isolated chimeric polypeptide of claim 1 which has at least 90% amino acid sequence identity to a polypeptide encoded by a polynucleotide comprising SEQ ID NO:43.

6. An isolated polynucleotide encoding a chimeric polypeptide having a N-demethylase or a reductase with at least 96% amino acid sequence identity to a polypeptide encoded by a polynucleotide comprising SEQ ID NO: 37, or having at least 85% identity to a polypeptide encoded by a polynucleotide comprising SEQ ID NO:38 or 39, or SEQ ID NO:43.

7. A composition comprising a plurality of isolated polypeptides, wherein one of the plurality of polypeptides is a fusion polypeptide having at least 96% amino acid sequence identity to a polypeptide encoded by a polynucleotide comprising SEQ ID NO: 37, or having at least 85% identity to a polypeptide encoded by a polynucleotide comprising SEQ ID NO:38 or 39, or SEQ ID NO:43.

8. An isolated host cell comprising the polynucleotide of claim 6 or augmented with a recombinant polynucleotide encoding a polypeptide with at least 96% amino acid sequence identity to a polypeptide encoded by at least one of SEQ ID NO: 37or having at least 85% identity to a polypeptide encoded by a polynucleotide comprising SEQ ID NO:38, or 39, or SEQ ID NO:43.

9. The host cell of claim 8 which is a bacterial or yeast cell.

10. A spray-dried preparation of the host cell of claim 9.

11. A method to prepare products of an enzymatic reaction, comprising:
   a) providing a preparation having the recombinant host cell of claim 8; and
   b) combining the preparation and an aqueous solution comprising a substrate for an enzyme in the preparation under conditions that yield a product of the enzyme catalyzed reaction.

12. The method of claim 11 further comprising isolating the product.

13. The method of claim 11 wherein the product is a xanthine.

14. The method of claim 11 wherein the substrate is a purine alkaloid.

15. A method to detect a purine alkaloid in an environmental sample or a physiological sample, comprising:
   a) providing a preparation having the recombinant host cell of claim 8;
   b) contacting the sample and the preparation under conditions effective for an enzyme in the preparation to convert a purine alkaloid to a product; and
   c) detecting the presence or amount of the product.

16. The method of claim 15 wherein the sample is a waste water sample.

17. The method of claim 15 wherein the physiological sample is a fluid sample.

18. The method of claim 11 or 15 wherein the host cell is a yeast cell.

19. The isolated chimeric polypeptide of claim 1 which comprises polypeptide sequences encoded by SEQ ID NO:37, SEQ ID NO:38, SEQ ID NO:39, or SEQ ID NO:43.

* * * * *

UNITED STATES PATENT AND TRADEMARK OFFICE
CERTIFICATE OF CORRECTION

PATENT NO. : 8,951,752 B2  Page 1 of 3
APPLICATION NO. : 14/344037
DATED : February 10, 2015
INVENTOR(S) : Subramanian et al.

It is certified that error appears in the above-identified patent and that said Letters Patent is hereby corrected as shown below:

In the Specification

In column 4, line 2, delete "$[2Fe-25]_R$," and insert --$[2Fe-2S]_R$,--, therefor In column 6, line 35, delete "normaturally" and insert --nonnaturally--, therefor In column 8, line 36, delete "IKlebsiella" and insert --/Klebsiella--, therefor In column 10, line 52, delete "IKlebsiella" and insert --/Klebsiella--, therefor In column 14, line 22, delete "Gluck" and insert --Glück--, therefor In column 19, line 18, delete "gene/Cytochrome)" and insert --gene/Cytochrome1--, therefor In column 22, line 8, delete "200° C." and insert --200°C.--, therefor In column 22, line 45, delete "(KPi)" and insert --$(KP_i)$--, therefor In column 22, line 46, delete "KPi" and insert --$KP_i$--, therefor In column 22, line 66, delete "KPi" and insert --$KP_i$--, therefor In column 23, line 29, delete "(KPi)" and insert --$(KP_i)$--, therefor In column 23, line 30, delete "KPi" and insert --$KP_i$--, therefor In column 23, line 36, delete "KPi" and insert --$KP_i$--, therefor In column 26, line 47, delete "(KPi)" and insert --$(KP_i)$--, therefor In column 26, line 48, delete "KPi" and insert --$KP_i$--, therefor In column 26, line 51, delete "-80° C." and insert -- -80°C.--, therefor Signed and Sealed this
Twenty-fourth Day of November, 2015

Michelle K. Lee
*Director of the United States Patent and Trademark Office*

CERTIFICATE OF CORRECTION (continued)
U.S. Pat. No. 8,951,752 B2

In column 27, line 39, delete "I11;" and insert --III;--, therefor

In column 27, line 40, delete "KPi" and insert --$KP_i$--, therefor

In column 27, line 42, delete "30° C." and insert --30°C.--, therefor

In column 27, line 51, delete "KPi" and insert --$KP_i$--, therefor

In column 28, line 9, delete "KPi" and insert --$KP_i$--, therefor

In column 28, line 29, delete "KPi" and insert --$KP_i$--, therefor

In column 28, line 33, delete "KPi" and insert --$KP_i$--, therefor

In column 28, line 33, delete "30° C." and insert --30°C.--, therefor

In column 28, line 60, delete "KPi" and insert --$KP_i$--, therefor

In column 31, line 21, delete "mg" and insert --$mg^{-1}$--, therefor

In column 31, line 51, delete "KPi" and insert --$KP_i$--, therefor

In column 31, line 55, delete "KPi" and insert --$KP_i$--, therefor

In column 34, line 2, delete "yanoikuyaeB1" and insert --yanoikuyae B1--, therefor In column 39, line 50, after "cloned", delete "¶", therefor In column 39, line 51, delete "Did" and insert --did--, therefor In column 39, line 53, delete "His-taq" and insert --His-tag--, therefor In column 39, line 64, delete "DpnI" and insert --DpnI--, therefor In column 39, line 66, delete "Cloni®" and insert --cloni®--, therefor In column 40, line 42, delete "His-taqqed" and insert --His-tagged--, therefor In column 40, line 56, delete "AKTA" and insert --ÄKTA--, therefor In column 40, line 59, delete "KP," and insert --$KP_i$--, therefor In column 40, line 66, delete "KP," and insert --$KP_i$--, therefor In column 41, line 2, delete "1 50" and insert --1 L 50--, therefor In column 41, line 10, delete "KP," and insert --$KP_i$--, therefor In column 41, line 15, delete "30° C." and insert --30°C.--, therefor In column 41, line 18, delete "pmol" and insert --μmol--, therefor

CERTIFICATE OF CORRECTION (continued)
U.S. Pat. No. 8,951,752 B2

In column 41, line 35, delete "pmole" and insert --µmole--, therefor

In column 41, line 42, delete "($V_s$," and insert --($V_c$,--, therefor

In column 41, line 65, delete "(ESI)" and insert --([S])--, therefor

In column 42, line 28, delete "KPi" and insert --$KP_i$--, therefor

In column 44, Table 6, line 5, delete "serach" and insert --search--, therefor

In column 50, line 46, delete "DpnI-treated" and insert --DpnI-treated--, therefor In column 51, line 20, after "4.3-kb", delete "¶", therefor In column 53, below TABLE 8-continued, line 3, delete "kinectic paratmeters." and insert --kinetic parameters.--, therefor In column 53, line 35, delete "$N_I$-position" and insert --$N_1$-position--, therefor In column 59, line 1, delete "Reference" and insert --References--, therefor In column 59, line 26, delete "Life." and insert --Life--, therefor In column 59, line 43, delete "Nagel" and insert --Hagel--, therefor In column 59, line 52, delete "Nodeikadaku" and insert --Nogeikagaku--, therefor In column 60, line 31, delete "Schrader" and insert --Schräder--, therefor In the Claims In column 102, line 33, in Claim 8, delete "37or" and insert --37 or--, therefor

SEQUENCE LISTING

<160> NUMBER OF SEQ ID NOS: 84

<210> SEQ ID NO 1
<211> LENGTH: 17
<212> TYPE: PRT
<213> ORGANISM: Artificial Sequence
<220> FEATURE:
<223> OTHER INFORMATION: A synthetic sequence
<220> FEATURE:
<221> NAME/KEY: misc_feature
<222> LOCATION: 14
<223> OTHER INFORMATION: Xaa = any amino acid

<400> SEQUENCE: 1

Met Phe Ala Asp Ile Asn Lys Gly Asp Ala Phe Gly Thr Xaa Val Gly
 1               5                  10                  15

Asn

<210> SEQ ID NO 2
<211> LENGTH: 16
<212> TYPE: PRT
<213> ORGANISM: Artificial Sequence
<220> FEATURE:
<223> OTHER INFORMATION: A synthetic sequence

<400> SEQUENCE: 2

Met Lys Pro Thr Ala Phe Asp Tyr Ile Arg Pro Thr Ser Leu Pro Glu
 1               5                  10                  15

<210> SEQ ID NO 3
<211> LENGTH: 25
<212> TYPE: PRT
<213> ORGANISM: Artificial Sequence
<220> FEATURE:
<223> OTHER INFORMATION: A synthetic sequence

<400> SEQUENCE: 3

Met Glu Gln Ala Ile Ile Asn Asp Glu Arg Glu Tyr Leu Arg His Phe
 1               5                  10                  15

Trp His Pro Val Cys Thr Val Thr Glu
             20                  25

<210> SEQ ID NO 4
<211> LENGTH: 25
<212> TYPE: PRT
<213> ORGANISM: Artificial Sequence
<220> FEATURE:
<223> OTHER INFORMATION: A synthetic sequence

<400> SEQUENCE: 4

Met Lys Glu Gln Leu Lys Pro Leu Leu Glu Asp Lys Thr Tyr Leu Arg
 1               5                  10                  15

His Phe Trp His Pro Val Cys Thr Leu
             20                  25

<210> SEQ ID NO 5
<211> LENGTH: 36
<212> TYPE: DNA
<213> ORGANISM: Artificial Sequence
<220> FEATURE:
<223> OTHER INFORMATION: A synthetic primer

<400> SEQUENCE: 5
agctctgacg tcctgcgcct tatccggtaa ctatcg                            36

```
<210> SEQ ID NO 6
<211> LENGTH: 36
<212> TYPE: DNA
<213> ORGANISM: Artificial Sequence
<220> FEATURE:
<223> OTHER INFORMATION: A synthetic primer

<400> SEQUENCE: 6
agctagggtc caacgtttac aatttcaggt ggcact                            36

<210> SEQ ID NO 7
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)..(20)
<223> OTHER INFORMATION: n = any nucleic acid

<400> SEQUENCE: 7
atggarcarg cnatyatyaa                                              20

<210> SEQ ID NO 8
<211> LENGTH: 24
<212> TYPE: DNA
<213> ORGANISM: Artificial Sequence
<220> FEATURE:
<223> OTHER INFORMATION: A synthetic primer

<400> SEQUENCE: 8
cagccatttt ctatactgga tcga                                         24

<210> SEQ ID NO 9
<211> LENGTH: 20
<212> TYPE: DNA
<213> ORGANISM: Artificial Sequence
<220> FEATURE:
<223> OTHER INFORMATION: A synthetic primer

<400> SEQUENCE: 9
tacagtaagt ggaaaccgcc                                              20

<210> SEQ ID NO 10
<211> LENGTH: 20
<212> TYPE: DNA
<213> ORGANISM: Artificial Sequence
<220> FEATURE:
<223> OTHER INFORMATION: A synthetic primer

<400> SEQUENCE: 10
caatgtgtca tgtccggtag                                              20

<210> SEQ ID NO 11
<211> LENGTH: 18
<212> TYPE: DNA
<213> ORGANISM: Artificial Sequence
<220> FEATURE:
<223> OTHER INFORMATION: A synthetic primer

<400> SEQUENCE: 11
caggaaacag ctatgacc                                                18

<210> SEQ ID NO 12
```

```
<211> LENGTH: 20
<212> TYPE: DNA
<213> ORGANISM: Artificial Sequence
<220> FEATURE:
<223> OTHER INFORMATION: A synthetic primer

<400> SEQUENCE: 12
ggcggtttcc acttactgta                                               20

<210> SEQ ID NO 13
<211> LENGTH: 20
<212> TYPE: DNA
<213> ORGANISM: Artificial Sequence
<220> FEATURE:
<223> OTHER INFORMATION: A synthetic primer

<400> SEQUENCE: 13
cattcaggct gcgcaactgt                                               20

<210> SEQ ID NO 14
<211> LENGTH: 20
<212> TYPE: DNA
<213> ORGANISM: Artificial Sequence
<220> FEATURE:
<223> OTHER INFORMATION: A synthetic primer

<400> SEQUENCE: 14
gcagattgta ctgagagtgc                                               20

<210> SEQ ID NO 15
<211> LENGTH: 20
<212> TYPE: DNA
<213> ORGANISM: Artificial Sequence
<220> FEATURE:
<223> OTHER INFORMATION: A synthetic primer

<400> SEQUENCE: 15
atgaargarc arctsaarcc                                               20

<210> SEQ ID NO 16
<211> LENGTH: 20
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(20)
<223> OTHER INFORMATION: n = any nucleic acid

<400> SEQUENCE: 16
aartcngtra arttytccca                                               20

<210> SEQ ID NO 17
<211> LENGTH: 32
<212> TYPE: DNA
<213> ORGANISM: Artificial Sequence
<220> FEATURE:
<223> OTHER INFORMATION: A synthetic primer

<400> SEQUENCE: 17
ctgacaaaag catctctcct cgggccaaga tt                                 32

<210> SEQ ID NO 18
<211> LENGTH: 32
<212> TYPE: DNA
<213> ORGANISM: Artificial Sequence
```

```
<220> FEATURE:
<223> OTHER INFORMATION: A synthetic primer

<400> SEQUENCE: 18
aatcttggcc cgaggagaga tgcttttgtc ag                                32

<210> SEQ ID NO 19
<211> LENGTH: 20
<212> TYPE: DNA
<213> ORGANISM: Artificial Sequence
<220> FEATURE:
<223> OTHER INFORMATION: A synthetic primer

<400> SEQUENCE: 19
acaaaagcat ctctcctcgg                                              20

<210> SEQ ID NO 20
<211> LENGTH: 20
<212> TYPE: DNA
<213> ORGANISM: Artificial Sequence
<220> FEATURE:
<223> OTHER INFORMATION: A synthetic primer

<400> SEQUENCE: 20
ggctggataa cagcttcgat                                              20

<210> SEQ ID NO 21
<211> LENGTH: 20
<212> TYPE: DNA
<213> ORGANISM: Artificial Sequence
<220> FEATURE:
<223> OTHER INFORMATION: A synthetic primer

<400> SEQUENCE: 21
tttccggcgt tgctgcaaac                                              20

<210> SEQ ID NO 22
<211> LENGTH: 20
<212> TYPE: DNA
<213> ORGANISM: Artificial Sequence
<220> FEATURE:
<223> OTHER INFORMATION: A synthetic primer

<400> SEQUENCE: 22
ccaacaccaa tttctcgcct                                              20

<210> SEQ ID NO 23
<211> LENGTH: 20
<212> TYPE: DNA
<213> ORGANISM: Artificial Sequence
<220> FEATURE:
<223> OTHER INFORMATION: A synthetic primer

<400> SEQUENCE: 23
tgtggaaaga tgactcacgt                                              20

<210> SEQ ID NO 24
<211> LENGTH: 20
<212> TYPE: DNA
<213> ORGANISM: Artificial Sequence
<220> FEATURE:
<223> OTHER INFORMATION: A synthetic primer

<400> SEQUENCE: 24
cgctagccct gtcgataaca                                              20
```

<210> SEQ ID NO 25
<211> LENGTH: 20
<212> TYPE: DNA
<213> ORGANISM: Artificial Sequence
<220> FEATURE:
<223> OTHER INFORMATION: A synthetic primer

<400> SEQUENCE: 25
tagaggattg cggttgacac                                               20

<210> SEQ ID NO 26
<211> LENGTH: 20
<212> TYPE: DNA
<213> ORGANISM: Artificial Sequence
<220> FEATURE:
<223> OTHER INFORMATION: A synthetic primer

<400> SEQUENCE: 26
aacgagttgc ggtgtcagta                                               20

<210> SEQ ID NO 27
<211> LENGTH: 35
<212> TYPE: DNA
<213> ORGANISM: Artificial Sequence
<220> FEATURE:
<223> OTHER INFORMATION: A synthetic primer

<400> SEQUENCE: 27
gcacggcata tggagcaggc gatcatcaat gatga                              35

<210> SEQ ID NO 28
<211> LENGTH: 35
<212> TYPE: DNA
<213> ORGANISM: Artificial Sequence
<220> FEATURE:
<223> OTHER INFORMATION: A synthetic primer

<400> SEQUENCE: 28
gcgcgcgaat tcttatatgt agctcctatc gcttt                              35

<210> SEQ ID NO 29
<211> LENGTH: 35
<212> TYPE: DNA
<213> ORGANISM: Artificial Sequence
<220> FEATURE:
<223> OTHER INFORMATION: A synthetic primer

<400> SEQUENCE: 29
gcgataggag ctacatataa gaattcgagc tccgt                              35

<210> SEQ ID NO 30
<211> LENGTH: 35
<212> TYPE: DNA
<213> ORGANISM: Artificial Sequence
<220> FEATURE:
<223> OTHER INFORMATION: A synthetic primer

<400> SEQUENCE: 30
acggagctcg aattcttata tgtagctcct atcgc                              35

<210> SEQ ID NO 31
<211> LENGTH: 66
<212> TYPE: DNA
<213> ORGANISM: Artificial Sequence
<220> FEATURE:
<223> OTHER INFORMATION: A synthetic primer -continued

<400> SEQUENCE: 31
gaaataattt tgtttaactt taagaaggag atatacatat gaaggagcaa ctgaagccgc    60
tgctag    66

<210> SEQ ID NO 32
<211> LENGTH: 60
<212> TYPE: DNA
<213> ORGANISM: Artificial Sequence
<220> FEATURE:
<223> OTHER INFORMATION: A synthetic primer

<400> SEQUENCE: 32
atctcagtgg tggtggtggt ggtgctcgag ctgttcttct tcaataacat tcgtcaagac    60

<210> SEQ ID NO 33
<211> LENGTH: 30
<212> TYPE: DNA
<213> ORGANISM: Artificial Sequence
<220> FEATURE:
<223> OTHER INFORMATION: A synthetic primer

<400> SEQUENCE: 33
ggccggcata tgaacaaact tgacgtcaac    30

<210> SEQ ID NO 34
<211> LENGTH: 32
<212> TYPE: DNA
<213> ORGANISM: Artificial Sequence
<220> FEATURE:
<223> OTHER INFORMATION: A synthetic primer

<400> SEQUENCE: 34
ggccggaagc tttcacagat cgagaacgat tt    32

<210> SEQ ID NO 35
<211> LENGTH: 25
<212> TYPE: PRT
<213> ORGANISM: Artificial Sequence
<220> FEATURE:
<223> OTHER INFORMATION: A synthetic sequence

<400> SEQUENCE: 35

Met Glu Gln Ala Ile Ile Asn Asp Glu Arg Glu Tyr Leu Arg His Phe
 1               5                  10                  15

Trp His Pro Val Cys Thr Val Thr Glu
            20                  25

<210> SEQ ID NO 36
<211> LENGTH: 25
<212> TYPE: PRT
<213> ORGANISM: Artificial Sequence
<220> FEATURE:
<223> OTHER INFORMATION: A synthetic sequence

<400> SEQUENCE: 36

Met Lys Glu Gln Leu Lys Pro Leu Leu Glu Asp Lys Thr Tyr Leu Arg
 1               5                  10                  15

His Phe Trp His Pro Val Val Thr Leu
            20                  25

<210> SEQ ID NO 37
<211> LENGTH: 1056
<212> TYPE: DNA

<213> ORGANISM: Artificial Sequence
<220> FEATURE:
<223> OTHER INFORMATION: A synthetic sequence

<400> SEQUENCE: 37

| | | | | | |
|---|---|---|---|---|---|
| atggagcagg | cgatcatcaa | tgatgaacgg | gagtatcttc | gccatttctg | gcatcccgta | 60 |
| tgtactgtaa | ctgagcttga | aaaggcgcat | ccttccagcc | tcggcccct | ggccgttaag | 120 |
| ctgctgaatg | aacagctcgt | tgtcgccaag | ctaggcgatg | agtacgtcgc | gatgcgtgat | 180 |
| agatgcgctc | atcgatcagc | taagctttcc | ttgggtacag | taagtggaaa | ccgcctacag | 240 |
| tgcccctatc | acggatggca | atatgatacg | catggcgctt | gccagctcgt | accagcgtgc | 300 |
| cccaacagcc | caatacccaa | caaggctaaa | gttgatcgct | tcgattgcga | agaacgctat | 360 |
| ggattgattt | ggattcgatt | ggactctagt | tttgactgca | ctgaaattcc | ctactttagt | 420 |
| gcagccaacg | atcctaggtt | gcgtattgtt | atacaagaac | cttactggtg | ggatgcgact | 480 |
| gcagaacgta | gatgggaaaa | ttttacagat | ttttctcact | ttgcattcat | tcacccaggc | 540 |
| acgcttttcg | atccaaataa | tgctgaacct | ccaattgttc | cgatggatcg | attcaatggt | 600 |
| cagtttcggt | ttgtctacga | cacgccagaa | gatatggctg | tcccaaatca | ggctccaatt | 660 |
| ggttcatttt | cgtatacttg | cagcatgccg | tttgctatta | accttgaagt | atccaaatac | 720 |
| tccagcagtt | cgctgcatgt | gttattcaat | gtgtcatgtc | cggtagacag | ccacaccacg | 780 |
| aaaaactttc | tgatcttcgc | tagggagcaa | tcggacgact | cggattatct | gcacattgca | 840 |
| tttaatgatc | tcgtcttcgc | tgaagacaaa | ccagtaattg | agtcccaatg | gcctaaagac | 900 |
| gcgccagcag | atgaggtctc | agtagtcgca | gataaggtat | cgatacaata | tagaaaatgg | 960 |
| ctgcgggaac | taaaagaagc | tcataaagaa | ggttcacaag | ccttccgaag | tgctttgtta | 1020 |
| gacccagtca | ttgaaagcga | taggagctac | atataa | | | 1056 |

<210> SEQ ID NO 38
<211> LENGTH: 1068
<212> TYPE: DNA
<213> ORGANISM: Artificial Sequence
<220> FEATURE:
<223> OTHER INFORMATION: A synthetic sequence

<400> SEQUENCE: 38

| | | | | | |
|---|---|---|---|---|---|
| atgaaggagc | aactgaagcc | gctgctagaa | gacaagactt | accttcgcca | cttctggcat | 60 |
| cccgtgtgta | cccttaatga | attcgaacgc | gccaacgcca | gtgggcacgg | ccccatgggc | 120 |
| gtcaccttgc | taggcgagaa | attggtgttg | gccaggttaa | attcaaagat | cattgcggct | 180 |
| gctgaccgat | gtgctcatcg | atcggcacag | ctctccatcg | gccgcgtttg | cagcaacgcc | 240 |
| ggaaaggact | atctcgaatg | cccgtatcac | ggctggcgct | acgatgaggc | tggggcctgt | 300 |
| caactgatcc | ctgcttgccc | tgacaaaagc | atctctcctc | gggccaagat | tcctcattc | 360 |
| gattgtgagg | tgaaatacga | catcgtgtgg | gtacggctgg | ataacagctt | cgattgcact | 420 |
| cagattccat | acctcagcga | tttcgataat | cccgacatgc | aggtaatcgt | tgccgattcg | 480 |
| tatatttggg | agactgttgc | cgagcggcgg | tgggagaact | ttacagattt | ttcgcacttt | 540 |
| gccttcgtac | acccagggac | gctctatgat | ccgttttcg | ctagccaccc | aactgtttac | 600 |
| gtgaatcgcg | ttgatggtga | gttgcaattc | aaacttgctc | cgccgcgtga | aatgaaaggc | 660 |
| atcccgccag | aagcaccgat | gggtgacttc | acctaccgct | gcacaatgcc | gtattcagta | 720 |
| aatcttgaaa | tcaaattgtg | gaagatgac | tcacgtttcg | ttctttggac | taccgctagc | 780 |
| cctgtcgata | acaagtcttg | ccggaatttt | atgattattg | tgcgtgagaa | ggataaccaa | 840 |

```
cctgatcata tgcacctggc tttccagaag cgggtgcttg acgaagacca gcctgttatc      900
gaatcgcaat ggcctctcga atacagacct cggaagtctc cgttgcaacc gataaaattt      960
tccgtccagt tccgcaaatg cataaagagc tatctctgtc agccgttgaa ggacgggag      1020 gcgttccgcg attccgtctt gacgaatgtt attgaagaag aacagtaa                  1068
```

<210> SEQ ID NO 39
<211> LENGTH: 855
<212> TYPE: DNA
<213> ORGANISM: Artificial Sequence
<220> FEATURE:
<223> OTHER INFORMATION: A synthetic sequence

<400> SEQUENCE: 39

```
atgtctactg accaagtaat ttttaacgac tggcatccag tcgctgcttt ggaagatgta       60
tctctcgata acgataccg ctgtcgacta ctaggtcgta cagttagtta tgtgaaaaca       120
tctgatgctg ttaatgctca ttgggaagaa agtgcagatg aaattaagac catccgcgct      180
aaagaaatct atggtcttct gtggctctcc tttgccgaca acccagtga gatgttcgat       240 attgcagagt tcaaggaacc tgatcgccga atcgtcagcg ctggatctgt gcgcgtaaat      300
gtctcaggac tgcgtgctat cgaaaacttt ctggacatgg ctcatttccc ttttgttcat     360
acggatattt tgggtgcaga gccactgacg gaagttgagc cgtataacgt caactatgat      420
gaaactgttg atgagatctt cgctactgag tgtaagttcc cgcaacctaa aggctcagct     480
actgctgtcg agccaattga tatgcagtat atataccgca ttacacggcc atattccgcc     540 atttatata aaacttgccc gcccgaaccg catagatggg atgccctcgg tctgtttatt       600
caacctgtag acgaagattg gtgcatagcg catacaatta tgtgctatgt ggatgacgtt      660
aactcagatc aacaacttcg ccatttccag cagacgattt ttggccagga cttgatgatt      720
cttatcaacc aagttccaaa gcgtcttccc ctggctgcaa gtcgagagag cccagtccgg      780
gccgatgtgc ttgcaacagc ttatcgtcgc tggctgcgtg agaaaggtgt gcaatatggt      840
gctctgcggg actaa                                                      855
```

<210> SEQ ID NO 40
<211> LENGTH: 30
<212> TYPE: PRT
<213> ORGANISM: Artificial Sequence
<220> FEATURE:
<223> OTHER INFORMATION: A synthetic sequence
<220> FEATURE:
<221> NAME/KEY: misc_feature
<222> LOCATION: (1)...(30)
<223> OTHER INFORMATION: Xaa = any amino acid

<400> SEQUENCE: 40

```
Met Asn Lys Leu Asp Val Asn Gln Xaa Phe Pro Ile Ala Thr Thr Glu
1               5                   10                  15

Asp Leu Pro Lys Arg His Val Phe His Ala Thr Leu Leu Gly
            20                  25                  30
```

<210> SEQ ID NO 41
<211> LENGTH: 30
<212> TYPE: PRT
<213> ORGANISM: Artificial Sequence
<220> FEATURE:
<223> OTHER INFORMATION: A synthetic sequence
<220> FEATURE:
<221> NAME/KEY: misc_feature
<222> LOCATION: (1)...(30)

<223> OTHER INFORMATION: Xaa = any amino acid

<400> SEQUENCE: 41

Ser Thr Asp Gln Val Ile Phe Asn Asp Xaa His Pro Val Ala Ala Leu
1               5                   10                  15

Glu Asp Val Ser Leu Asp Lys Arg Xaa Arg Xaa Arg Leu Leu
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: A synthetic sequence
<220> FEATURE:
<221> NAME/KEY: misc_feature
<222> LOCATION: (1)...(30)
<223> OTHER INFORMATION: Xaa = any amino acid

<400> SEQUENCE: 42

Met Ile Thr Leu Xaa Asp Xaa Glu Leu Ser Gly Asn Xaa Xaa Lys Ile
1               5                   10                  15

Arg Leu Phe Leu Ser Ile Leu Asn Met Gly Xaa Gln Thr Glu
            20                  25                  30

<210> SEQ ID NO 43
<211> LENGTH: 604
<212> TYPE: PRT
<213> ORGANISM: Artificial Sequence
<220> FEATURE:
<223> OTHER INFORMATION: A synthetic sequence

<400> SEQUENCE: 43

His His His His His His Ser Ser Gly Leu Val Pro Arg Gly Ser His
1               5                   10                  15

Met Asn Lys Leu Asp Val Asn Gln Trp Phe Pro Ile Ala Thr Thr Glu
            20                  25                  30

Asp Leu Pro Lys Arg His Val Phe His Ala Thr Leu Leu Gly Gln Glu
        35                  40                  45

Met Ala Ile Trp Arg Asp Asp Ser Gly Ser Val Asn Ala Trp Glu Asn
    50                  55                  60

Arg Cys Pro His Arg Gly Leu Arg Leu Thr Leu Gly Ala Asn Thr Gly
65                  70                  75                  80

Asn Glu Leu Arg Cys Gln Tyr His Gly Trp Thr Tyr Glu Ser Gly Thr
                85                  90                  95

Gly Gly Cys Thr Phe Val Pro Ala His Arg Asp Ala Pro Pro Pro Asn
            100                 105                 110

Ala Ala Arg Val Asn Thr Phe Pro Val Arg Glu Lys His Gly Phe Ile
        115                 120                 125

Trp Thr Thr Leu Gly Gln Pro Pro Gly Glu Pro Ile Ser Ile Leu Asp
    130                 135                 140

Asp Ala Gln Leu Val Asn Ala Val Lys Thr Asn Leu His Ser Val Val
145                 150                 155                 160

Ile Asp Ala Asp Ile Asp Gly Val Val Ser Val Leu Arg Gln Asn Leu
                165                 170                 175

Ser Ala Phe Ile Asp Val Phe Gly Ala Ala Ser Ala Glu Asp Leu His
            180                 185                 190

Leu Lys Ser Met Leu Gln Asp Arg Gly Ile Leu Val Thr Arg Ser Gly
        195                 200                 205

Ser Ile Ala Ile His Phe Tyr Met Gln Arg Ser Thr Ile Ser Lys Cys
210                 215                 220

Val Val His Ala Gln Val Leu Thr Pro Gly Arg Pro Gly Tyr Glu Leu
225                 230                 235                 240

Gln Lys Asn Tyr Ser Tyr Ala Met Asn Val Ile Arg Arg Ala Ala Glu
            245                 250                 255

Ala Val Ala Thr Asp Leu Ile Ser Ile Thr Asp Ile Ser Asp Gln Thr
        260                 265                 270

Ile Glu Lys Leu Glu Val Val Arg Glu Asn Met Thr Lys Ala Pro Pro
    275                 280                 285

Thr His Tyr Ile Cys Glu Val Val Thr Arg Thr Gln Glu Thr Gly Asp
290                 295                 300

Ile Asn Ser Tyr Trp Leu Lys Pro Ile Gly Tyr Pro Leu Pro Ala Phe
305                 310                 315                 320

Ser Pro Gly Met His Ile Ser Ile Thr Thr Pro Glu Gly Ser Ile Arg
            325                 330                 335

Gln Tyr Ser Leu Val Asn Gly Pro Asp Glu Arg Glu Ser Phe Ile Ile
        340                 345                 350

Gly Val Lys Lys Glu Ile Gln Ser Arg Gly Gly Ser Arg Ser Met His
    355                 360                 365

Glu Asp Val Lys Val Gly Thr Gln Leu Lys Val Thr Leu Pro Arg Asn
370                 375                 380

Gly Phe Pro Leu Val Gln Thr Arg Lys His Pro Ile Leu Val Ala Gly
385                 390                 395                 400

Gly Ile Gly Ile Thr Pro Ile Leu Cys Met Ala Gln Ala Leu Asp Gln
            405                 410                 415

Gln Gly Ser Ser Tyr Glu Ile His Tyr Phe Ala Arg Ala Phe Glu His
        420                 425                 430

Val Pro Phe Gln Asp Arg Leu Thr Ala Leu Gly Asp Arg Leu Asn Val
    435                 440                 445

His Leu Gly Leu Gly Pro Asp Glu Thr Arg Ala Lys Leu Pro Asp Ile
450                 455                 460

Met Glu Ile His Asn Ala Gln Asp Val Asp Val Tyr Thr Cys Gly Pro
465                 470                 475                 480

Gln Pro Met Ile Glu Thr Val Ser Ala Val Ala Leu Ala His Gly Ile
            485                 490                 495

Ala Glu Glu Ser Ile Arg Phe Glu Phe Phe Ser Lys Lys Asn Asp Val
        500                 505                 510

Pro Val Ser Asp Glu Glu Tyr Glu Val Glu Leu Lys Lys Thr Gly Gln
    515                 520                 525

Ile Phe Thr Val Ser Pro Gly Ser Thr Leu Leu Gln Ala Cys Leu Asp
530                 535                 540

Asn Asp Val Arg Ile Glu Ala Ser Cys Glu Gln Gly Val Cys Gly Thr
545                 550                 555                 560

Cys Ile Thr Pro Val Val Ser Gly Asp Leu His His Asp Thr Tyr
            565                 570                 575

Leu Ser Lys Lys Glu Arg Glu Ser Gly Lys Trp Ile Met Pro Cys Val
        580                 585                 590

Ser Arg Cys Lys Ser Lys Lys Ile Val Leu Asp Leu
            595                 600

<210> SEQ ID NO 44
<211> LENGTH: 669
<212> TYPE: DNA

<213> ORGANISM: Artificial Sequence
<220> FEATURE:
<223> OTHER INFORMATION: A synthetic sequence

<400> SEQUENCE: 44

```
gtgattacac tctatgacta tgagctttcc gggaactgct acaagatcag gcttttttg      60 tccattctga atatgggata ccaaactgag cctgtagagt tctatccgtc gcgtgagcat    120
aaatctgaag cgttcctgaa aatcaatcct ctcggccaac ttcctgcttt gaaggatggt    180
gatctcgtgc tgagggacgc acaggcaatt ctcgtctatc tggccactca gtatgataag    240
agctgctact ggtacccgac cgcccgcccg gatctgatgg ctgaggtcaa catgtggatg    300
gcctttgctg atagcctgac cagcaccatt tcttccgcgc gattacatga cttgttttc     360 tatgaattcg atgtaaatgc atgccgcctg cgtgcccgag atttgttgag gatattggat    420
gaacatcttt ggttcaggga tctaaagggt cttcaatata tttgtagttc gctgcatcct    480
acgatcgcag acatcgcctg tttcccatac atcgctttgt cagatgaggc gggcgtatcc    540
ctagaagact tccctgccgt acgtcggtgg gttgataggg taaaacgcct accaggcttt    600
gttgtaatgt cgggagtatt ccccacgtca cctatgtatg aaggttccgc gcgacgggtg    660
agtgcatag                                                            669
```

<210> SEQ ID NO 45
<211> LENGTH: 222
<212> TYPE: PRT
<213> ORGANISM: Artificial Sequence
<220> FEATURE:
<223> OTHER INFORMATION: A synthetic sequence

<400> SEQUENCE: 45

```
Val Ile Thr Leu Tyr Asp Tyr Glu Leu Ser Gly Asn Cys Tyr Lys Ile
  1               5                  10                  15

Arg Leu Phe Leu Ser Ile Leu Asn Met Gly Tyr Gln Thr Glu Pro Val
             20                  25                  30

Glu Phe Tyr Pro Ser Arg Glu His Lys Ser Glu Ala Phe Leu Lys Ile
         35                  40                  45

Asn Pro Leu Gly Gln Leu Pro Ala Leu Lys Asp Gly Asp Leu Val Leu
     50                  55                  60

Arg Asp Ala Gln Ala Ile Leu Val Tyr Leu Ala Thr Gln Tyr Asp Lys
 65                  70                  75                  80

Ser Cys Tyr Trp Tyr Pro Thr Ala Arg Pro Asp Leu Met Ala Glu Val
                 85                  90                  95

Asn Met Trp Met Ala Phe Ala Asp Ser Leu Thr Ser Thr Ile Ser Ser
            100                 105                 110

Ala Arg Leu His Asp Leu Phe Phe Tyr Glu Phe Asp Val Asn Ala Cys
        115                 120                 125

Arg Leu Arg Ala Arg Asp Leu Leu Arg Ile Leu Asp Glu His Leu Trp
    130                 135                 140

Phe Arg Asp Leu Lys Gly Leu Gln Tyr Ile Cys Ser Ser Leu His Pro
145                 150                 155                 160

Thr Ile Ala Asp Ile Ala Cys Phe Pro Tyr Ile Ala Leu Ser Asp Glu
                165                 170                 175

Ala Gly Val Ser Leu Glu Asp Phe Pro Ala Val Arg Arg Trp Val Asp
            180                 185                 190

Arg Val Lys Arg Leu Pro Gly Phe Val Val Met Ser Gly Val Phe Pro
        195                 200                 205
```

```
Thr Ser Pro Met Tyr Glu Gly Ser Ala Arg Arg Val Ser Ala
    210                 215                 220
```

<210> SEQ ID NO 46
<211> LENGTH: 60
<212> TYPE: PRT
<213> ORGANISM: Janthinobacterium

<400> SEQUENCE: 46

```
Val Ile Thr Leu Tyr Asp Tyr Glu Leu Ser Gly Asn Cys Tyr Lys Ile
 1               5                  10                  15

Arg Leu Phe Leu Ser Ile Leu Asn Met Gly Tyr Gln Thr Glu Pro Val
            20                  25                  30

Glu Phe Tyr Pro Ser Arg Glu His Lys Ser Glu Ala Phe Leu Lys Ile
        35                  40                  45

Asn Pro Leu Gly Gln Leu Pro Ala Leu Lys Asp Gly
    50                  55                  60
```

<210> SEQ ID NO 47
<211> LENGTH: 59
<212> TYPE: PRT
<213> ORGANISM: Artificial Sequence
<220> FEATURE:
<223> OTHER INFORMATION: A hypothetical protein
<220> FEATURE:
<221> NAME/KEY: misc_feature
<222> LOCATION: (1)...(59)
<223> OTHER INFORMATION: Xaa = any amino acid

<400> SEQUENCE: 47

```
Xaa Ile Thr Leu Tyr Asp Tyr Glu Leu Ser Gly Asn Cys Tyr Lys Xaa
 1               5                  10                  15

Arg Xaa Xaa Leu Ser Ile Leu Xaa Xaa Xaa Tyr Xaa Xaa Glu Xaa Val
            20                  25                  30

Glu Phe Xaa Pro Ser Arg Glu His Lys Ser Xaa Ala Phe Leu Xaa Ile
        35                  40                  45

Asn Pro Leu Gly Gln Leu Pro Xaa Leu Xaa Asp
    50                  55
```

<210> SEQ ID NO 48
<211> LENGTH: 60
<212> TYPE: PRT
<213> ORGANISM: Mesorhizobium

<400> SEQUENCE: 48

```
Met Ile Thr Leu Tyr Asp Tyr Glu Leu Ser Gly Asn Cys Tyr Lys Val
 1               5                  10                  15

Arg Met Leu Leu Ser Ile Leu Lys Leu Pro Tyr Thr Ile Glu Thr Val
            20                  25                  30

Glu Phe Phe Pro Ser Arg Glu His Lys Ser Pro Ala Phe Leu Arg Ile
        35                  40                  45

Asn Pro Leu Gly Gln Leu Pro Val Leu Arg Asp Asp
    50                  55                  60
```

<210> SEQ ID NO 49
<211> LENGTH: 60
<212> TYPE: PRT
<213> ORGANISM: Janthinobacterium

<400> SEQUENCE: 49

```
Asp Leu Val Leu Arg Asp Ala Gln Ala Ile Leu Val Tyr Leu Ala Thr
 1               5                  10                  15
```

```
Gln Tyr Asp Lys Ser Cys Tyr Trp Tyr Pro Thr Ala Arg Pro Asp Leu
            20                  25                  30

Met Ala Glu Val Asn Met Trp Met Ala Phe Ala Asp Ser Leu Thr Ser
        35                  40                  45

Thr Ile Ser Ser Ala Arg Leu His Asp Leu Phe Phe
    50                  55                  60

<210> SEQ ID NO 50
<211> LENGTH: 60
<212> TYPE: PRT
<213> ORGANISM: Artificial Sequence
<220> FEATURE:
<223> OTHER INFORMATION: A hypothetical protein
<220> FEATURE:
<221> NAME/KEY: misc_feature
<222> LOCATION: (1)...(60)
<223> OTHER INFORMATION: Xaa = any amino acid

<400> SEQUENCE: 50

Asp Xaa Val Leu Arg Asp Ala Gln Ala Ile Leu Val Tyr Leu Ala Xaa
 1               5                  10                  15

Xaa Tyr Asp Xaa Ser Xaa Xaa Trp Tyr Pro Thr Xaa Xaa Pro Xaa Xaa
            20                  25                  30

Xaa Xaa Xaa Xaa Asn Met Trp Xaa Ala Phe Ala Asp Xaa Leu Thr Xaa
        35                  40                  45

Xaa Ile Ser Xaa Ala Arg Leu His Asp Leu Phe Phe
    50                  55                  60

<210> SEQ ID NO 51
<211> LENGTH: 60
<212> TYPE: PRT
<213> ORGANISM: Mesorhizobium

<400> SEQUENCE: 51

Asp Phe Val Leu Arg Asp Ala Gln Ala Ile Leu Val Tyr Leu Ala Asn
 1               5                  10                  15

Lys Tyr Asp Thr Ser Leu Thr Trp Tyr Pro Thr His Ala Pro Ala Ile
            20                  25                  30

Leu Gly Gln Ala Asn Met Trp Leu Ala Phe Ala Asp Gly Leu Thr Gly
        35                  40                  45

Ser Ile Ser Ala Ala Arg Leu His Asp Leu Phe Phe
    50                  55                  60

<210> SEQ ID NO 52
<211> LENGTH: 60
<212> TYPE: PRT
<213> ORGANISM: Janthinobacterium

<400> SEQUENCE: 52

Tyr Glu Phe Asp Val Asn Ala Cys Arg Leu Arg Ala Arg Asp Leu Leu
 1               5                  10                  15

Arg Ile Leu Asp Glu His Leu Trp Phe Arg Asp Leu Lys Gly Leu Gln
            20                  25                  30

Tyr Ile Cys Ser Ser Leu His Pro Thr Ile Ala Asp Ile Ala Cys Phe
        35                  40                  45

Pro Tyr Ile Ala Leu Ser Asp Glu Ala Gly Val Ser
    50                  55                  60

<210> SEQ ID NO 53
<211> LENGTH: 60
```

```
<212> TYPE: PRT
<213> ORGANISM: Artificial Sequence
<220> FEATURE:
<223> OTHER INFORMATION: A hypothetical protein
<220> FEATURE:
<221> NAME/KEY: misc_feature
<222> LOCATION: (1)...(60)
<223> OTHER INFORMATION: Xaa = any amino acid

<400> SEQUENCE: 53

Tyr Xaa Phe Xaa Xaa Xaa Xaa Cys Arg Xaa Arg Ala Xaa Xaa Leu Leu
1               5                   10                  15

Arg Ile Leu Asp Glu His Leu Trp Xaa Xaa Xaa Xaa Xaa Gly Xaa Gln
            20                  25                  30

Xaa Xaa Cys Xaa Xaa Xaa Xaa Pro Thr Ile Ala Asp Xaa Ala Cys Phe
        35                  40                  45

Pro Tyr Ile Ala Leu Ser Asp Glu Ala Gly Val Ser
    50                  55                  60

<210> SEQ ID NO 54
<211> LENGTH: 60
<212> TYPE: PRT
<213> ORGANISM: Mesorhizobium

<400> SEQUENCE: 54

Tyr Asp Phe Asn Ala Glu Gln Cys Arg Ala Arg Ala His Glu Leu Leu
1               5                   10                  15

Arg Ile Leu Asp Glu His Leu Trp Ala Ala Glu Gln Asn Gly His Gln
            20                  25                  30

Trp Leu Cys Pro Ala Ala Ala Pro Thr Ile Ala Asp Leu Ala Cys Phe
        35                  40                  45

Pro Tyr Ile Ala Leu Ser Asp Glu Ala Gly Val Ser
    50                  55                  60

<210> SEQ ID NO 55
<211> LENGTH: 37
<212> TYPE: PRT
<213> ORGANISM: Janthinobacterium

<400> SEQUENCE: 55

Leu Glu Asp Phe Pro Ala Val Arg Arg Trp Val Asp Arg Val Lys Arg
1               5                   10                  15

Leu Pro Gly Phe Val Val Met Ser Gly Val Phe Pro Thr Ser Pro Met
            20                  25                  30

Tyr Glu Gly Ser Ala
        35

<210> SEQ ID NO 56
<211> LENGTH: 37
<212> TYPE: PRT
<213> ORGANISM: Artificial Sequence
<220> FEATURE:
<223> OTHER INFORMATION: A hypothetical protein
<220> FEATURE:
<221> NAME/KEY: misc_feature
<222> LOCATION: (1)...(37)
<223> OTHER INFORMATION: Xaa = any amino acid

<400> SEQUENCE: 56

Leu Xaa Asp Xaa Pro Ala Val Arg Arg Trp Xaa Asp Arg Val Lys Arg
1               5                   10                  15

Xaa Pro Gly Phe Xaa Val Met Ser Gly Xaa Phe Pro Thr Ser Xaa Xaa
            20                  25                  30
```

```
Xaa Glu Xaa Xaa Xaa
         35

<210> SEQ ID NO 57
<211> LENGTH: 37
<212> TYPE: PRT
<213> ORGANISM: Mesorhizobium

<400> SEQUENCE: 57

Leu Leu Asp Tyr Pro Ala Val Arg Arg Trp Leu Asp Arg Val Lys Arg
 1               5                  10                  15

Ile Pro Gly Phe Thr Val Met Ser Gly Ile Phe Pro Thr Ser Ala Ser
            20                  25                  30

Phe Glu Pro Ala Ser
         35

<210> SEQ ID NO 58
<211> LENGTH: 60
<212> TYPE: PRT
<213> ORGANISM: Janthinobacterium

<400> SEQUENCE: 58

Val Ile Thr Leu Tyr Asp Tyr Glu Leu Ser Gly Asn Cys Tyr Lys Ile
 1               5                  10                  15

Arg Leu Phe Leu Ser Ile Leu Asn Met Gly Tyr Gln Thr Glu Pro Val
            20                  25                  30

Glu Phe Tyr Pro Ser Arg Glu His Lys Ser Glu Ala Phe Leu Lys Ile
        35                  40                  45

Asn Pro Leu Gly Gln Leu Pro Ala Leu Lys Asp Gly
    50                  55                  60

<210> SEQ ID NO 59
<211> LENGTH: 59
<212> TYPE: PRT
<213> ORGANISM: Artificial Sequence
<220> FEATURE:
<223> OTHER INFORMATION: A hypothetical protein
<220> FEATURE:
<221> NAME/KEY: misc_feature
<222> LOCATION: (1)...(59)
<223> OTHER INFORMATION: Xaa = any amino acid

<400> SEQUENCE: 59

Xaa Ile Thr Leu Tyr Asp Tyr Glu Leu Ser Gly Asn Cys Tyr Lys Xaa
 1               5                  10                  15

Arg Leu Xaa Xaa Ser Xaa Leu Xaa Xaa Gly Tyr Xaa Thr Xaa Pro Val
            20                  25                  30

Xaa Phe Tyr Pro Xaa Arg Glu His Lys Ser Glu Xaa Phe Leu Lys Xaa
        35                  40                  45

Asn Pro Leu Gly Gln Leu Pro Xaa Leu Xaa Asp
    50                  55

<210> SEQ ID NO 60
<211> LENGTH: 60
<212> TYPE: PRT
<213> ORGANISM: Mesorhizobium

<400> SEQUENCE: 60

Met Ile Thr Leu Tyr Asp Tyr Glu Leu Ser Gly Asn Cys Tyr Lys Leu
 1               5                  10                  15

Arg Leu Met Met Ser Phe Leu Gly Ile Gly Tyr Lys Thr Val Pro Val
```

```
                20                  25                  30
Asp Phe Tyr Pro Gly Arg Glu His Lys Ser Glu Trp Phe Leu Lys Leu
        35                  40                  45

Asn Pro Leu Gly Gln Leu Pro Val Leu Glu Asp Asp
        50                  55                  60

<210> SEQ ID NO 61
<211> LENGTH: 60
<212> TYPE: PRT
<213> ORGANISM: Janthinobacterium

<400> SEQUENCE: 61

Asp Leu Val Leu Arg Asp Ala Gln Ala Ile Leu Val Tyr Leu Ala Thr
 1               5                  10                  15

Gln Tyr Asp Lys Ser Cys Tyr Trp Tyr Pro Thr Ala Arg Pro Asp Leu
                20                  25                  30

Met Ala Glu Val Asn Met Trp Met Ala Phe Ala Asp Ser Leu Thr Ser
        35                  40                  45

Thr Ile Ser Ser Ala Arg Leu His Asp Leu Phe Phe
        50                  55                  60

<210> SEQ ID NO 62
<211> LENGTH: 59
<212> TYPE: PRT
<213> ORGANISM: Artificial Sequence
<220> FEATURE:
<223> OTHER INFORMATION: A hypothetical protein
<220> FEATURE:
<221> NAME/KEY: misc_feature
<222> LOCATION: (1)...(59)
<223> OTHER INFORMATION: Xaa = any amino acid

<400> SEQUENCE: 62

Leu Xaa Leu Arg Asp Ala Gln Ala Ile Leu Val Tyr Leu Ala Xaa Xaa
 1               5                  10                  15

Tyr Asp Xaa Ser Xaa Xaa Trp Tyr Pro Xaa Xaa Xaa Pro Xaa Leu Xaa
                20                  25                  30

Xaa Glu Xaa Xaa Xaa Trp Xaa Ala Phe Ala Asp Xaa Xaa Thr Xaa Thr
        35                  40                  45

Xaa Ser Xaa Ala Arg Leu His Asp Xaa Xaa Phe
        50                  55

<210> SEQ ID NO 63
<211> LENGTH: 60
<212> TYPE: PRT
<213> ORGANISM: Mesorhizobium

<400> SEQUENCE: 63

Gly Leu Leu Leu Arg Asp Ala Gln Ala Ile Leu Val Tyr Leu Ala Ser
 1               5                  10                  15

Lys Tyr Asp Pro Ser Asn Arg Trp Tyr Pro Arg Asp Asn Pro Ala Leu
                20                  25                  30

Leu Gly Glu Ile Ser Gln Trp Leu Ala Phe Ala Asp Gly Ile Thr Gly
        35                  40                  45

Thr Ala Ser Ala Ala Arg Leu His Asp Gly Leu Phe
        50                  55                  60

<210> SEQ ID NO 64
<211> LENGTH: 60
<212> TYPE: PRT
<213> ORGANISM: Janthinobacterium
```

<400> SEQUENCE: 64

Tyr Glu Phe Asp Val Asn Ala Cys Arg Leu Arg Ala Arg Asp Leu Leu
1               5                   10                  15

Arg Ile Leu Asp Glu His Leu Trp Phe Arg Asp Leu Lys Gly Leu Gln
            20                  25                  30

Tyr Ile Cys Ser Ser Leu His Pro Thr Ile Ala Asp Ile Ala Cys Phe
        35                  40                  45

Pro Tyr Ile Ala Leu Ser Asp Glu Ala Gly Val Ser
    50                  55                  60

<210> SEQ ID NO 65
<211> LENGTH: 59
<212> TYPE: PRT
<213> ORGANISM: Artificial Sequence
<220> FEATURE:
<223> OTHER INFORMATION: A hypothetical protein
<220> FEATURE:
<221> NAME/KEY: misc_feature
<222> LOCATION: (1)...(59)
<223> OTHER INFORMATION: Xaa = any amino acid

<400> SEQUENCE: 65

Tyr Glu Xaa Asp Xaa Xaa Ala Xaa Arg Xaa Xaa Ala Xaa Xaa Leu Xaa
1               5                   10                  15

Arg Ile Leu Asp Glu His Leu Trp Phe Xaa Xaa Xaa Xaa Gly Xaa Xaa
            20                  25                  30

Xaa Ile Cys Ser Xaa Xaa His Pro Thr Ile Ala Asp Xaa Ala Cys Phe
        35                  40                  45

Pro Tyr Xaa Xaa Leu Ser Xaa Glu Xaa Gly Xaa
    50                  55

<210> SEQ ID NO 66
<211> LENGTH: 60
<212> TYPE: PRT
<213> ORGANISM: Mesorhizobium

<400> SEQUENCE: 66

Tyr Glu Leu Asp Ile Asp Ala Ala Arg Val Gly Ala His Arg Leu Phe
1               5                   10                  15

Arg Ile Leu Asp Glu His Leu Trp Phe Gly Glu Gln Glu Gly Arg Asp
            20                  25                  30

Trp Ile Cys Ser Ala Asn His Pro Thr Ile Ala Asp Val Ala Cys Phe
        35                  40                  45

Pro Tyr Val Ile Leu Ser Glu Glu Gly Gly Ile Pro
    50                  55                  60

<210> SEQ ID NO 67
<211> LENGTH: 31
<212> TYPE: PRT
<213> ORGANISM: Janthinobacterium

<400> SEQUENCE: 67

Leu Glu Asp Phe Pro Ala Val Arg Arg Trp Val Asp Arg Val Lys Arg
1               5                   10                  15

Leu Pro Gly Phe Val Val Met Ser Gly Val Phe Pro Thr Ser Pro
            20                  25                  30

<210> SEQ ID NO 68
<211> LENGTH: 30
<212> TYPE: PRT

```
<213> ORGANISM: Artificial Sequence
<220> FEATURE:
<223> OTHER INFORMATION: A hypothetical protein
<220> FEATURE:
<221> NAME/KEY: misc_feature
<222> LOCATION: (1)...(30)
<223> OTHER INFORMATION: Xaa = any amino acid

<400> SEQUENCE: 68

Xaa Asp Xaa Pro Ala Xaa Arg Arg Trp Xaa Asp Arg Val Lys Arg Xaa
  1               5                  10                  15

Xaa Gly Phe Xaa Val Met Ser Gly Val Phe Pro Xaa Xaa Pro
             20                  25                  30

<210> SEQ ID NO 69
<211> LENGTH: 31
<212> TYPE: PRT
<213> ORGANISM: Mesorhizobium

<400> SEQUENCE: 69

Arg Gln Asp Tyr Pro Ala Ile Arg Arg Trp Cys Asp Arg Val Lys Arg
  1               5                  10                  15

Ile Lys Gly Phe Ile Val Met Ser Gly Val Phe Pro Ala Gly Pro
             20                  25                  30

<210> SEQ ID NO 70
<211> LENGTH: 25
<212> TYPE: PRT
<213> ORGANISM: P. putida

<400> SEQUENCE: 70

Met Glu Gln Thr Ile Asn Asn Asn Asp Arg Glu Tyr Leu Arg His Phe
  1               5                  10                  15

Trp His Pro Val Cys Thr Val Thr Glu
             20                  25

<210> SEQ ID NO 71
<211> LENGTH: 25
<212> TYPE: PRT
<213> ORGANISM: Janthinobacterium

<400> SEQUENCE: 71

Met Ser Phe Thr Ala Leu Leu Ala Asp Lys Ser Tyr Leu Arg His Phe
  1               5                  10                  15

Trp His Pro Val Cys Thr Leu Lys Glu
             20                  25

<210> SEQ ID NO 72
<211> LENGTH: 60
<212> TYPE: PRT
<213> ORGANISM: Janthinobacterium

<400> SEQUENCE: 72

Arg Cys Ala His Arg Phe Ala Lys Leu Ser Lys Gly Cys Val Lys Gln
  1               5                  10                  15

Gly Glu Ala Gly Asp Arg Leu Glu Cys Pro Tyr His Gly Trp Gln Tyr
             20                  25                  30

Asp Lys Asp Gly Ala Cys Arg Thr Ile Pro Ala Cys Pro Glu Leu Pro
         35                  40                  45

Ile Pro Lys Lys Ala Arg Ser Asp Ala Phe Glu Cys
     50                  55                  60
```

<210> SEQ ID NO 73
<211> LENGTH: 60
<212> TYPE: PRT
<213> ORGANISM: Janthinobacterium

<400> SEQUENCE: 73

Glu Val Arg Tyr Asp Ile Val Trp Val Arg Leu Asp Ala Ser Phe Gly
1               5                   10                  15

Val Thr Glu Ile Pro Val Phe Ser Asp Trp Glu Glu Gly Met Arg
            20                  25                  30

Val Ile Val Val Asp Ser Tyr Val Trp Gln Thr Thr Ala Glu Arg Arg
        35                  40                  45

Trp Glu Asn Phe Thr Asp Phe Ser His Phe Ala Phe
    50                  55                  60

<210> SEQ ID NO 74
<211> LENGTH: 60
<212> TYPE: PRT
<213> ORGANISM: Janthinobacterium

<400> SEQUENCE: 74

Val His Pro Gly Thr Leu Tyr Asp Ala Ala Tyr Ala Arg Pro Pro Leu
1               5                   10                  15

Ala Pro Val Ser Arg Val Gly Gly Glu Met Arg Phe Ser Ile Glu Pro
            20                  25                  30

Pro Lys Glu Met Thr Asp Gln Leu Pro Asp Asp Cys Pro Ile Gly Ala
        35                  40                  45

Phe Ile Tyr Arg Cys Thr Met Pro Tyr Thr Ile Asn
    50                  55                  60

<210> SEQ ID NO 75
<211> LENGTH: 56
<212> TYPE: PRT
<213> ORGANISM: P. putida

<400> SEQUENCE: 75

Arg Cys Ala His Arg Ser Ala Lys Leu Ser Leu Gly Thr Ile Ala Asn
1               5                   10                  15

Asp Arg Leu Gln Cys Pro Tyr His Gly Trp Gln Tyr Asp Thr Glu Gly
            20                  25                  30

Ala Cys Lys Leu Val Pro Ala Cys Pro Asn Ser Pro Ile Pro Asn Arg
        35                  40                  45

Ala Lys Val Gln Arg Phe Asp Cys
    50                  55

<210> SEQ ID NO 76
<211> LENGTH: 60
<212> TYPE: PRT
<213> ORGANISM: P. putida

<400> SEQUENCE: 76

Glu Glu Arg Tyr Gly Leu Ile Trp Val Arg Leu Asp Ser Ser Tyr Ala
1               5                   10                  15

Cys Thr Glu Ile Pro Tyr Phe Ser Ala Ala Ser Asp Pro Lys Leu Arg
            20                  25                  30

Val Val Ile Gln Glu Pro Tyr Trp Trp Asn Ala Thr Ala Glu Arg Arg
        35                  40                  45

Trp Glu Asn Phe Thr Asp Phe Ser His Phe Ala Phe

<210> SEQ ID NO 77
<211> LENGTH: 58
<212> TYPE: PRT
<213> ORGANISM: P. putida

<400> SEQUENCE: 77

Ile His Pro Gly Thr Leu Phe Asp Pro Asn Asn Ala Glu Pro Pro Ile
1               5                   10                  15

Val Pro Met Asp Arg Phe Asn Gly Gln Phe Arg Phe Val Tyr Asp Thr
            20                  25                  30

Pro Glu Asp Met Ala Val Pro Asp Gln Ala Pro Ile Gly Ser Phe Ser
        35                  40                  45

Tyr Thr Cys Ser Met Pro Phe Ala Ile Asn
    50                  55

<210> SEQ ID NO 78
<211> LENGTH: 11
<212> TYPE: PRT
<213> ORGANISM: Artificial Sequence
<220> FEATURE:
<223> OTHER INFORMATION: A synthetic sequence

<400> SEQUENCE: 78

Met Phe Ala Asp Ile Asn Lys Gly Asp Ala Phe
1               5                   10

<210> SEQ ID NO 79
<211> LENGTH: 11
<212> TYPE: PRT
<213> ORGANISM: Artificial Sequence
<220> FEATURE:
<223> OTHER INFORMATION: A synthetic sequence

<400> SEQUENCE: 79

Met Lys Leu Pro Thr Ala Phe Asp Tyr Ile Arg
1               5                   10

<210> SEQ ID NO 80
<211> LENGTH: 11
<212> TYPE: PRT
<213> ORGANISM: Artificial Sequence
<220> FEATURE:
<223> OTHER INFORMATION: A synthetic sequence

<400> SEQUENCE: 80

Glu Asp Thr Val Gly Arg Pro Leu Pro His Leu
1               5                   10

<210> SEQ ID NO 81
<211> LENGTH: 11
<212> TYPE: PRT
<213> ORGANISM: Artificial Sequence
<220> FEATURE:
<223> OTHER INFORMATION: A synthetic sequence

<400> SEQUENCE: 81

Lys Asp Val Pro Pro Lys Gln Leu Arg Phe Glu
1               5                   10

<210> SEQ ID NO 82
<211> LENGTH: 11
<212> TYPE: PRT
<213> ORGANISM: Artificial Sequence

```
<220> FEATURE:
<223> OTHER INFORMATION: A synthetic sequence

<400> SEQUENCE: 82

Met Thr Ala Asp Glu Leu Val Phe Phe Val Asn
1               5                   10

<210> SEQ ID NO 83
<211> LENGTH: 11
<212> TYPE: PRT
<213> ORGANISM: Artificial Sequence
<220> FEATURE:
<223> OTHER INFORMATION: A synthetic sequence

<400> SEQUENCE: 83

Met Asn Arg Phe Gly Tyr Ala Lys Pro Asn Ala
1               5                   10

<210> SEQ ID NO 84
<211> LENGTH: 11
<212> TYPE: PRT
<213> ORGANISM: Artificial Sequence
<220> FEATURE:
<223> OTHER INFORMATION: A synthetic sequence

<400> SEQUENCE: 84

Val Val His Leu Gln Lys Ala Val Pro Arg Val
1               5                   10
```